United States Patent
Heckel et al.

(10) Patent No.: US 8,921,398 B2
(45) Date of Patent: Dec. 30, 2014

(54) N-CYCLOPROPYL-N-PIPERIDINYL-AMIDE DERIVATIVES, PHARMACEUTICAL COMPOSITIONS AND USES THEREOF

(75) Inventors: Armin Heckel, Biberach an der Riss (DE); Frank Himmelsbach, Mittelbiberach (DE); Elke Langkopf, Biberach an der Riss (DE); Bernd Nosse, Biberach an der Riss (DE); Neil J. Ashweek, Escondido, CA (US); Nicole Harriott, San Diego, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 338 days.

(21) Appl. No.: 13/489,557

(22) Filed: Jun. 6, 2012

(65) Prior Publication Data

US 2013/0143892 A1      Jun. 6, 2013

(30) Foreign Application Priority Data

Jun. 9, 2011   (EP) ..................... 11169297

(51) Int. Cl.
| | | |
|---|---|---|
| C07D 403/12 | (2006.01) | |
| C07D 403/14 | (2006.01) | |
| C07D 413/12 | (2006.01) | |
| C07D 413/14 | (2006.01) | |
| A61K 31/4468 | (2006.01) | |
| A61K 31/497 | (2006.01) | |
| C07D 401/12 | (2006.01) | |
| C07D 401/14 | (2006.01) | |

(52) U.S. Cl.
CPC ............ *C07D 413/14* (2013.01); *C07D 401/12* (2013.01); *C07D 401/14* (2013.01); *C07D 403/12* (2013.01); *C07D 403/14* (2013.01); *C07D 413/12* (2013.01); *Y10S 514/866* (2013.01); *Y10S 514/909* (2013.01)
USPC ...... 514/326; 544/238; 546/209; 514/255.05; 514/866; 514/909

(58) Field of Classification Search
USPC ............................ 514/326; 544/238; 546/209
See application file for complete search history.

(56) References Cited

U.S. PATENT DOCUMENTS

| 7,659,282 B2 | 2/2010 | Yakatan et al. |
| 2011/0021491 A1 | 1/2011 | Tran et al. |
| 2011/0166116 A1 | 7/2011 | Dyck et al. |
| 2013/0065906 A1 | 3/2013 | Nosse et al. |
| 2013/0143892 A1 | 6/2013 | Heckel et al. |

FOREIGN PATENT DOCUMENTS

| EP | 1559428 A1 | 8/2005 |
| WO | 2006113140 A2 | 10/2006 |
| WO | 2007145834 A2 | 12/2007 |
| WO | 2008025798 A1 | 3/2008 |
| WO | 2008109702 A1 | 9/2008 |
| WO | 2010004347 A1 | 1/2010 |
| WO | 2010004348 A1 | 1/2010 |
| WO | 2010149684 A1 | 12/2010 |
| WO | 2010149685 A1 | 12/2010 |
| WO | 2011138427 A2 | 11/2011 |
| WO | 2012080476 A1 | 6/2012 |
| WO | 2012098217 A1 | 7/2012 |
| WO | 2012123449 A1 | 9/2012 |

OTHER PUBLICATIONS

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
International Search Report and Written Opinion for PCT/EP2012/054376 mailed Jun. 18, 2012.
Rew, Y. "Discovery and optimization of piperidyl benzamide derivatives as a novel class of 11.beta.-HSD1 inhibitiors". Bioorg. Med. Chem Letters, vol. 19, No. 6, Jan. 23, 2009, p. 1797-1801.

*Primary Examiner* — Savitha Rao
*Assistant Examiner* — Gregg Polansky
(74) *Attorney, Agent, or Firm* — Michael P. Morris; Timothy X. Witkowski

(57) ABSTRACT

The present invention relates to compounds of general formula I,

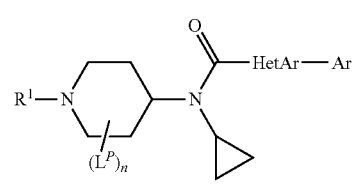

wherein $R^1$, $L^P$, HetAr, Ar, and n are as defined in the application, which have valuable pharmacological properties, and in particular bind to the GPR119 receptor and modulate its activity.

14 Claims, No Drawings

N-CYCLOPROPYL-N-PIPERIDINYL-AMIDE DERIVATIVES, PHARMACEUTICAL COMPOSITIONS AND USES THEREOF

FIELD OF THE INVENTION

The present invention relates to new compounds, in particular compounds of formula I

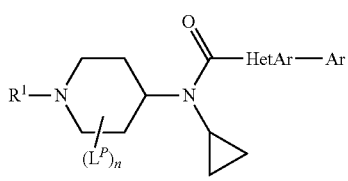

wherein $R^1$, $L^P$, HetAr, Ar, and n are defined as hereinafter, to processes for preparing such compounds, to their use as modulators of the G-protein-coupled receptor GPR119, to methods for their therapeutic use, in particular to methods of treating diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, which means in particular a high frequency of complications as well, leading to a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma.

Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophospha-tidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinolgy 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyper-glycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see 1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

AIM OF THE PRESENT INVENTION

The aim of the present invention is to provide new compounds, in particular new N-cyclopropyl-N-piperidinyl-amide derivatives, which are active with regard to the G-protein-coupled receptor GPR119.

Another aim of the present invention is to provide new compounds, in particular new N-cyclopropyl-N-piperidinyl-amide derivatives, which are agonists of the G-protein-coupled receptor GPR119.

A further aim of the present invention is to provide new compounds, in particular new N-cyclopropyl-N-piperidinyl-amide derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular N-cyclopropyl-N-piperidinyl-amide derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, in particular as GPR119 agonists.

In a first aspect the invention thus relates to compounds of formula I

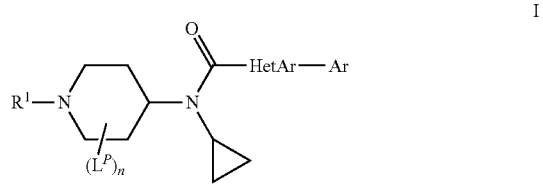

wherein

R$^1$ is selected from the group R$^1$-G1 consisting of
 a 5- or 6-membered heteroaromatic ring which contains 1, 2 or 3 heteroatoms independently of each other selected from N, NR$^N$, O and S; and wherein optionally a second carbocyclic ring is condensed to said heteroaromatic ring, wherein said second carbocyclic ring is unsaturated or aromatic and 5- or 6-membered and may optionally contain 1, 2 or 3 heteroatoms independently of each other selected from N, NR$^N$, O and S, and wherein in said second carbocyclic ring 1 or 2 —CH$_2$-groups may be optionally replaced by —N(R$^N$)—, —C(=O)—, —S(=O)— or —S(=O)$_2$—, and
 wherein each of said heteroaromatic ring and/or second carbocyclic ring independently of each other may be optionally substituted with one or more substituents selected from L$^{Ar}$; and
 wherein said heteroaromatic ring or said second carbocyclic ring are optionally substituted with a group R$^2$; and each R$^N$ is independently selected from the group R$^N$-G1 consisting of H, C$_{1-4}$-alkyl, C$_{1-4}$-alkyl-C(=O)—, and C$_{1-4}$-alkyl-S(=O)$_2$—; and HetAr is selected from the group HetAr-G1 consisting of a 5- or 6-membered heteroaromatic ring which contains 1, 2 or 3 heteroatoms independently of each other selected from N, NR$^N$, O and S;
 wherein each heteroaromatic ring may be optionally substituted with one or more substituents selected from L$^Q$; and Ar is selected from the group Ar-G1 consisting of
 a phenyl ring, a tetrazolyl ring, and a 5- or 6-membered heteroaromatic ring which contains 1, 2 or 3 heteroatoms independently of each other selected from N, NR$^N$, O and S; and wherein optionally a second carbocyclic ring is condensed to said phenyl ring or heteroaromatic ring, wherein said second carbocyclic ring is unsaturated or aromatic and 5- or 6-membered and may contain 1, 2 or 3 heteroatoms independently of each other selected from N, NR$^N$, O and S, and wherein in said second carbocyclic ring 1 or 2 —CH$_2$— groups are optionally replaced by —N(R$^N$)—, —C(=O)—, —S(=O)— or —S(=O)$_2$—, and
 wherein each of said phenyl ring, heteroaromatic ring and/or second carbocyclic ring independently of each other may be optionally substituted with one or more substituents selected from L$^{Ar}$; and wherein said phenyl ring, tetrazolyl ring, heteroaromatic ring or second carbocyclic ring are optionally substituted with a group T; and T is selected from the group T-G1 consisting of F, Cl, Br, I, CN, OH, NO$_2$, C$_{1-6}$-alkyl-, C$_{2-6}$-alkenyl-, C$_{2-6}$-alkynyl-, C$_{3-6}$-cycloalkyl, C$_{1-6}$-alkyl-O—, C$_{3-6}$-cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)—(R$^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, NR$^N$, O and S; and wherein heterocyclyl is a 4- to 7-membered unsaturated or saturated carbocyclic ring in which 1, 2, or 3 —CH$_2$-groups independently of each other are replaced by NR$^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from L$^{Ar}$; and R$^{NT1}$ is selected from the group R$^{NT1}$-G1 consisting of H, C$_{1-6}$-alkyl, C$_{3-6}$-cycloalkyl, C$_{1-6}$-alkyl-C(=O)—, C$_{1-6}$-alkyl-S(=O)$_2$, heterocyclyl, aryl and heteroaryl, wherein each alkyl and cylcoalkyl group may be optionally substituted with one or more substituents independently of each other selected from the group consisting of F, OH, CN, C$_{1-4}$-alkyl, C$_{1-4}$-alkyl-O—, (R$^N$)$_2$N, C$_{1-4}$-alkyl-S(=O)$_2$—, C$_{3-6}$-cycloalkyl, heterocyclyl, phenyl and heteroaryl; and wherein heterocyclyl is a C$_{4-7}$-cycloalkyl ring in which 1 or 2 —CH$_2$-groups independently of each other are replaced by NR$^N$, O, C(=O), S, S(=O) or S(=O)$_2$; and wherein heterocyclyl may be optionally substituted with one or more substituents independently of each other selected from F, C$_{1-4}$-alkyl, (R$^N$)$_2$N, OH and C$_{1-4}$-alkyl-O—; and wherein aryl is phenyl or naphthyl; and wherein heteroaryl is a 5- or 6-membered aromatic carbocyclic ring which contains 1, 2 or 3 heteroatoms independently of each other selected from N, NR$^N$, O and S; and wherein aryl, phenyl and heteroaryl may be optionally substituted with one or more substituents L$^{Ar}$; and R$^{NT2}$ is selected from the group R$^{NT2}$-G1 consisting of H and C$_{1-6}$-alkyl; or R$^{NT1}$ and R$^{NT2}$ are linked to form one group selected from the group R$^{NT1}$R$^{NT2}$-G1 consisting of a C$_{3-5}$-alkylene group, wherein 1 or 2 —CH$_2$-groups independently of each other are replaced by NR$^N$, O, C(=O), S, S(=O) or S(=O)$_2$; and which may be optionally substituted with one or more substituents independently of each other selected from F, C$_{1-4}$-alkyl, (R$^N$)$_2$N, OH and C$_{1-4}$-alkyl-O—;

L$^{Ar}$ is selected from the group L$^{Ar}$-G1 consisting of F, Cl, Br, I, CN, OH, NO$_2$, C$_{1-4}$-alkyl-, C$_{1-4}$-alkyl-O—, (R$^N$)$_2$N—C(=O), (R$^N$)$_2$N—, and C$_{1-4}$-alkyl-S(=O)$_2$—, wherein each alkyl group may be optionally substituted with one or more substituents independently of each other selected from F, Cl, CN, OH and C$_{1-3}$-alkyl-O—; and L$^P$ is selected from the group L$^P$-G1 consisting of F and C$_{1-3}$-alkyl, wherein the alkyl group may be substituted with one or more F-atoms; and L$^Q$ is selected from the group L$^Q$-G1 consisting of F, Cl, CN, OH, C$_{1-4}$-alkyl, C$_{3-7}$-cycloalkyl-, F$_2$HC—, F$_3$C—, C$_{1-4}$-alkyl-O—, F$_2$HC—O—, F$_3$C—O— and C$_{3-7}$-cycloalkyl-O—; and R$^2$ is selected from the group R$^2$-G1 consisting of F, Cl, Br, I, CN, OH, NO$_2$, C$_{1-6}$-alkyl-, C$_{2-6}$-alkenyl-, C$_{2-6}$-alkynyl-, C$_{3-6}$-cycloalkyl, C$_{1-6}$-alkyl-O—, C$_{3-6}$-cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)—(R$^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, NR$^N$, O and S; and wherein heterocyclyl is a 4- to 7-membered unsaturated or saturated carbocyclic ring in which 1, 2, or 3 —CH$_2$-groups independently of each other are replaced by NR$^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from L$^{Ar}$; and n is an integer selected from 0, 1, 2, 3, or 4;

including any tautomers and stereoisomers thereof, or a salt thereof or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^N$, HetAr, Ar, $R^2$, T, $R^{NT1}$, $R^{NT2}$, $L^{Ar}$, $L^P$, $L^Q$, and n are defined as above and hereinafter. If residues, substituents, or groups occur several times in a compound, as for example $R^N$, $L^{Ar}$, $L^P$, or $L^Q$, they may have the same or different meanings. Some preferred meanings of individual groups and substituents of the compounds according to the invention will be given hereinafter. Any and each of these definitions may be combined with each other.

$R^1$:

$R^1$-G1:

According to one embodiment, the group $R^1$ is selected from the group $R^1$-G1 as defined hereinbefore and hereinafter.

$R^1$-G2:

According to another embodiment the group $R^1$ is selected from the group $R^1$-G2 consisting of a 5-membered heteroaromatic ring which contains 2 or 3 heteroatoms independently of each other selected from N, $NR^N$, O and S and a 6-membered heteroaromatic ring which contains 1 or 2 N atoms; and wherein optionally a second carbocyclic ring is condensed to said 5- and 6-membered heteroaromatic rings, wherein said second carbocyclic ring is unsaturated or aromatic and 5- or 6-membered and may contain 1 or 2 heteroatoms independently of each other selected from N, $NR^N$, O and S, and wherein in said second carbocyclic ring 1 or 2 —$CH_2$— groups may be optionally replaced by —N($R^N$)—, —C(=O)— or —S(=O)$_2$—, and wherein each of said heteroaromatic ring and/or second carbocyclic ring independently of each other may be optionally substituted with one or two substituents selected from $L^{Ar}$; and wherein said heteroaromatic ring or said second carbocyclic ring are optionally substituted with a group $R^2$.

$R^1$-G3:

According to another embodiment the group $R^1$ is selected from the group $R^1$-G3 consisting of

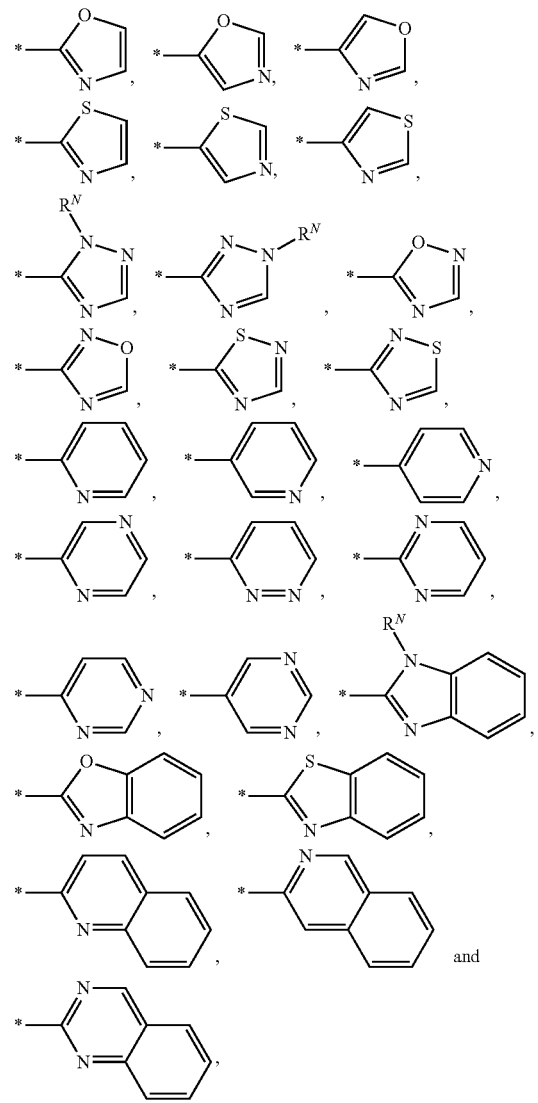

wherein each ring is optionally substituted with one substituent $L^{Ar}$ and each group is optionally substituted with one $R^2$.

$R^1$-G4:

According to another embodiment the group $R^1$ is selected from the group $R^1$-G4 consisting of

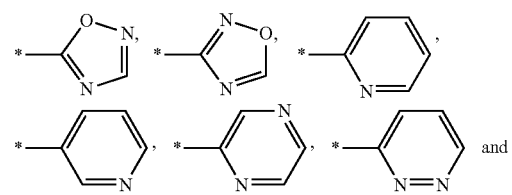

-continued

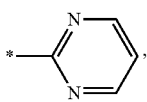

wherein each ring is optionally substituted with one $L^{Ar}$ and each group is optionally substituted with one $R^2$.

R$^1$-G5:

In another embodiment the group $R^1$ is selected from the group R$^1$-G5 consisting of

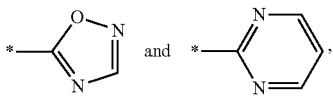

wherein each ring is optionally substituted with one $R^2$.

R$^1$-G5a:

In another embodiment the group $R^1$ is selected from the group R$^1$-G5a consisting of

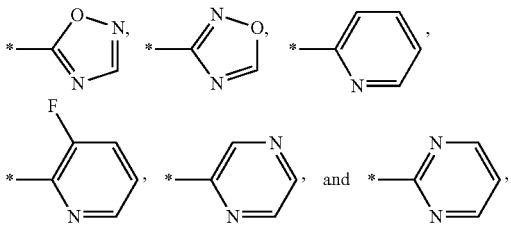

wherein each ring is optionally additionally substituted with one $R^2$.

R$^1$-G6:

In another embodiment the group $R^1$ is selected from the group R$^1$-G6 consisting of

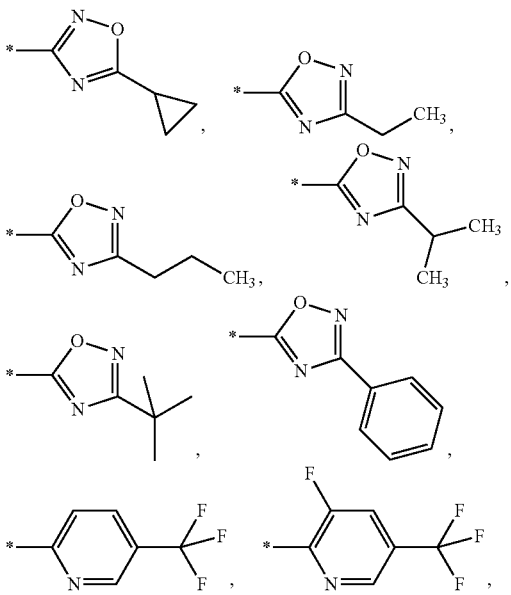

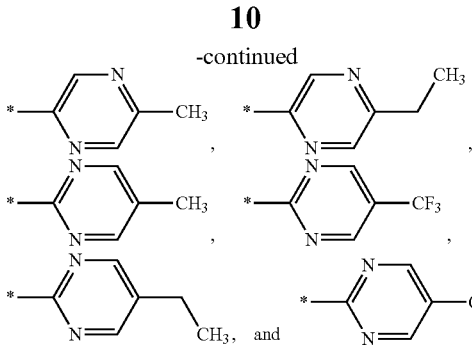

R$^1$-G7:

In another embodiment the group $R^1$ is selected from the group R$^1$-G7 consisting of,

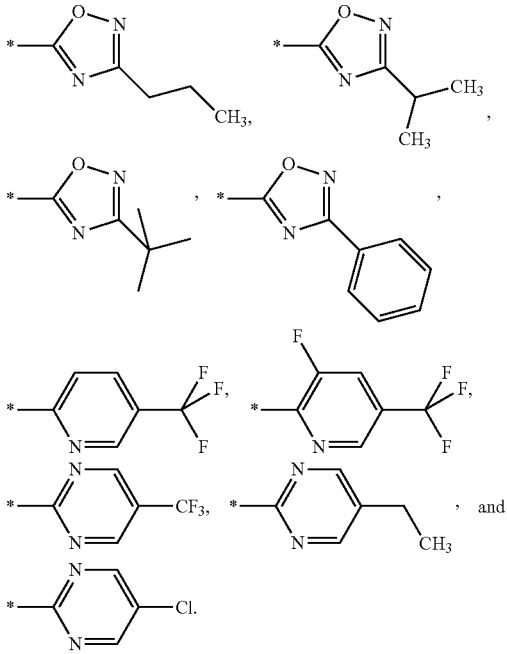

R$^N$

R$^N$-G1:

In one embodiment, the group $R^N$ is selected from the group R$^N$-G1 as defined hereinbefore and hereinafter.

R$^N$-G2:

In another embodiment the group $R^N$ is selected from the group R$^N$-G2 consisting of H, methyl, ethyl, isopropyl, methylcarbonyl, and methylsulfonyl.

R$^N$-G3:

In another embodiment the group $R^N$ is selected from the group R$^N$-G3 consisting of H, methyl, methylcarbonyl, and methylsulfonyl.

HetAr:

HetAr-G1:

In one embodiment, the group HetAr is selected from the group HetAr-G1 as defined hereinbefore and hereinafter.

HetAr-G1a:

In another embodiment the group HetAr is selected from the group HetAr-G1a consisting of pyridinylene, pyridazinylene, pyrimidinylene, pyrazinylene, furanylene, thiophenylene, imidazolylene, pyrazolylene, oxazolylene, isoxazloylene, thiazolylene, triazolylene, oxadiazolylene and thiadiazolylene.

HetAr-G1b:

In another embodiment the group HetAr is selected from the group HetAr-G1b consisting of pyridinylene, pyridazinylene, pyrimidinylene, pyrazinylene, imidazolylene, isoxazloylene and oxadiazolylene.

HetAr-G2:

In another embodiment the group HetAr is selected from the group HetAr-G2 consisting of

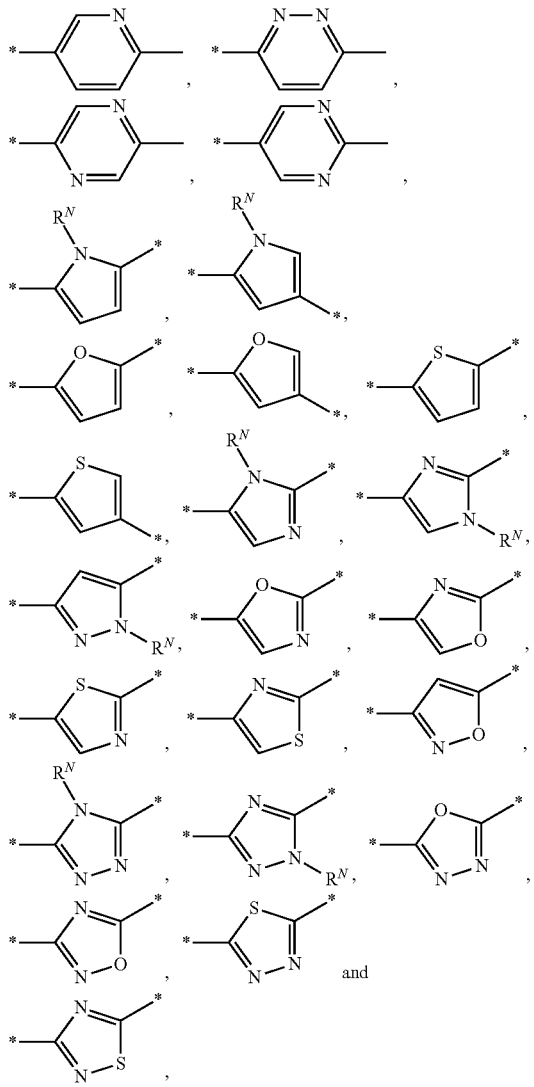

wherein each ring may be optionally substituted with one or two substituents independently of each other selected from $L^Q$.

HetAr-G2a:

In another embodiment the group HetAr is selected from the group HetAr-G2a consisting of

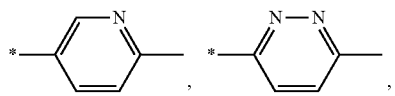

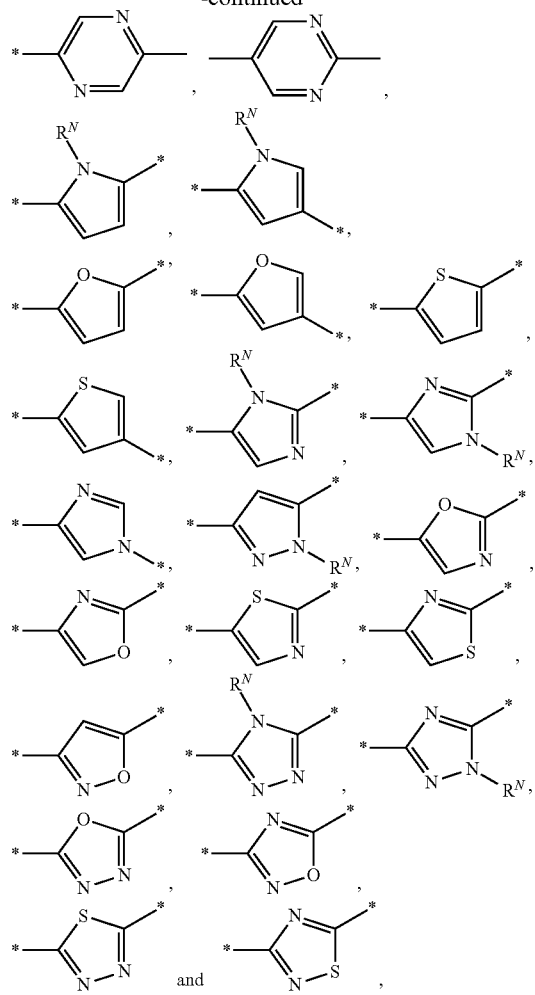

wherein each ring may be optionally substituted with one or two substituents independently of each other selected from $L^Q$.

HetAr-G3:

In another embodiment the group HetAr is selected from the group HetAr-G3 consisting of

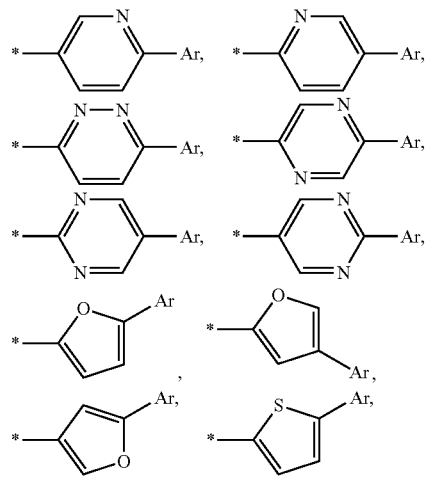

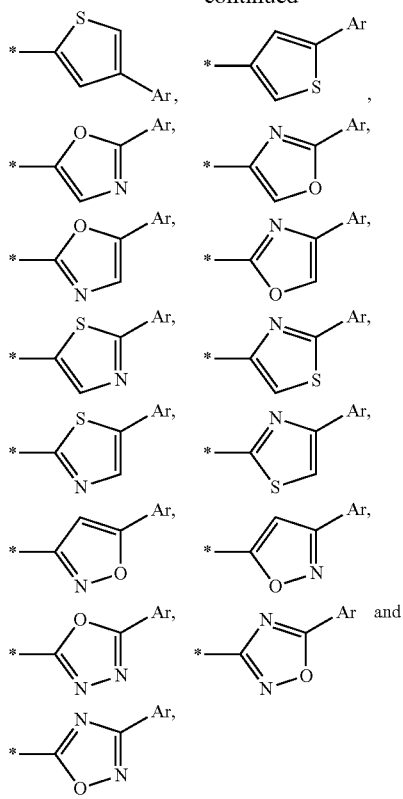

wherein the attachment points of the residues Ar and —C(=O)N(cPr)-(*) are explicitly indicated and wherein each ring may be optionally substituted with one or two substituents independently of each other selected from $L^Q$ and wherein Ar is as defined hereinbefore and hereinafter.

HetAr-G3a:

In another embodiment the group HetAr is selected from the group HetAr-G3a consisting of

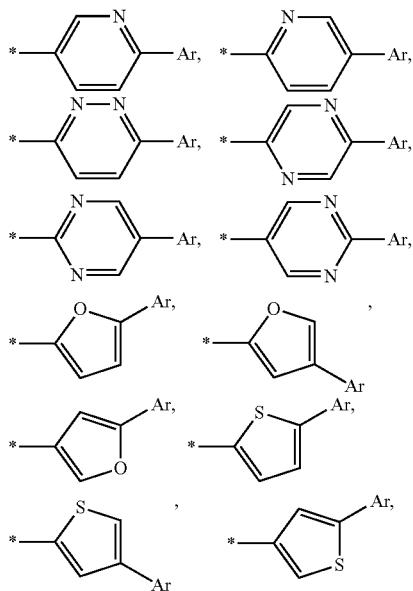

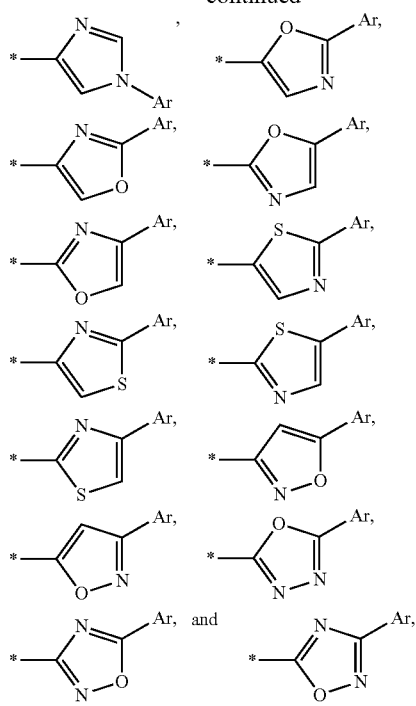

wherein the attachment points of the residues Ar and —C(=O)N(cPr)-(*) are explicitly indicated and wherein each ring may be optionally substituted with one or two substituents independently of each other selected from $L^Q$ and wherein Ar is as defined hereinbefore and hereinafter.

HetAr-G4:

In another embodiment the group HetAr is selected from the group HetAr-G4 consisting of wherein the attachment points of the residues Ar and —C(=O)N(cPr)-(*) are explicitly indicated and wherein each ring may be optionally substituted with one or two substituents independently of each other selected from $L^Q$ and wherein Ar is as defined hereinbefore and hereinafter.

HetAr-G4a:

In another embodiment the group HetAr is selected from the group HetAr-G4a consisting of

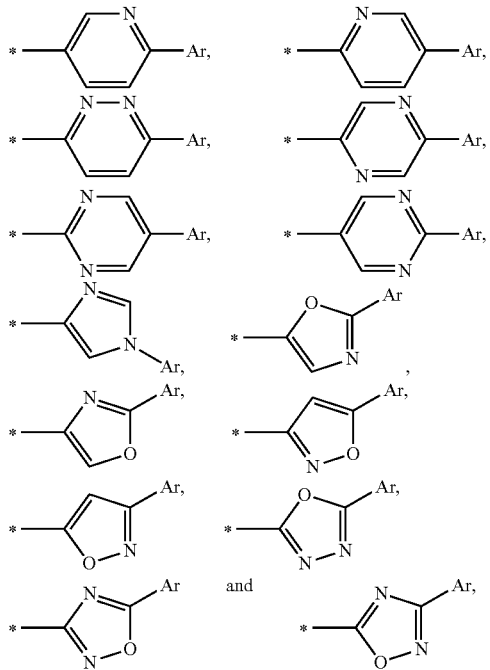

wherein the attachment points of the residues Ar and —C(=O)N(cPr)-(*) are explicitly indicated and wherein each ring may be optionally substituted with one substituent selected from $L^Q$ and
wherein Ar is as defined hereinbefore and hereinafter.
HetAr-G5:

In another embodiment the group HetAr is selected from the group HetAr-G5 consisting of

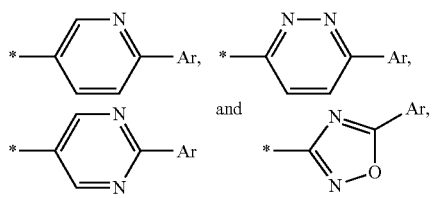

wherein the attachment points of the residues Ar and —C(=O)N(cPr)-(*) are explicitly indicated and wherein each 6-membered heteroaromatic ring is optionally substituted with one substituent selected from $L^Q$ and
wherein Ar is as defined hereinbefore and hereinafter.
HetAr-G5a:

In another embodiment the group HetAr is selected from the group HetAr-G5a consisting of

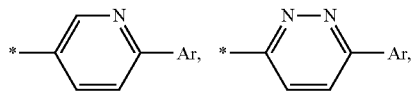

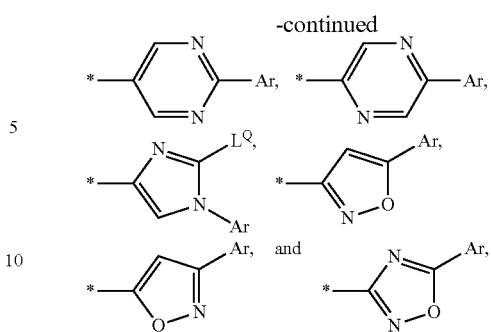

wherein the attachment points of the residues Ar and —C(=O)N(cPr)-(*) are explicitly indicated:
and wherein $L^Q$ is H or $CH_3$ and
wherein Ar is as defined hereinbefore and hereinafter.
HetAr-G5b:

In another embodiment the group HetAr is selected from the group HetAr-G5b consisting of

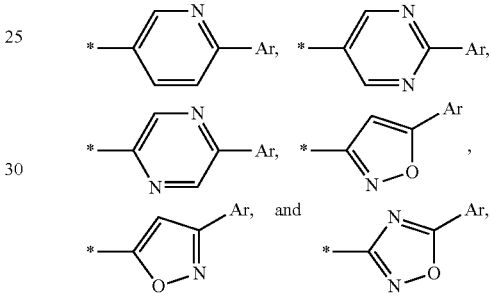

wherein the attachment points of the residues Ar and —C(=O)N(cPr)-(*) are explicitly indicated; and
wherein Ar is as defined hereinbefore and hereinafter.
Ar:
Ar-G1:

In one embodiment, the group Ar is selected from the group Ar-G1 as defined hereinbefore and hereinafter.
Ar-G2:

In another embodiment the group Ar is selected from the group Ar-G2 consisting of a phenyl ring, a 6-membered heteroaromatic ring which contains 1 or 2 N-atoms, and a 5-membered heteroaromatic ring which contains 1, 2 or 3 heteroatoms independently of each other selected from N, $NR^N$, O and S; and wherein optionally a second carbocyclic ring is condensed to said phenyl ring or said heteroaromatic ring, wherein said second carbocyclic ring is unsaturated or aromatic and is 5- or 6-membered and may optionally contain 1 or 2 heteroatoms independently of each other selected from N, $NR^N$, O and S, and wherein in said second carbocyclic ring 1 or 2 —$CH_2$-groups are optionally replaced by —N($R^N$)—, —C(=O)—, —S(=O)— or —S(=O)$_2$—, and wherein each of said phenyl ring, heteroaromatic ring and second carbocyclic ring may be optionally substituted independently of each other with one or more substituents selected from $L^{Ar}$; and wherein said phenyl ring, heteroaromatic ring or second carbocyclic ring are optionally substituted with a group T.
Ar-G2a:

In another embodiment the group Ar is selected from the group Ar-G2a consisting of a phenyl ring, a 6-membered heteroaromatic ring which contains 1 or 2 N-atoms and a 5-membered heteroaromatic ring which contains 1, 2 or 3 heteroatoms independently of each other selected from N, $NR^N$, O and S; wherein said phenyl ring or heteroaromatic ring is optionally substituted with a group T, and wherein said phenyl ring and heteroaromatic ring may be optionally substituted with one or more substituents independently of each other selected from $L^{Ar}$.

Ar-G2b:

In another embodiment the group Ar is selected from the group Ar-G2b consisting of a phenyl ring, a 5-membered heteroaromatic ring which contains 2 or 3 heteroatoms independently of each other selected from N, $NR^N$, O or S, and a 6-membered heteroaromatic ring which contains 1 or 2 N atoms; and wherein a second carbocyclic ring is condensed to said phenyl ring or said heteroaromatic ring, wherein said second carbocyclic ring is unsaturated or aromatic and is 5- or 6-membered and may optionally contain 1 or 2 heteroatoms independently of each other selected from N, $NR^N$, O and S, and wherein in said second carbocyclic ring 1 or 2 —$CH_2$-groups are optionally replaced by —$N(R^N)$—, —C(=O)—, —S(=O)— or —$S(=O)_2$—, and wherein each of said phenyl ring, heteroaromatic ring and second carbocyclic ring may be optionally substituted with one or more substituents independently of each other selected from $L^{Ar}$; and wherein said phenyl ring, heteroaromatic ring or second carbocyclic ring are optionally substituted with a group T.

Ar-G2c:

In another embodiment the group Ar is selected from the group Ar-G2c consisting of a phenyl ring, a tetrazolyl ring, a 6-membered heteroaromatic ring which contains 1 or 2 N-atoms and a 5-membered heteroaromatic ring which contains 1, 2 or 3 heteroatoms independently of each other selected from N, $NR^N$, O and S;

wherein said phenyl ring, tetrazolyl ring, and heteroaromatic ring are optionally substituted with a group T, and wherein said phenyl ring and heteroaromatic ring are optionally substituted with one or more substituents independently of each other selected from $L^{Ar}$.

Ar-G3:

In another embodiment the group Ar is selected from the group Ar-G3 consisting of the cyclic groups phenyl, pyridinyl, pyrazinyl, pyridazinyl, pyrimidinyl, isoxazolyl, oxazolyl, oxadiazolyl, imidazolyl, pyrazolyl, triazolyl, thienyl and thiazolyl, and wherein optionally a second carbocyclic ring is condensed to said cyclic groups, wherein said second carbocyclic ring is selected from the group consisting of cyclopentene, cyclohexene, dihydropyrrole, tetrahydropyridine, tetrahydropyrazine, dihydrooxazine, dihydrofuran, dihydropyran, [1,3]dioxol, dihydrodioxine, dihydropyrimidine, dihydropyrazine, dihydropyridazine, benzene, pyridine, pyrimidine, pyrazine, pyridazine, oxazole, triazole and thiazole, wherein in said second carbocyclic ring 1 or 2 —$CH_2$-groups are optionally replaced by —C(=O)—, and wherein in said cyclic groups and/or second carbocyclic ring the H-atom in one or more —NH-groups is replaced independently of each other by the substituent $R^N$, wherein each of the beforementioned rings may be optionally substituted with one or more substituents independently of each other selected from $L^{Ar}$, and wherein said cyclic group or second carbocyclic ring is optionally substituted with a group T.

Ar-G3a:

In another embodiment the group Ar is selected from the group Ar-G3a consisting of a phenyl and a heteroaromatic ring selected from pyridinyl, pyrazinyl, pyridazinyl, pyrimidinyl, isoxazolyl, oxazolyl, oxadiazolyl, imidazolyl, pyrazolyl, triazolyl, thienyl and thiazolyl, wherein said phenyl and heteroaromatic ring may be optionally substituted with one or more substituents independently of each other selected from $L^{Ar}$, and wherein said phenyl or heteroaromatic ring are optionally substituted with a group T and wherein in said heteroaromatic ring the H-atom in one NH group is optionally replaced by $R^N$.

Ar-G3b:

In another embodiment the group Ar is selected from the group Ar-G3b consisting of a phenyl and a heteroaromatic ring selected from pyridinyl, pyrazinyl, pyridazinyl, pyrimidinyl, isoxazolyl, oxazolyl, imidazolyl, pyrazolyl, pyrrolyl, thienyl, thiazolyl and triazolyl ring, and wherein a second carbocyclic ring is condensed to said phenyl or heteroaromatic ring, wherein said second carbocyclic ring is selected from the group consisting of cyclopentene, cyclohexene, dihydropyrrole, pyrrole, tetrahydropyridine, tetrahydropyrazine, dihydrooxazine, dihydrofuran, dihydropyran, [1,3]dioxol, dihydrodioxine, dihydropyrimidine, dihydropyrazine, dihydropyridazine, benzene, pyridine, pyrimidine, pyrazine, pyridazine, oxazole, triazole and thiazole, wherein in said second carbocyclic ring 1 or 2 —$CH_2$-groups are optionally replaced by —C(=O)—, and wherein in said heteroaromatic ring and/or second carbocyclic ring the H-atom in one or more —NH-groups are optionally independently of one another replaced by $R^N$, wherein each of the beforementioned rings may be optionally substituted with one or more substituents independently of each other selected from $L^{Ar}$, and wherein said phenyl ring, heteroaromatic ring or second carbocyclic ring are optionally substituted with a group T.

Ar-G3c:

In another embodiment the group Ar is selected from the group Ar-G3c consisting of a phenyl, a tetrazolyl, and a heteroaromatic ring selected from pyridinyl, pyrazinyl, pyridazinyl, pyrimidinyl, isoxazolyl, oxazolyl, oxadiazolyl, imidazolyl, pyrazolyl, triazolyl, thienyl and thiazolyl, wherein said phenyl and heteroaromatic ring are optionally substituted with one or more substituents independently of each other selected from $L^{Ar}$, and wherein said phenyl, tetrazolyl and heteroaromatic ring are optionally substituted with a group T and wherein in heteroaromatic ring the H-atom in one NH group is optionally replaced by $R^N$.

Ar-G4:

In another embodiment the group Ar is selected from the group Ar-G4 consisting of the cyclic groups phenyl, pyridyl, pyrazinyl, pyridazinyl, pyrimidinyl, isoxazolyl, oxazolyl, imidazolyl, pyrazolyl, thienyl, thiazolyl, [1,2,3]triazolyl, [1,2,4]triazolyl, [1,2,4]triazolo[1,5-a]pyridinyl, benzooxazolyl, benzothiazolyl, indolyl, 2,3-dihydro-indolyl, quinoxalinyl, quinolinyl, 3H-quinazolin-4-onyl, 2,3-dihydro-benzo[1,4]dioxinyl, isoindole-1,3-dionyl, 1,3-dihydro-indol-2-onyl, 1H-indazolyl, and indanyl, wherein in the beforementioned groups in one or more —NH-groups the H-atom are optionally independently of one another replaced by $R^N$, and wherein each ring may be optionally substituted with one or more substituents independently of each other selected from $L^{Ar}$, and wherein the beforementioned cyclic groups are optionally substituted with a group T.

Ar-G4a:

In another embodiment the group Ar is selected from the group Ar-G4a consisting of the cyclic groups phenyl, pyridyl, pyrazinyl, pyridazinyl, pyrimidinyl, isoxazolyl, oxazolyl, imidazolyl, pyrazolyl, thienyl, thiazolyl, [1,2,3]triazolyl, [1,2,4]triazolyl, tetrazolyl, [1,2,4]triazolo[1,5-a]pyridinyl, benzooxazolyl, benzothiazolyl, indolyl, 2,3-dihydro-indolyl, quinoxalinyl, quinolinyl, 3H-quinazolin-4-onyl, 2,3-dihydro-benzo[1,4]dioxinyl, isoindole-1,3-dionyl, 1,3-dihydro-indol-2-onyl, 1H-indazolyl, and indanyl, wherein in the beforementioned groups in one or more —NH-groups the H-atom are optionally independently of one another replaced by $R^N$, and wherein each ring having 0 to 3 heteroatoms is optionally substituted with one or more substituents independently of each other selected from $L^{Ar}$, and wherein the beforementioned cyclic groups are optionally substituted with a group T.

Ar-G4b:

In another embodiment the group Ar is selected from the group Ar-G4b consisting of the cyclic groups phenyl, pyridyl, oxazolyl, imidazolyl, [1,2,4]triazolyl and tetrazolyl, wherein each of the beforementioned cyclic groups is optionally substituted with one or two substituents independently of each other selected from the group consisting of F, CN, $CH_2CN$, $CH_3$, $CH_2CH_3$, $OCH_2CH_3$, and $SO_2CH_3$.

Ar-G5:

In another embodiment the group Ar is selected from the group Ar-G5 consisting of:

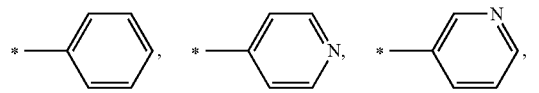

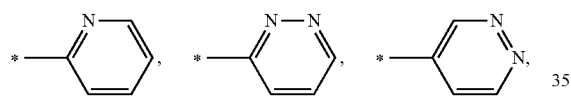

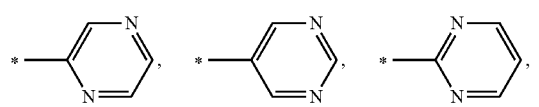

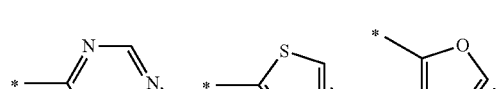

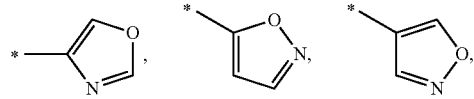

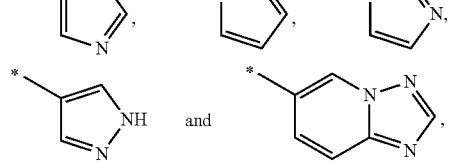

wherein in the above groups a H-atom in a —NH-group is optionally replaced by $R^N$, and wherein each group is not substituted with a group T or is substituted with a group T, and each ring may be optionally substituted with one or more substituents independently of each other selected from $L^{Ar}$, and wherein the groups T and $L^{Ar}$ are defined as hereinbefore and hereinafter.

Ar-G5a:

In another embodiment the group Ar is selected from the group Ar-G5a consisting of:

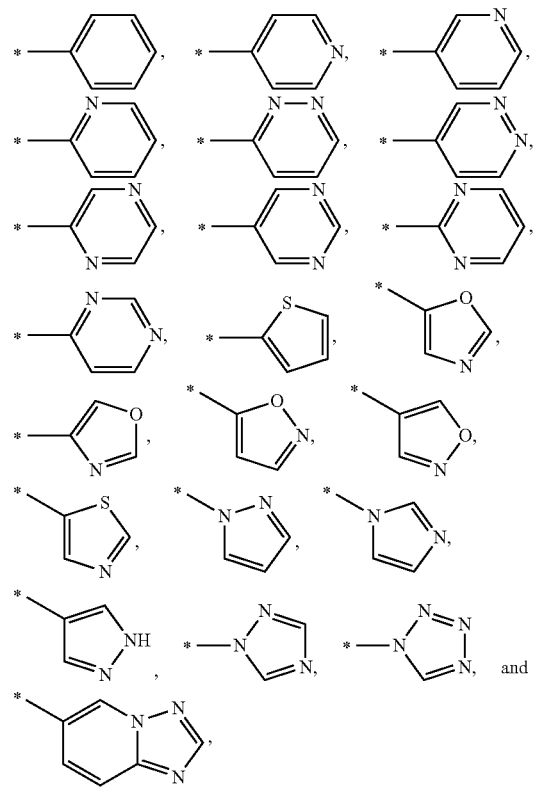

wherein in the above groups a H-atom in a —NH-group is optionally replaced by $R^N$, and wherein each group is not substituted with a group T or is substituted with a group T, and each ring having 0 to 3 heteroatoms is optionally substituted with one or more substituents independently of each other selected from $L^{Ar}$, and wherein the groups T and $L^{Ar}$ are defined as hereinbefore and hereinafter.

Ar-G5b:

In another embodiment the group Ar is selected from the group Ar-G5b consisting of:

wherein each of the beforementioned groups is optionally substituted with one substituent selected from the group consisting of CN, $CH_2CN$, $CH_3$, $CH_2CH_3$, $OCH_2CH_3$, and $SO_2CH_3$ and may additionally be substituted with one F atom.

Ar-G6:
In another embodiment the group Ar is selected from the group Ar-G6 consisting of:
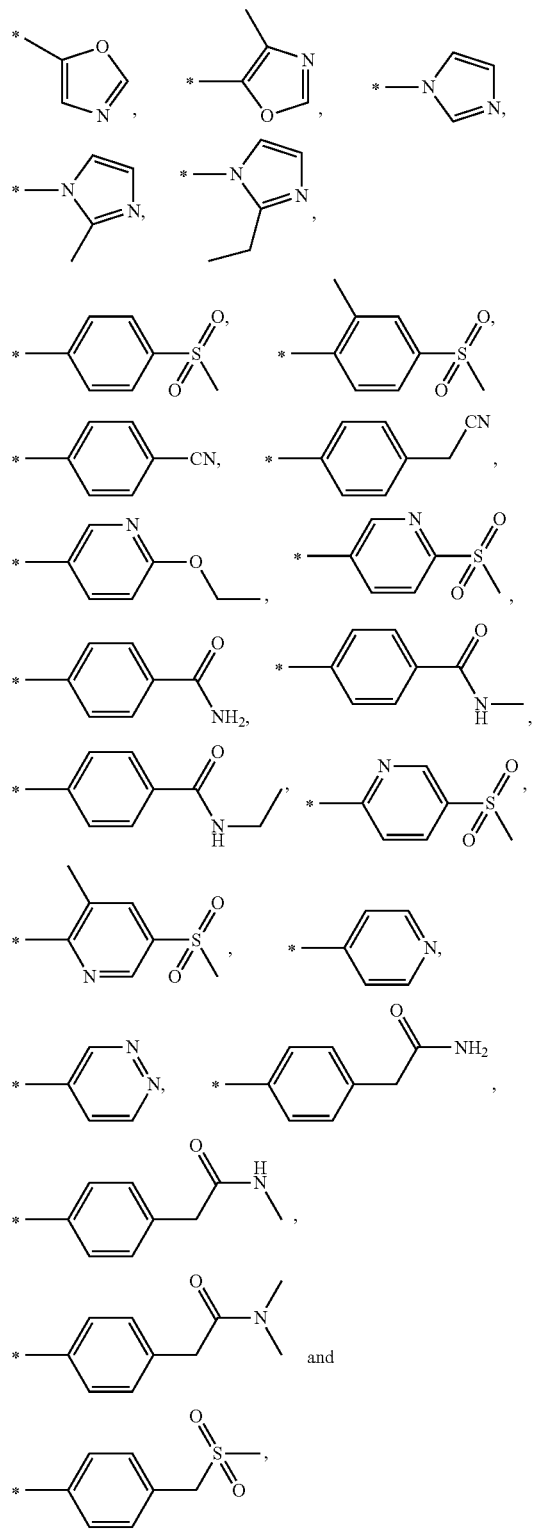
wherein the phenyl and pyridine rings may optionally be additionally substituted with one or two F atoms.
Ar-G6a:
In another embodiment the group Ar is selected from the group Ar-G6a consisting of:
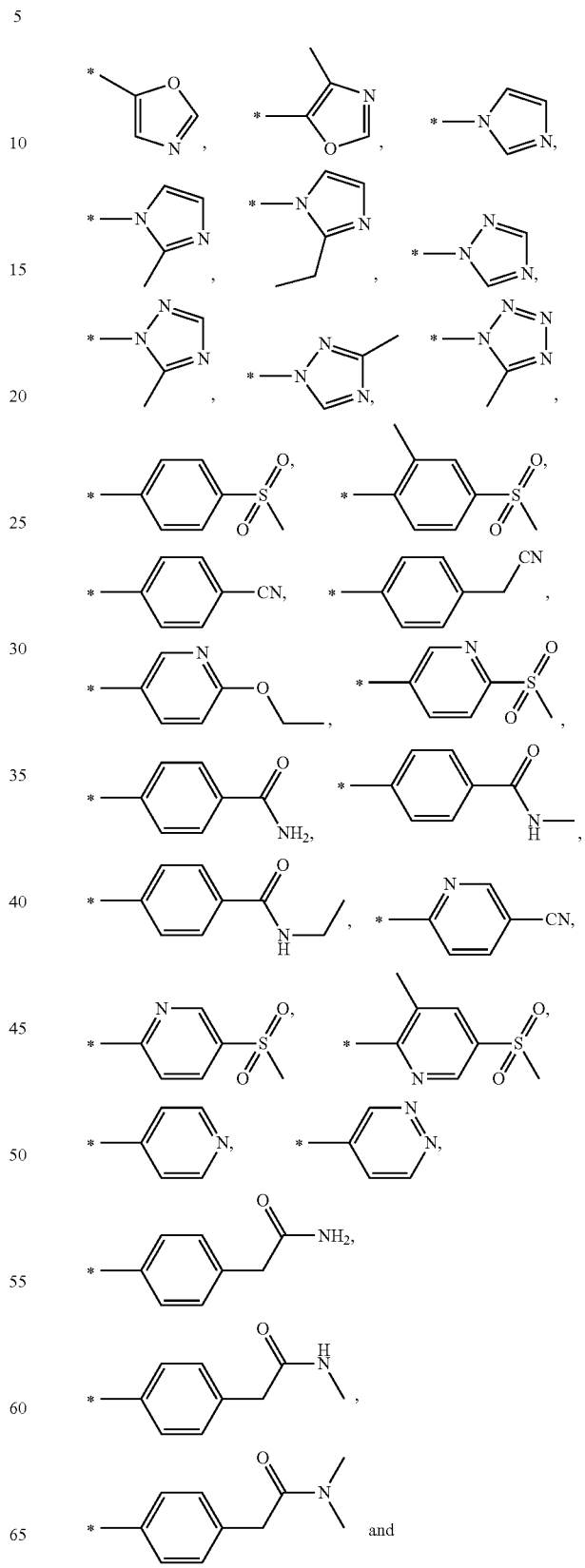

-continued

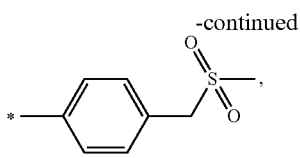

wherein the phenyl and pyridine rings are optionally additionally substituted with one or two F atoms.

Ar-G7:

In another embodiment the group Ar is selected from the group Ar-G7 consisting of:

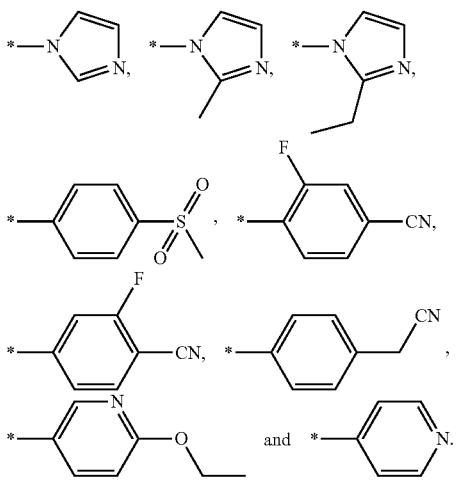

Ar-G7a:

In another embodiment the group Ar is selected from the group Ar-G7a consisting of:

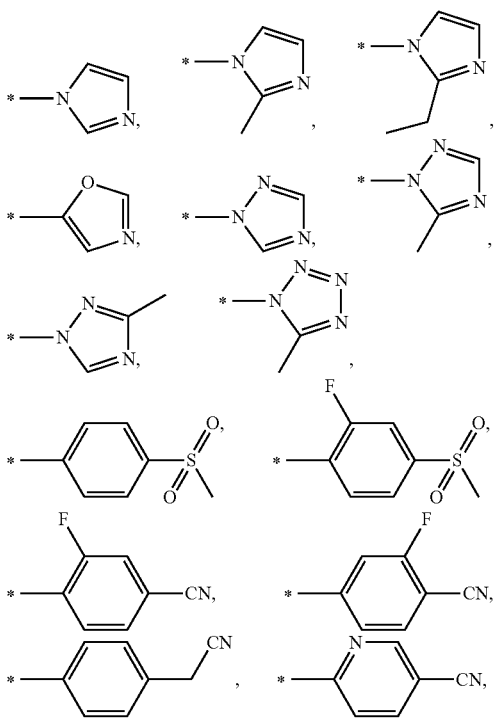

-continued

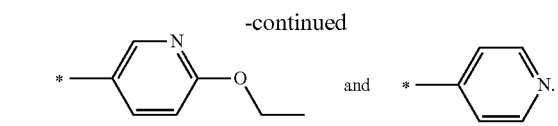

Ar-G7b:

In another embodiment the group Ar is selected from the group Ar-G7b consisting of:

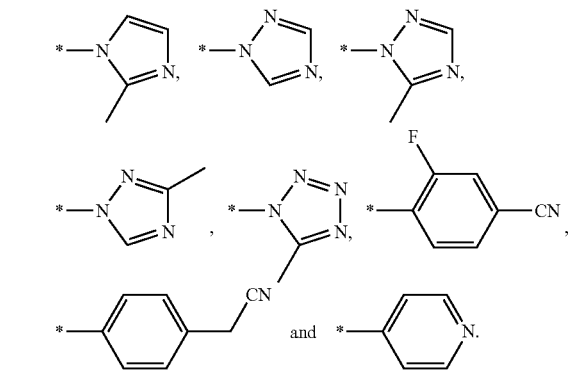

T

T-G1:

According to one embodiment, the group T is selected from the group T-G1 as defined hereinbefore and hereinafter.

T-G2:

According to another embodiment the group T is selected from the group T-G2 consisting of F, Cl, Br, ON, OH, $C_{1-4}$-alkyl-, $C_{1-4}$-alkyl-O—, $C_{1-4}$-alkyl-O—C(=O)—, $C_{1-4}$-alkyl-C(=O)—, $C_{1-4}$-alkyl-S(=O), $C_{1-4}$-alkyl-S(=O)$_2$, $R^{NT1}R^{NT2}$N—C(=O)—, $R^{NT1}R^{NT2}$N—S(=O)$_2$—, $R^{NT1}R^{NT2}$N, wherein each alkyl group may be optionally substituted with one or more substituents independently of each other selected from F, Cl, CN, OH, phenyl, heteroaryl, and heterocyclyl, wherein heteroaryl is selected from the group consisting of pyridinyl, pyrimidinyl, pyridazinyl, pyrazinyl, pyrazolyl, imidazolyl, [1,2,4]triazolyl and tetrazolyl; and wherein heterocyclyl is selected from the group consisting of azetidinyl, pyrrolidinyl, piperidinyl, piperazinyl and morpholinyl, wherein in each of the beforementioned groups a —CH$_2$-group may be replaced by a group selected from —C(=O)— and —S(=O)$_2$—, and wherein each of the beforementioned groups may be optionally substituted with one or more substituents independently of each other selected from $C_{1-3}$-alkyl; and wherein phenyl and heteroaryl may be optionally substituted independently of each other with one or more substituents $L^{Ar}$;

and in addition the group T-G2 consists of $R^{NT1}R^{NT2}$N—C(=O)—$C_{1-4}$-alkyl- and $C_{1-4}$-alkyl-S(=O)$_2$—$C_{1-4}$-alkyl-.

T-G3:

According to another embodiment the group T is selected from the group T-G3 consisting of CN, $C_{1-3}$-alkyl-, NC—$C_{1-3}$-alkyl-, $C_{1-3}$-alkyl-O—, $C_{1-3}$-alkyl-S(=O), $C_{1-3}$-alkyl-S(=O)$_2$, $R^{NT1}R^{NT2}$N—S(=O)$_2$—, $R^{NT1}R^{NT2}$N—C(=O)—, $R^{NT1}R^{NT2}$N—, $C_{1-3}$-alkyl-S(=O)$_2$—CH$_2$—, and $R^{NT1}R^{NT2}$N—C(=O)—CH$_2$—.

T-G3a:

According to another embodiment the group T is selected from the group T-G3a consisting of CN, $C_{1-3}$-alkyl-, NC—$C_{1-3}$-alkyl-, $C_{1-3}$-alkyl-O—, $C_{1-3}$-alkyl-S(=O)$_2$.

T-G4:

According to another embodiment the group T is selected from the group T-G4 consisting of CN, —CH$_3$, —CH$_2$CH$_3$, NC—CH$_2$—, —O—CH$_2$CH$_3$ and H$_3$C—S(=O)$_2$—.

$R^{NT1}$ $R^{NT1}$-G1:

In one embodiment, $R^{NT1}$ is selected from the group $R^{NT1}$-G1 as defined hereinbefore and hereinafter.

$R^{NT1}$-G2:

In another embodiment $R^{NT1}$ is selected from the group $R^{NT1}$-G2 consisting of H, $C_{1-3}$-alkyl, $C_{3-6}$-cycloalkyl, $C_{1-4}$-alkyl-C(=O)— and $C_{1-4}$-alkyl-S(=O)$_2$—, wherein each alkyl and cylcoalkyl group may be optionally substituted with one or more substituents independently of each other selected from the group consisting of F, OH, $C_{1-3}$-alkyl-O— and $(R^N)_2$N.

$R^{NT1}$-G3:

In another embodiment $R^{NT1}$ is selected from the group $R^{NT1}$-G3 consisting of H, $C_{1-3}$-alkyl, $C_{1-3}$-alkyl-C(=O)— and $C_{1-3}$-alkyl-S(=O)$_2$—.

$R^{NT2}$ $R^{NT2}$-G1:

In one embodiment, $R^{NT2}$ is selected from the group $R^{NT2}$-G1 as defined hereinbefore and hereinafter.

$R^{NT2}$-G2:

In another embodiment $R^{NT2}$ is selected from the group $R^{NT2}$-G2 consisting of H and $C_{1-3}$-alkyl.

$R^{NT1}R^{NT2}$ $R^{NT1}R^{NT2}$-G1:

According to another embodiment the groups $R^{NT1}$ and $R^{NT2}$ are linked and form a group which is selected from the group $R^{NT1}R^{NT2}$-G1 as defined hereinbefore and hereinafter.

$R^{NT1}R^{NT2}$-G2:

According to another embodiment the groups $R^{NT1}$ and $R^{NT2}$ are linked and together with the N-atom to which they are attached form a group which is selected from the group $R^{NT1}R^{NT2}$-G2 consisting of azetidinyl, pyrrolidinyl, piperidinyl, morpholinyl, piperazinyl, piperazin-2-onyl, N—$C_{1-3}$-alkyl-piperazinyl, N—$C_{1-3}$-alkyl-piperazin-2-onyl, and N—($C_{1-3}$-alkyl-C(=O))-piperazinyl, which may be optionally substituted with one or more substituents independently of each other selected from the group consisting of F, OH, $C_{1-3}$-alkyl, $C_{1-3}$-alkyl-O—, and $(R^N)_2$N.

$L^{Ar}$:

$L^{Ar}$-G1:

In one embodiment, the group $L^{Ar}$ is selected from the group $L^{Ar}$-G1 as defined hereinbefore and hereinafter.

$L^{Ar}$-G2:

In another embodiment the group $L^{Ar}$ is selected from the group $L^{Ar}$-G2 consisting of F, Cl, Br, I, CN, OH, $C_{1-3}$-alkyl-, $C_{1-3}$-alkyl-O—, H$_2$N—, $C_{1-3}$-alkyl-NH— and $(C_{1-3}$-alkyl)$_2$N—, wherein the $C_{1-3}$-alkyl- and $C_{1-3}$-alkyl-O— group may be optionally substituted with one or more F-atoms.

$L^{Ar}$-G3:

In another embodiment the group $L^{Ar}$ is selected from the group $L^{Ar}$-G3 consisting of F, CN, OH, H$_3$O—, F$_3$C—, HF$_2$C—, H$_3$C—O—, HF$_2$C—O— and F$_3$C—O—.

$L^{Ar}$-G4:

In to the embodiment $L^{Ar}$-G4, the group $L^{Ar}$ is F.

$R^2$:

$R^2$-G1:

According to one embodiment, the group $R^2$ is selected from the group $R^2$-G1 as defined hereinbefore and hereinafter.

$R^2$-G2:

According to another embodiment the group $R^2$ is selected from the group $R^2$-G2 consisting of F, Cl, Br, I, ON, OH, $C_{1-6}$-alkyl-, $C_{2-6}$-alkenyl-, $C_{2-6}$-alkynyl-, $C_{3-6}$-cycloalkyl, $C_{1-6}$-alkyl-O—, $C_{3-6}$-cycloalkyl-O—, $C_{1-6}$-alkyl-S—, $C_{1-6}$-alkyl-O—C(=O)—, $C_{1-4}$-alkyl-S(=O)—, $C_{1-4}$-alkyl-S(=O)$_2$—, $R^{NT1}R^{NT2}$N—, $R^{NT1}R^{NT2}$N—C(=O)—, $R^{NT1}R^{NT2}$N—S(=O)$_2$—, heterocyclyl, heterocyclyl-O—, phenyl and heteroaryl, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, phenyl, heteroaryl, and heterocyclyl, and wherein heteroaryl is selected from the group consisting of pyridinyl, pyrimidinyl, pyridazinyl, pyrazinyl, pyrazolyl, imidazolyl, thiazolyl, and thienyl; and wherein heterocyclyl is selected from the group consisting of pyrrolidin-2-onyl, piperidin-2-onyl, piperazin-2-onyl, morpholinyl, morpholin-3-onyl, oxetanyl, tetrahydrofuranyl, and tetrahydropyranyl, each of which may be optionally substituted with one or two substituents independently of each other selected from $C_{1-3}$-alkyl; and wherein phenyl and heteroaryl may be optionally substituted with one or more substituents independently of each other selected from $L^{Ar}$;

and in addition the group $R^2$-G2 consists of $C_{1-4}$-alkyl-S(=O)—$C_{1-4}$-alkyl-, $C_{1-4}$-alkyl-S(=O)$_2$—$C_{1-4}$-alkyl-, $R^{NT1}R^{NT2}$N—$C_{1-3}$-alkyl-, $R^{NT1}R^{NT2}$N—S(=O)$_2$—$C_{1-4}$-alkyl-, and $R^{NT1}R^{NT2}$N—C(=O)—$C_{1-4}$-alkyl-.

$R^2$-G3:

According to another embodiment the group $R^2$ is selected from the group $R^2$-G3 consisting of F, Cl, CN, $C_{1-6}$-alkyl-, $C_{3-6}$-cycloalkyl, $C_{1-6}$-alkyl-O—, $C_{3-6}$-cycloalkyl-O—, $C_{1-4}$-alkyl-S(=O)—, $C_{1-4}$-alkyl-S(=O)$_2$—, $R^{NT1}R^{NT2}$N—, $R^{NT1}R^{NT2}$N—$C_{1-3}$-alkyl-, $R^{NT1}R^{NT2}$N—C(=O)—, $R^{NT1}R^{NT2}$N—S(=O)$_2$—, $R^{NT1}R^{NT2}$N—C(=O)—$C_{1-4}$-alkyl-, heterocyclyl, heterocyclyl-O—, phenyl and heteroaryl, wherein each alkyl and cycloalkyl group may be optionally substituted with one or more substituents independently of each other selected from F, H$_3$C—, HO—, H$_3$C—O—, phenyl, and heterocyclyl, and wherein heteroaryl is selected from the group consisting of pyridinyl, pyrimidinyl, pyridazinyl, and pyrazinyl; and wherein heterocyclyl is selected from the group consisting of oxetanyl, tetrahydrofuranyl and tetrahydropyranyl, each of which may be optionally substituted with one or two H$_3$C— groups; and wherein phenyl and heteroaryl are optionally substituted with one substituent $L^{Ar}$.

$R^2$-G4:

According to another embodiment the group $R^2$ is selected from the group $R^2$-G4 consisting of F, NC—, $C_{1-4}$-alkyl-, F$_3$C—, $C_{1-3}$-alkyl-O— and phenyl, wherein the phenyl ring is optionally monosubstituted with F, Cl, CH$_3$, or OCH$_3$.

R²-G5:
According to another embodiment the group R² is selected from the group R²-G5 consisting of F, Cl, $C_{1-4}$-alkyl-, cyclopropyl, $F_3C-$, and phenyl.

$L^P$:
$L^P$-G1:
In one embodiment, the group $L^P$ is selected from the group $L^P$-G1 as defined hereinbefore and hereinafter.
$L^P$-G2:
In another embodiment the group $L^P$ is selected from the group $L^P$-G2 consisting of F and methyl.
$L^P$-G3:
According to the embodiment $L^P$-G3, the group $L^P$ is F.

$L^Q$:
$L^Q$-G1:
In one embodiment, the group $L^Q$ is selected from the group $L^Q$-G1 as defined hereinbefore and hereinafter.
$L^Q$-G2:
In another embodiment the group $L^Q$ is selected from the group $L^Q$-G2 consisting of F, CN, OH, $H_3C-$, $F_2HC-$, $F_3C-$, $H_3C-O-$, $F_2HC-O-$ and $F_3C-O-$.
$L^Q$-G3:
In another embodiment the group $L^Q$ is selected from the group $L^Q$-G3 consisting of F and $H_3C-$.
$L^Q$-G4:
According to the embodiment $L^Q$-G4, the group $L^Q$ is $H_3C-$.

n:
The index n is an integer selected from 0, 1, 2, 3 or 4.
According to another embodiment the index n is 0, 1 or 2.
According to one embodiment the index n is 1 or 2, in particular 1.
According to another embodiment the index n is 0 or 1.
According to another embodiment the index n is 1.
According to another embodiment the index n is 0.

The following preferred embodiments of compounds of the formula I are described using generic formulae I.1 to I.5, wherein any tautomers and stereoisomers, solvates, hydrates and salts thereof, in particular the pharmaceutically acceptable salts thereof, are encompassed.

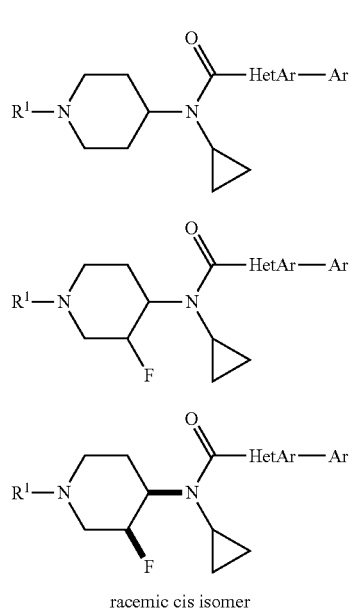

racemic cis isomer

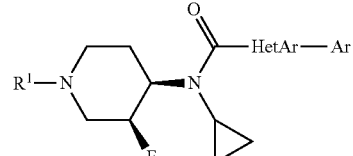

I.4

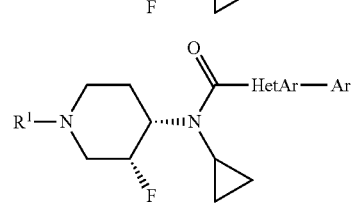

I.5 wherein the groups $R^1$, HetAr, and Ar are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | R¹ | Ar | HetAr | $L^P$ | n |
|---|---|---|---|---|---|
| E-1 | R¹-G1 | Ar-G1 | HetAr-G1 | $L^P$-G2 | 1 or 0 |
| E-2 | R¹-G2 | Ar-G2c | HetAr-G1a | $L^P$-G2 | 1 or 0 |
| E-3 | R¹-G2 | Ar-G2c | HetAr-G1b | $L^P$-G2 | 1 or 0 |
| E-4 | R¹-G2 | Ar-G2c | HetAr-G2a | $L^P$-G2 | 1 or 0 |
| E-5 | R¹-G3 | Ar-G2a | HetAr-G2 | $L^P$-G2 | 1 or 0 |
| E-6 | R¹-G3 | Ar-G3a | HetAr-G2 | $L^P$-G2 | 1 or 0 |
| E-7 | R¹-G2 | Ar-G2a | HetAr-G4 | $L^P$-G2 | 1 or 0 |
| E-8 | R¹-G2 | Ar-G2a | HetAr-G5 | $L^P$-G2 | 1 or 0 |
| E-9 | R¹-G2 | Ar-G3a | HetAr-G4 | $L^P$-G2 | 1 or 0 |
| E-10 | R¹-G2 | Ar-G3a | HetAr-G5 | $L^P$-G2 | 1 or 0 |
| E-11 | R¹-G3 | Ar-G3a | HetAr-G4 | $L^P$-G2 | 1 or 0 |
| E-12 | R¹-G3 | Ar-G3a | HetAr-G5 | $L^P$-G2 | 1 or 0 |
| E-13 | R¹-G4 | Ar-G3a | HetAr-G2 | $L^P$-G2 | 1 or 0 |
| E-14 | R¹-G4 | Ar-G3a | HetAr-G4 | $L^P$-G2 | 1 or 0 |
| E-15 | R¹-G4 | Ar-G3a | HetAr-G5 | $L^P$-G2 | 1 or 0 |
| E-16 | R¹-G4 | Ar-G3c | HetAr-G2a | $L^P$-G2 | 1 or 0 |
| E-17 | R¹-G4 | Ar-G3c | HetAr-G4a | $L^P$-G2 | 1 or 0 |
| E-18 | R¹-G4 | Ar-G3c | HetAr-G5a | $L^P$-G2 | 1 or 0 |
| E-19 | R¹-G4 | Ar-G4a | HetAr-G2a | $L^P$-G2 | 1 or 0 |
| E-20 | R¹-G4 | Ar-G4a | HetAr-G4a | $L^P$-G2 | 1 or 0 |
| E-21 | R¹-G4 | Ar-G4b | HetAr-G4a | $L^P$-G3 | 1 or 0 |
| E-22 | R¹-G4 | Ar-G4a | HetAr-G5a | $L^P$-G2 | 1 or 0 |
| E-23 | R¹-G4 | Ar-G5a | HetAr-G2a | $L^P$-G2 | 1 or 0 |
| E-24 | R¹-G4 | Ar-G5a | HetAr-G4a | $L^P$-G2 | 1 or 0 |
| E-25 | R¹-G4 | Ar-G4a | HetAr-G5a | $L^P$-G2 | 1 or 0 |
| E-26 | R¹-G4 | Ar-G4b | HetAr-G5a | $L^P$-G3 | 1 or 0 |
| E-27 | R¹-G4 | Ar-G6a | HetAr-G4a | $L^P$-G2 | 1 or 0 |
| E-28 | R¹-G4 | Ar-G7a | HetAr-G4a | $L^P$-G2 | 1 or 0 |
| E-29 | R¹-G5a | Ar-G3c | HetAr-G2a | $L^P$-G2 | 1 or 0 |
| E-30 | R¹-G5a | Ar-G3c | HetAr-G4a | $L^P$-G2 | 1 or 0 |
| E-31 | R¹-G5a | Ar-G3c | HetAr-G5a | $L^P$-G2 | 1 or 0 |
| E-32 | R¹-G5a | Ar-G4a | HetAr-G2a | $L^P$-G2 | 1 or 0 |
| E-33 | R¹-G5a | Ar-G4a | HetAr-G4a | $L^P$-G2 | 1 or 0 |
| E-34 | R¹-G5a | Ar-G4a | HetAr-G5a | $L^P$-G2 | 1 or 0 |
| E-35 | R¹-G5a | Ar-G4b | HetAr-G5b | $L^P$-G3 | 1 or 0 |
| E-36 | R¹-G5a | Ar-G4a | HetAr-G5b | $L^P$-G3 | 1 or 0 |
| E-37 | R¹-G5a | Ar-G5a | HetAr-G2a | $L^P$-G2 | 1 or 0 |
| E-38 | R¹-G5a | Ar-G5a | HetAr-G4a | $L^P$-G2 | 1 or 0 |
| E-39 | R¹-G5a | Ar-G5a | HetAr-G5a | $L^P$-G2 | 1 or 0 |
| E-40 | R¹-G5a | Ar-G6a | HetAr-G2a | $L^P$-G2 | 1 or 0 |
| E-41 | R¹-G5a | Ar-G6a | HetAr-G4a | $L^P$-G2 | 1 or 0 |
| E-42 | R¹-G5a | Ar-G6a | HetAr-G4b | $L^P$-G3 | 1 or 0 |
| E-43 | R¹-G5a | Ar-G6a | HetAr-G5a | $L^P$-G2 | 1 or 0 |
| E-44 | R¹-G5a | Ar-G7a | HetAr-G2a | $L^P$-G2 | 1 or 0 |
| E-45 | R¹-G5a | Ar-G7a | HetAr-G4a | $L^P$-G2 | 1 or 0 |
| E-46 | R¹-G5a | Ar-G7a | HetAr-G5a | $L^P$-G2 | 1 or 0 |
| E-47 | R¹-G5a | Ar-G7b | HetAr-G5a | $L^P$-G3 | 1 or 0 |

-continued

| Embodiment | R¹ | Ar | HetAr | L^P | n |
|---|---|---|---|---|---|
| E-48 | R¹-G6 | Ar-G3c | HetAr-G2a | L^P-G2 | 1 or 0 |
| E-49 | R¹-G6 | Ar-G3c | HetAr-G4a | L^P-G2 | 1 or 0 |
| E-50 | R¹-G6 | Ar-G3c | HetAr-G5a | L^P-G2 | 1 or 0 |
| E-51 | R¹-G6 | Ar-G4a | HetAr-G2a | L^P-G2 | 1 or 0 |
| E-52 | R¹-G6 | Ar-G4a | HetAr-G4a | L^P-G2 | 1 or 0 |
| E-53 | R¹-G6 | Ar-G4a | HetAr-G5a | L^P-G2 | 1 or 0 |
| E-54 | R¹-G6 | Ar-G5a | HetAr-G2a | L^P-G2 | 1 or 0 |
| E-55 | R¹-G6 | Ar-G5a | HetAr-G4a | L^P-G2 | 1 or 0 |
| E-56 | R¹-G6 | Ar-G5a | HetAr-G4b | L^P-G3 | 1 or 0 |
| E-57 | R¹-G6 | Ar-G5a | HetAr-G5a | L^P-G2 | 1 or 0 |
| E-58 | R¹-G6 | Ar-G5a | HetAr-G5b | L^P-G2 | 1 or 0 |
| E-59 | R¹-G6 | Ar-G6a | HetAr-G2a | L^P-G2 | 1 or 0 |
| E-60 | R¹-G6 | Ar-G6a | HetAr-G4a | L^P-G2 | 1 or 0 |
| E-61 | R¹-G6 | Ar-G6a | HetAr-G5a | L^P-G2 | 1 or 0 |
| E-62 | R¹-G6 | Ar-G7a | HetAr-G2a | L^P-G2 | 1 or 0 |
| E-63 | R¹-G6 | Ar-G7a | HetAr-G4a | L^P-G2 | 1 or 0 |
| E-64 | R¹-G6 | Ar-G7a | HetAr-G5a | L^P-G2 | 1 or 0 |
| E-65 | R¹-G6 | Ar-G7b | HetAr-G5a | L^P-G3 | 1 or 0 |
| E-66 | R¹-G7 | Ar-G3c | HetAr-G2a | L^P-G3 | 1 or 0 |
| E-67 | R¹-G7 | Ar-G3c | HetAr-G5a | L^P-G3 | 1 or 0 |
| E-68 | R¹-G7 | Ar-G4a | HetAr-G4a | L^P-G3 | 1 or 0 |
| E-69 | R¹-G7 | Ar-G4b | HetAr-G5a | L^P-G3 | 1 or 0 |
| E-70 | R¹-G7 | Ar-G4a | HetAr-G5b | L^P-G3 | 1 or 0 |
| E-71 | R¹-G7 | Ar-G5a | HetAr-G4a | L^P-G3 | 1 or 0 |
| E-72 | R¹-G7 | Ar-G5a | HetAr-G5a | L^P-G3 | 1 or 0 |
| E-73 | R¹-G7 | Ar-G5a | HetAr-G5b | L^P-G3 | 1 or 0 |
| E-74 | R¹-G7 | Ar-G6a | HetAr-G4a | L^P-G3 | 1 or 0 |
| E-75 | R¹-G7 | Ar-G6a | HetAr-G5a | L^P-G3 | 1 or 0 |
| E-76 | R¹-G7 | Ar-G7a | HetAr-G4a | L^P-G3 | 1 or 0 |
| E-77 | R¹-G7 | Ar-G7a | HetAr-G5a | L^P-G3 | 1 or 0 |
| E-78 | R¹-G7 | Ar-G7b | HetAr-G5b | L^P-G3 | 0 or 1 |

Another embodiment concerns those compounds of formula I, wherein
R¹ is selected from a group consisting of

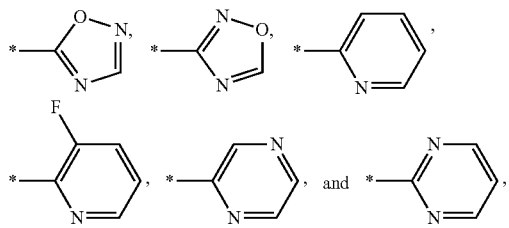

wherein R¹ is optionally substituted with Cl, $C_{1-4}$-alkyl-, cyclopropyl, $F_3C-$, or phenyl,
HetAr-Ar is selected from a group consisting of

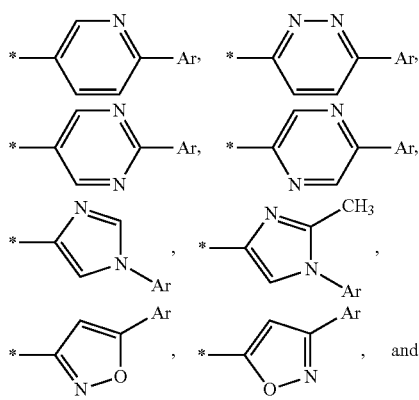

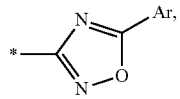

wherein Ar is selected from a group consisting of

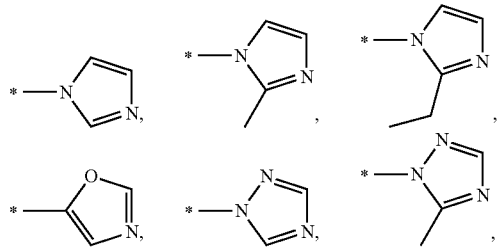

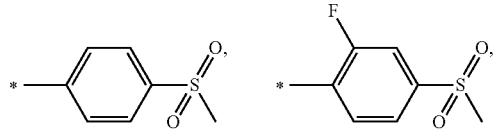

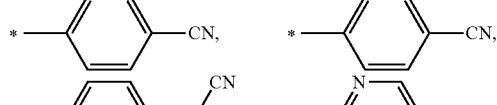

$L^P$ is F and n is 0 or 1.
Another embodiment concerns those compounds of formula I, wherein
R¹ is selected from a group consisting of

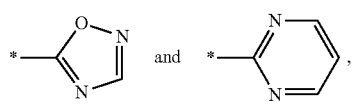

wherein R¹ may optionally be substituted with $C_{1-4}$-alkyl or phenyl,
HetAr-Ar is selected from a group consisting of

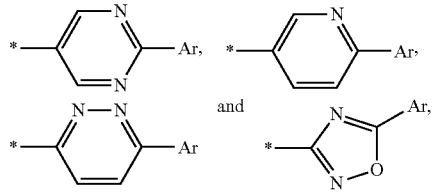

wherein Ar is selected from a group consisting of

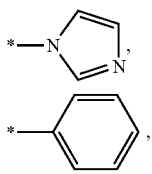

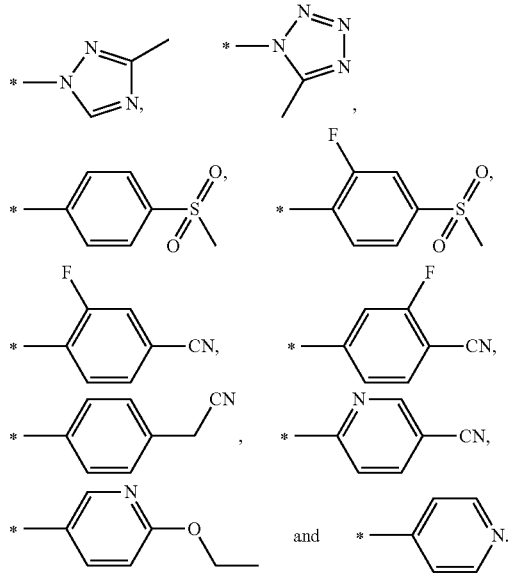

and wherein Ar may optionally be substituted with one or two substituents selected from a group consisting of —F, —CN, $C_{1-3}$-alkyl, $C_{1-3}$-alkyl-O—, $H_3C$—$SO_2$— and —$CH_2$—CN, and n is 0.

Another embodiment concerns those compounds of formula I.1, wherein $R^1$ is selected from a group consisting of

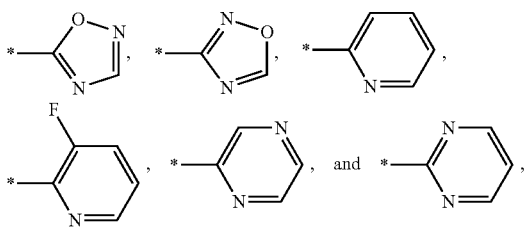

wherein $R^1$ is optionally substituted with Cl, $C_{1-4}$-alkyl-, cyclopropyl, $F_3C$—, or phenyl; and HetAr-Ar is selected from a group consisting of

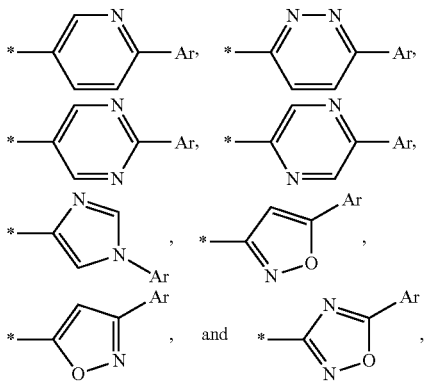

wherein Ar is selected from a group consisting of

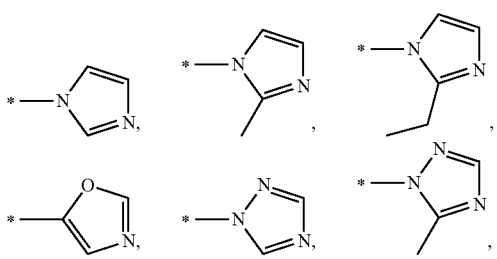

Another embodiment concerns those compounds of formula I.2 wherein $R^1$ is selected from a group consisting of

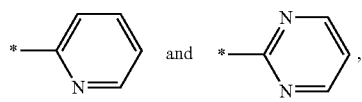

wherein $R^1$ is optionally substituted with Cl, $C_{1-3}$-alkyl or $F_3C$—; and HetAr-Ar is selected from a group consisting of

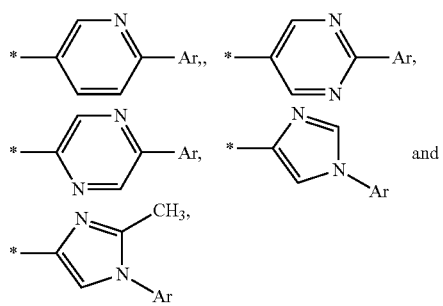

wherein Ar is selected from a group consisting of

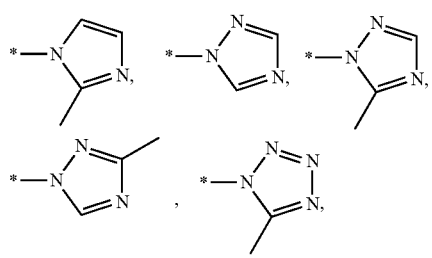

-continued
Particularly preferred compounds, including their tautomers and stereoisomers, the salts thereof, or any solvates or hydrates thereof, are described in the experimental section hereinafter.
The following compounds are mentioned as preferred examples of compounds according to the invention:
| Example No. | Structure |
| --- | --- |
| 27 | 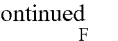 |
| 30 | 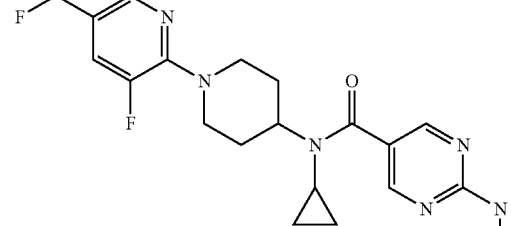 |
| 45 | 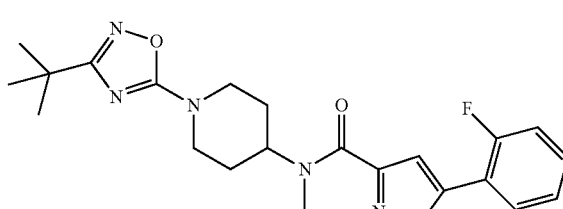 |
| 46 | 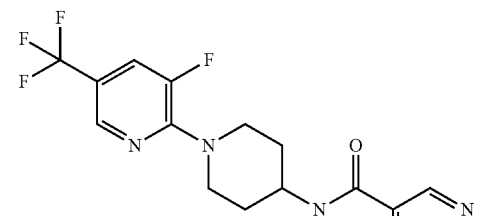 |

| Example No. | Structure |
|---|---|
| 49 | (structure) |
| 54 | (structure) |
| 60 | (structure) |
| 77 | (structure) |
| 78 | (structure) |

| Example No. | Structure |
|---|---|
| 79 | 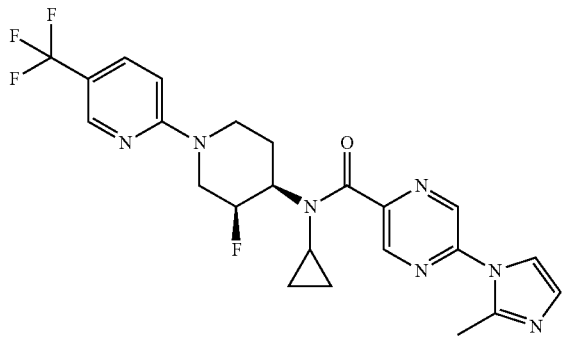 [SMILES: Cc1nccn1-c1cnc(C(=O)N(C2CC2)[C@@H]2CCN(c3ccc(C(F)(F)F)cn3)C[C@@H]2F)cn1] |
| 83 | 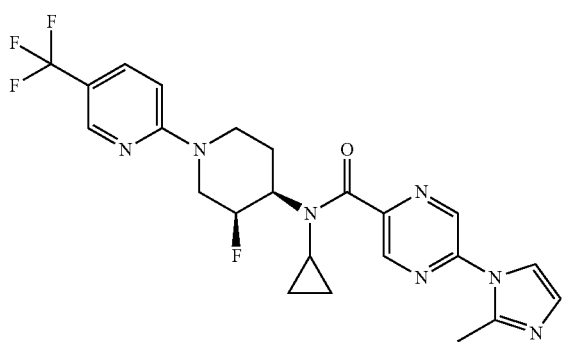 [SMILES: Cc1nccn1-c1cnc(C(=O)N(C2CC2)[C@@H]2CCN(c3ccc(C(F)(F)F)cn3)C[C@@H]2F)cn1] |
| 84 | 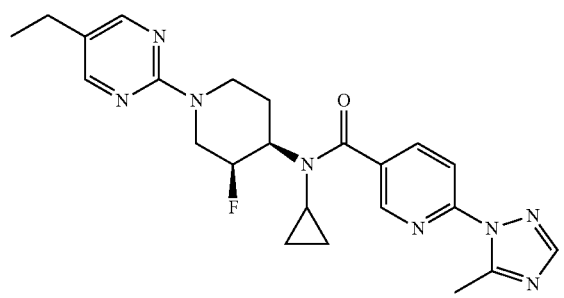 [SMILES: CCc1cnc(N2CC[C@@H](N(C(=O)c3ccc(-n4ncnc4C)nc3)C3CC3)[C@@H](F)C2)nc1] |
| 85 | 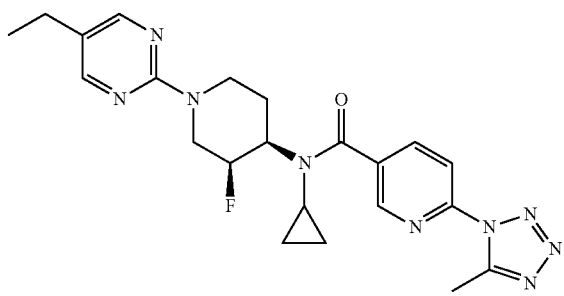 [SMILES: CCc1cnc(N2CC[C@@H](N(C(=O)c3ccc(-n4nnnc4C)nc3)C3CC3)[C@@H](F)C2)nc1] |
| 86 | 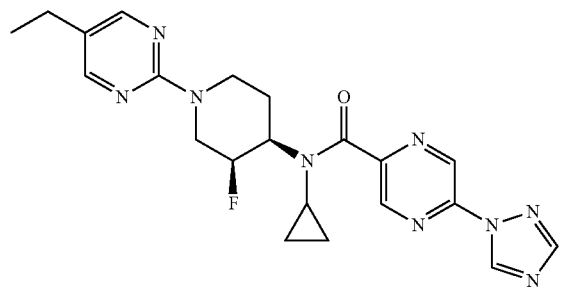 [SMILES: CCc1cnc(N2CC[C@@H](N(C(=O)c3cnc(-n4cncn4)cn3)C3CC3)[C@@H](F)C2)nc1] |

| Example No. | Structure |
|---|---|
| 87 | 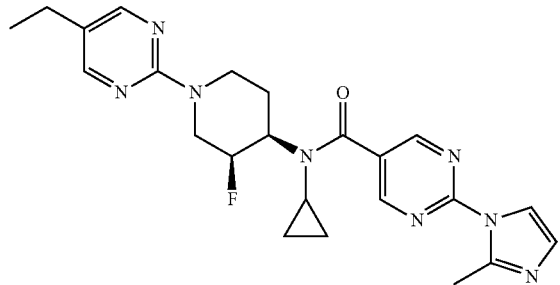 [SMILES: CCc1cnc(N2CC[C@@H](N(C(=O)c3cnc(-n4ccnc4C)nc3)C3CC3)[C@@H](F)C2)nc1] |
| 89 | 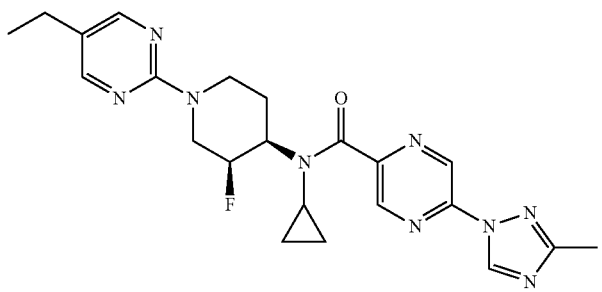 [SMILES: CCc1cnc(N2CC[C@@H](N(C(=O)c3cnc(-n4cnc(C)n4)cn3)C3CC3)[C@@H](F)C2)nc1] |
| 94 | 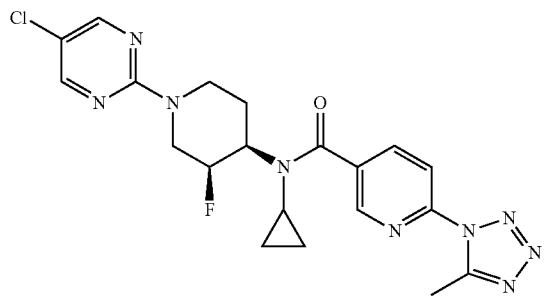 [SMILES: Cc1nnnn1-c1ccc(C(=O)N(C2CC2)[C@@H]2CCN(c3ncc(Cl)cn3)C[C@@H]2F)cn1] |
| 95 | 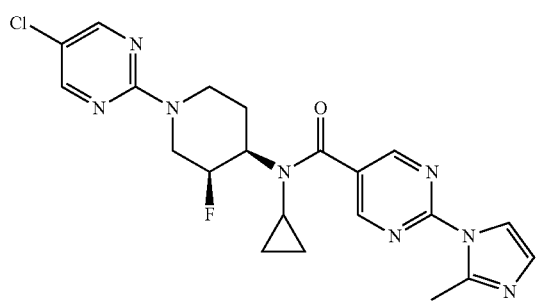 [SMILES: Cc1nccn1-c1ncc(C(=O)N(C2CC2)[C@@H]2CCN(c3ncc(Cl)cn3)C[C@@H]2F)cn1] |
| 98 | 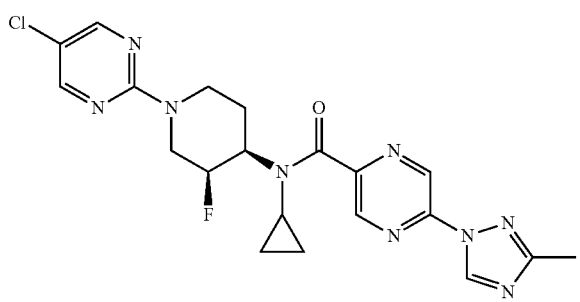 [SMILES: Cc1ncn(-c2cnc(C(=O)N(C3CC3)[C@@H]3CCN(c4ncc(Cl)cn4)C[C@@H]3F)cn2)n1] |

| Example No. | Structure |
|---|---|
| 99 | 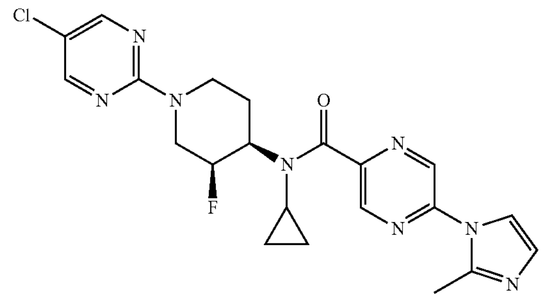 [SMILES: Cc1nccn1-c1cnc(C(=O)N(C2CC2)[C@@H]2CCN(c3ncc(Cl)cn3)C[C@@H]2F)cn1] |
| 101 | | including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I can principally be assembled from the building blocks 1 to 5 as sketched in Scheme 1; $R^1$, $L^P$, n, and Ar have the meanings as defined hereinbefore and hereinafter. Building blocks 1 to 5 are either known compounds that are commercially available or of which a synthesis is reported or can be synthesized in analogy to proceedings described herein or in the literature for related compounds. The order of linking the building blocks is variable and the most effective way depends on the precise decoration of the building blocks and the reactivity of the groups to be linked and may vary for each of them. In principle, almost each order of linking is conceivable, however, combining building block 1 with building block 2 followed by attachment of building block 3 and finally compound 4, optionally already bearing building block 5, is preferred in most of the cases. For varying one individual residue or for the synthesis of particular target compounds a deviating proceeding may be more appropriate.

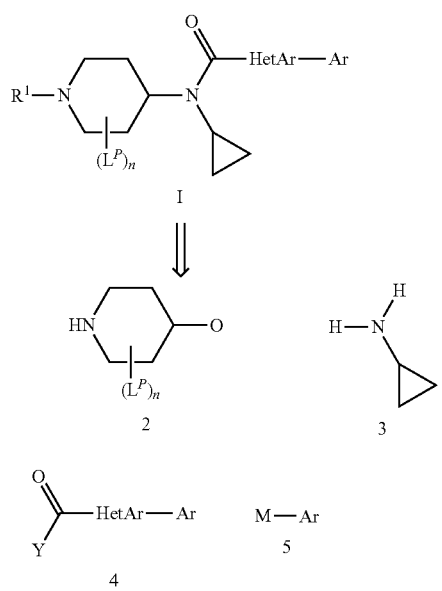

Scheme 1

$X^1$, $X^2$, Y = leaving group
M = metal or pseudo-metal group

A general way of attaching residue $R^1$ to the N atom of the piperidine of the compounds of the invention (I) or an intermediate towards them is sketched in Scheme 2; $R^1$, $L^P$, and n have the meanings as defined hereinbefore and hereinafter.

The reaction may be conducted as a classical nucleophilic substitution on a heteroaromatic bearing a leaving group, such as F, Cl, Br, $SO_2C_{1-4}$-alkyl, $SO_2$aryl, and $NO_2$. The reaction partners are preferably coupled in the presence of a rather mild base, e.g. $Na_2CO_3$, $K_2CO_3$, or $Cs_2CO_3$, pyridine, 4-dimethylaminopyridine, triethylamine, ethyldiisopropylamine, 1,8-diazabicylo[5.4.0]undec-7-ene, in toluene, tetrahydrofuran, 1,4-dioxane, 1,2-dimethoxyethane, acetonitrile, N,N-dimethylformamide, N,N-dimethylacetamide, N-methylpyrrolidinone, water, methanol, ethanol, isopropanol, dimethyl sulfoxide, or mixtures thereof, at 20 to 220° C. by conventional or microwave heating. Alternatively, the piperidine 2' may be transformed into the corresponding metal piperidide by deprotonation with a strong base, e.g. butyl lithium, NaH, or KH, prior to the addition of the electrophile 1'. In certain cases the use of transition metals as catalysts for the coupling may be beneficial or even essential. The leaving group X in compound 1' is then preferably Cl, Br, I, $OSO_2CH_3$, $OSO_2$tolyl, and $OSO_2CF_3$. The reactions are preferably conducted with a transition metal derived catalyst which is preferably based on copper or palladium. The catalyst may be an elemental form of the transition metal, such as palladium on charcoal or nanoparticles of palladium, a salt of the transition metal, such as CuCl, CuBr, CuI, $Cu(O_3SCF_3)_2$, $Cu(O_2CCH_3)_2$, $PdCl_2$, $PdBr_2$, $Pd(O_2CCH_3)_2$, and $Pd(O_2CCF_3)_2$, or a complex of the transition metal, such $Pd_2$(dibenzylideneacetone)$_3$, all of which may optionally be combined with additional ligands, such as phosphines, e.g. triphenylphosphine, tritolylphosphine, tri-cyclohexylphosphine, tri-tert-butylphosphine, 1,1'-bis(diphenylphosphino)ferrocene, optionally substituted biphenyl-di-tert-butylphosphines or biphenyl-dicyclohexyl-phosphines, 2,2'-bis(diphenylphosphinyl)-1,1'-binaphthyl, 1,3-disubstituted imidazole or imidazolidine carbenes, phosphites, 1,3-diketones, nitriles, or alkenes. The coupling reaction is preferably conducted in the presence of a base, such as NaOtBu, KOtBu, $LiN(SiMe_3)_2$, $K_2CO_3$, $Cs_2CO_3$, or $K_3PO_4$, in toluene, benzene, tetrahydrofuran, 1,4-dioxane, 1,2-dimethoxyethane, N,N-dimethylformamide, N,N-dimethylacetamide, N-methylpyrrolidinone, dimethyl sulfoxide, tBuOH, or mixtures thereof, at 0 to 180° C.

Alternatively, particular residues $R^1$ in compound 6 or any other intermediate towards compound I or compound I itself, such as [1,2,4]oxadiazoles and [1,2,4]triazoles, may be assembled from the corresponding cyanamide of compound 2' or another corresponding intermediate and N-hydroxyamidine or N-aminoamidine, respectively, as described, for example, in the experimental part.

Scheme 2

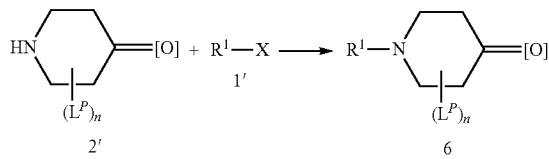

[O] = O or protective group for =O, e.g., $OCH_2CH_2O$
X = leaving group, e.g., F, Cl, Br, I, $OSO_2CF_3$, $OSO_2C_{1-4}$-alkyl, $OSO_2$-aryl, $SO_2C_{1-4}$-alkyl, $NO_2$ The linkage between the piperidine and the cyclopropylamine fragment is preferably established via reductive amination from a piperidinone, such as 6', and cyclopropyl-amine (3) (Scheme 3); $R^1$, $L^P$, and n have the meanings as defined hereinbefore and hereinafter. Suited reducing agents may be complex metal hydrides, such as sodium borohydride, lithium borohydride, sodium triacetoxyborohydride, or sodium cyano-borohydride, optionally used in combination with an acid, e.g. acetic acid, or hydrogen that is employed in the presence of a transition metal catalyst, e.g. palladium on charcoal or Raney-Ni.

Scheme 3

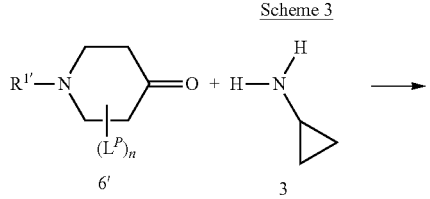

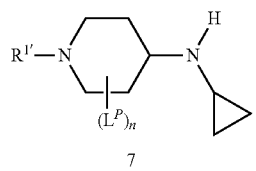

$R^{1'} = R^1$ or protective group, e.g., tBuOC(=O), $PhCH_2OC$(=O), $F_3CC$(=O)

The amide linkage in compounds I or any intermediate towards I of the carboxylic carbon atom and the N bearing the cyclopropyl group is a routine transformation in organic synthesis with a plethora of methods and strategies known (Scheme 4); $R^1$, $L^P$, n, HetAr, and Ar have the meanings as defined hereinbefore and hereinafter. The carboxylic acid may be transformed into a sufficiently reactive derivative to be coupled with the amine in a separate reaction step or in situ. Suited derivatives of the carboxylic acid for the former proceeding may be, for example, carboxylic chlorides, fluorides, cyanides, anhydrides, mixed anhydrides, imidazolides, oxybenzotriazolides, pentafluorophenyl esters, or 4-nitrophenyl esters. In situ activation of the carboxylic acid may be achieved with e.g. 2-(1H-benzotriazol-1-yl)-1,1,3,3-tetramethyluronium tetrafluoroborate or 2-(7-azabenzotriazol-1-yl)-1,1,3,3-tetramethyluronium hexafluorophosphate. The couplings are preferably conducted in the presence of a base, e.g. ethyl-diisopropyl-amine, triethylamine, imidazole, pyridine, potassium carbonate, or calcium oxide, and/or another additive, such as 4-dimethylaminopyridine or 1-hydroxybenzotriazol, in solvents, preferably selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, hexanes, and mixtures thereof, preferably at −10 to 140° C.

Scheme 4

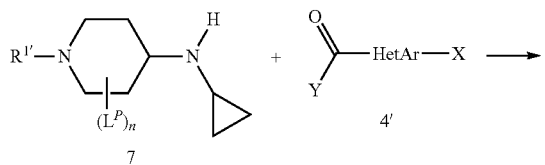

-continued

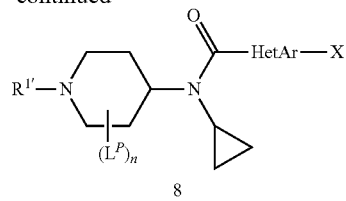

8

R<sup>1'</sup> = R<sup>1</sup> or protected group, e.g. tBuOC(═O), PhCH₂OC(═O), F₃CC(═O)
X = Ar or leaving group, e.g., Cl, Br, I, OSO₂CF₃, OSO2Me
Y = leaving group, e.g., F, C., imidazolide, tBuC(═O)O, iPrC(═O)O, benzotriazol-1-yl-O, pentafluorophenoxy, 4-nitrophenoxy Attaching Ar to the heteroaromatic ring HetAr in I or an intermediate towards I, e.g. compound 9, may be accomplished as depicted in Scheme 5; HetAr and Ar have the meanings as defined hereinbefore and hereinafter. Compound 9 is preferably employed as the electrophilic component bearing a leaving group, such as Cl, Br, I, F₃CSO₃, H₃CSO₃, and PhSO₃, and Ar as the nucleophilic partner bearing a metal or pseudo metal group, e.g. B(OH)₂, BF₃K, B(OCMe₂CMe₂O), ZnCl, ZnBr, and ZnI. The coupling of the two components is preferably mediated by a transition metal species derived from Fe, Cu, Ni, or Pd. The active catalyst may be a complex of the transition metal with ligands, such as phosphines, e.g. tri-tert-butylphosphine, tricyclohexyl-phosphine, optionally substituted biphenyl-dicyclohexylphosphines or biphenyl-di-tert-butylphosphines, 1,1'-bis(diphenylphosphino)-ferrocene, triphenylphosphine, tritolylphosphine, or trifurylphosphine, phosphites, 1,3-disubstituted imdiazole or imidazolidine carbenes, dibenzylideneacetone, allyl, or nitriles, an elemental form of the transition metal, such as Pd on carbon or nanoparticles of Fe or Pd, a salt, such as fluoride, chloride, bromide, acetate, triflate, or trifluoroacetate, or a combination of the different species mentioned. Depending on the nature of the electrophile and nucleophile additives, such as halide salts, e.g. LiCl, KF, and nBu₄NF, hydroxide sources, e.g. KOH, K₂CO₃, silver salts, such as Ag₂O and Ag(O₃SCF₃)₂, and/or Cu salts, such as copper thiophene-2-carboxylate, may be advantageous or even essential. The coupling is preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, at –10 to 180° C. The reactivity of the two building blocks may be reversed, i.e. compound 9 is the nucleophile bearing the metal or pseudo metal residue and Ar is the electrophile bearing the leaving group, to access the same products under analogous reaction conditions.

Scheme 5

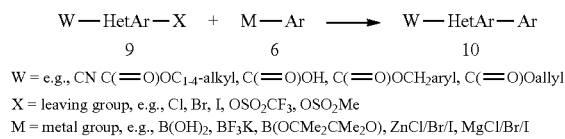

W = e.g., CN C(═O)OC₁₋₄-alkyl, C(═O)OH, C(═O)OCH₂aryl, C(═O)Oallyl
X = leaving group, e.g., Cl, Br, I, OSO₂CF₃, OSO₂Me
M = metal group, e.g., B(OH)₂, BF₃K, B(OCMe₂CMe₂O), ZnCl/Br/I, MgCl/Br/I The synthetic routes presented may rely on the use of protecting groups. For example, reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula I", "compound(s) of the invention" and the like denote the compounds of the formula I according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or the group to which the substituent is attached. For example, the term "3-carboxypropyl-group" represents the following substituent:

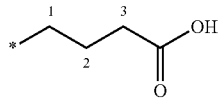

wherein the carboxy group is attached to the third carbon atom of the propyl group. The terms "1-methylpropyl-", "2,2-dimethylpropyl-" or "cyclopropylmethyl-" group represent the following groups:

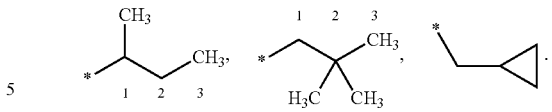

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$" or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of acids which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example, the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example, the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—

—CH₂—CH(CH₃))—, —(CH(CH₃)—CH₂—CH₂)—, —(CH₂—CH(CH₃)—CH₂)—, —(CH₂—C(CH₃)₂)—, —(C(CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "C₂₋ₙ-alkenyl", is used for a group as defined in the definition for "C₁₋ₙ-alkyl" with at least two carbon atoms, if at least two of those carbon atoms of said group are bonded to each other by a double bond. For example the term C₂₋₃-alkenyl includes —CH=CH₂, —CH=CH—CH₃, —CH₂—CH=CH₂.

The term "C₂₋ₙ-alkenylene" is used for a group as defined in the definition for "C₁₋ₙ-alkylene" with at least two carbon atoms, if at least two of those carbon atoms of said group are bonded to each other by a double bond. For example the term C₂₋₃-alkenylene includes —CH=CH—, —CH=CH—CH₂—, —CH₂—CH=CH—.

The term "C₂₋ₙ-alkynyl", is used for a group as defined in the definition for "C₁₋ₙ-alkyl" with at least two carbon atoms, if at least two of those carbon atoms of said group are bonded to each other by a triple bond. For example the term C₂₋₃-alkynyl includes —C≡CH, —C≡C—CH₃, —CH₂—C≡CH.

The term "C₂₋ₙ-alkynylene" is used for a group as defined in the definition for "C₁₋ₙ-alkylene" with at least two carbon atoms, if at least two of those carbon atoms of said group are bonded to each other by a triple bond. For example the term C₂₋₃-alkynylene includes —C≡C—, —C≡C—CH₂—, —CH₂—C≡C—.

The term "C₃₋ₙ-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C₃₋₁₀-carbocyclyl includes C₃₋₁₀-cylcoalkyl, C₃₋₁₀-cycloalkenyl, octahydropentalenyl, octahydroindenyl, decahydronaphthyl, indanyl, tetrahydronaphthyl. Most preferably the term C₃₋ₙ-carbocyclyl denotes C₃₋ₙ-cylcoalkyl, in particular C₃₋₇-cycloalkyl.

The term "C₃₋ₙ-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term bicyclic includes spirocyclic.

The term "C₃₋ₙ-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C₃₋₇-cycloalkenyl includes cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)ᵣ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)ᵣ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

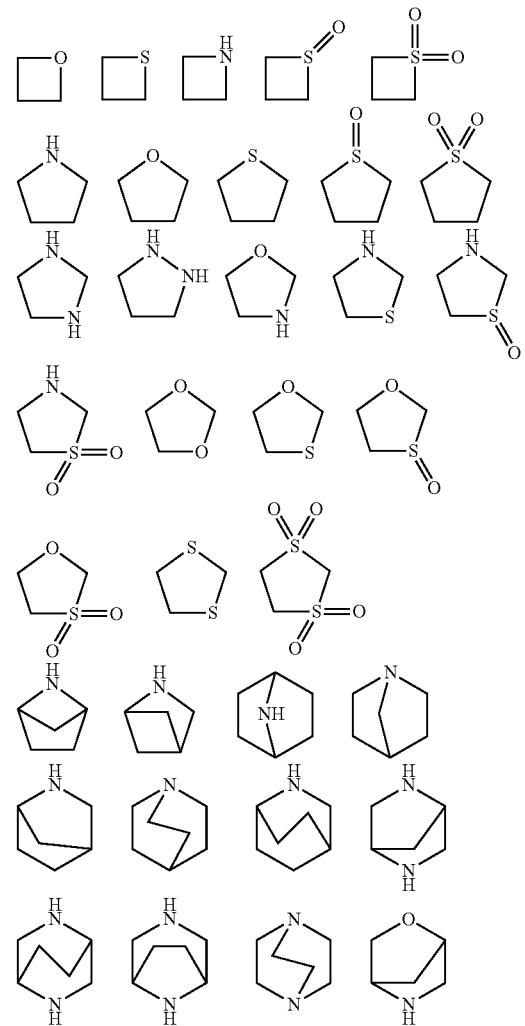

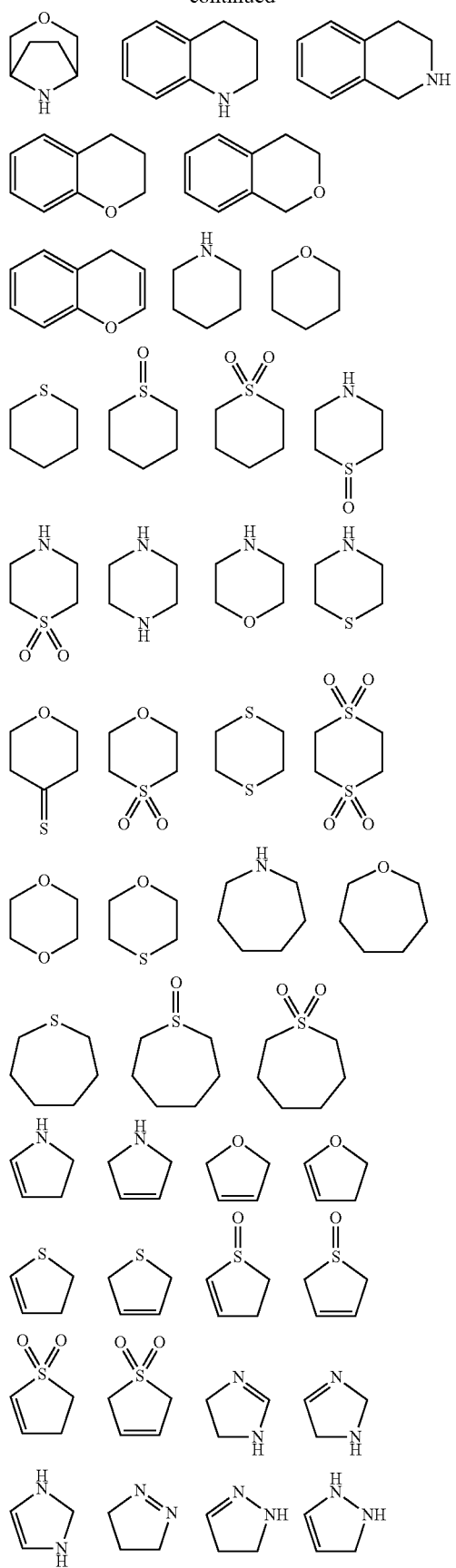
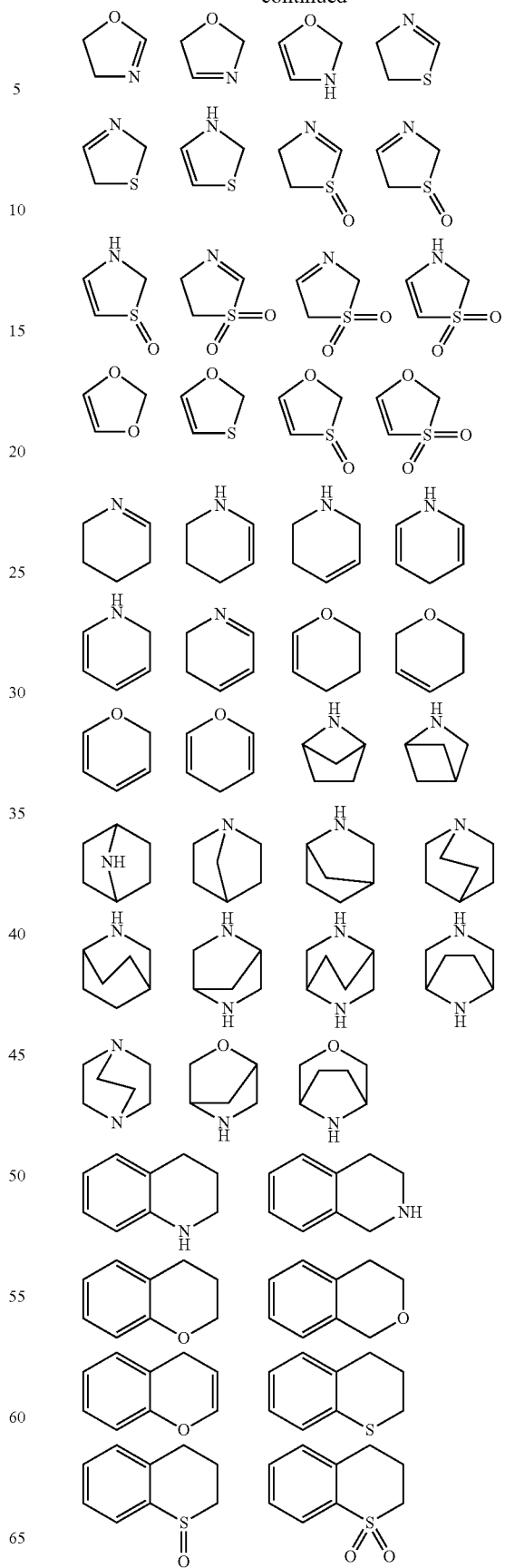

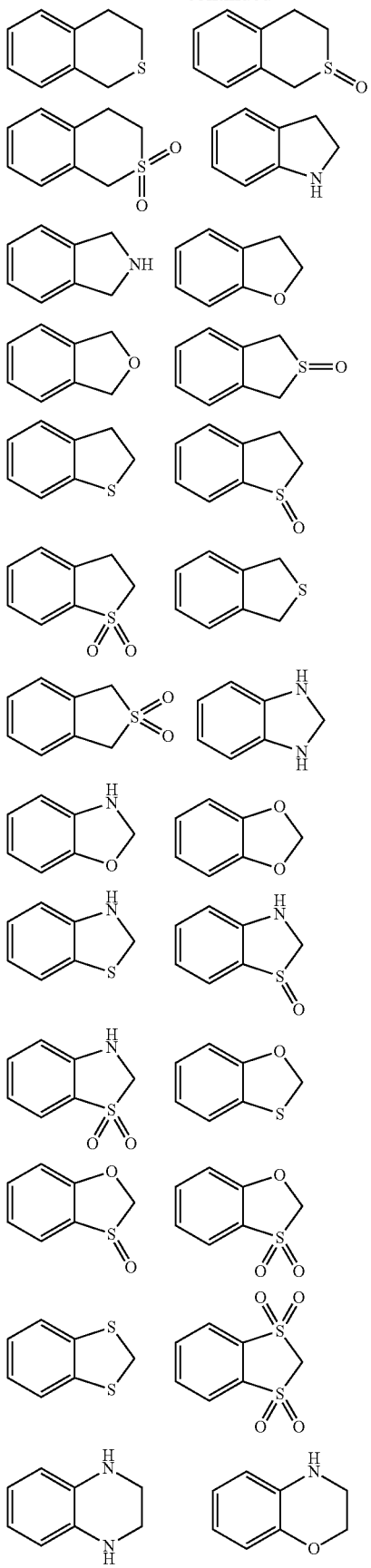
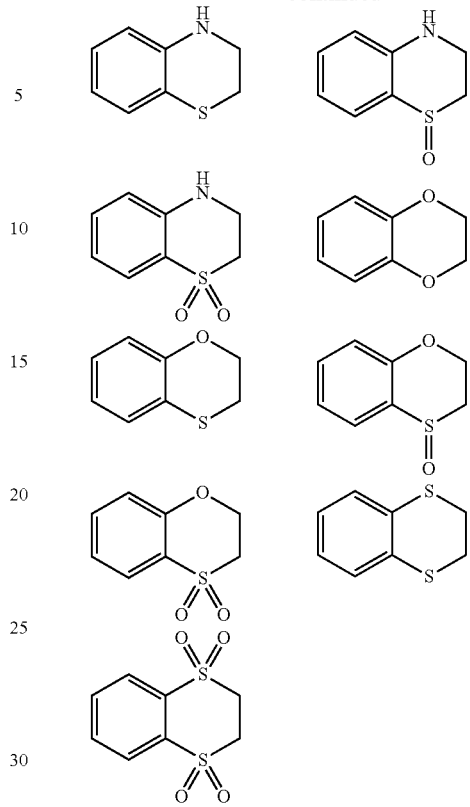

The term "heteroaryl" means a mono- or polycyclic, preferably mono- or bicyclic ring system containing one or more heteroatoms selected from N, O or $S(O)_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

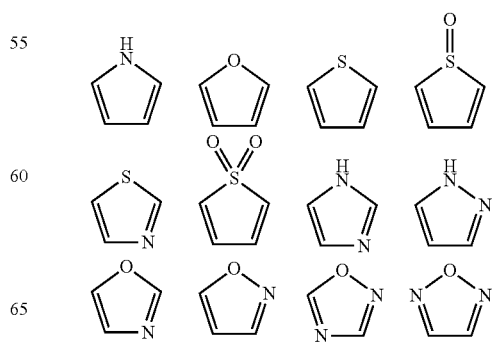

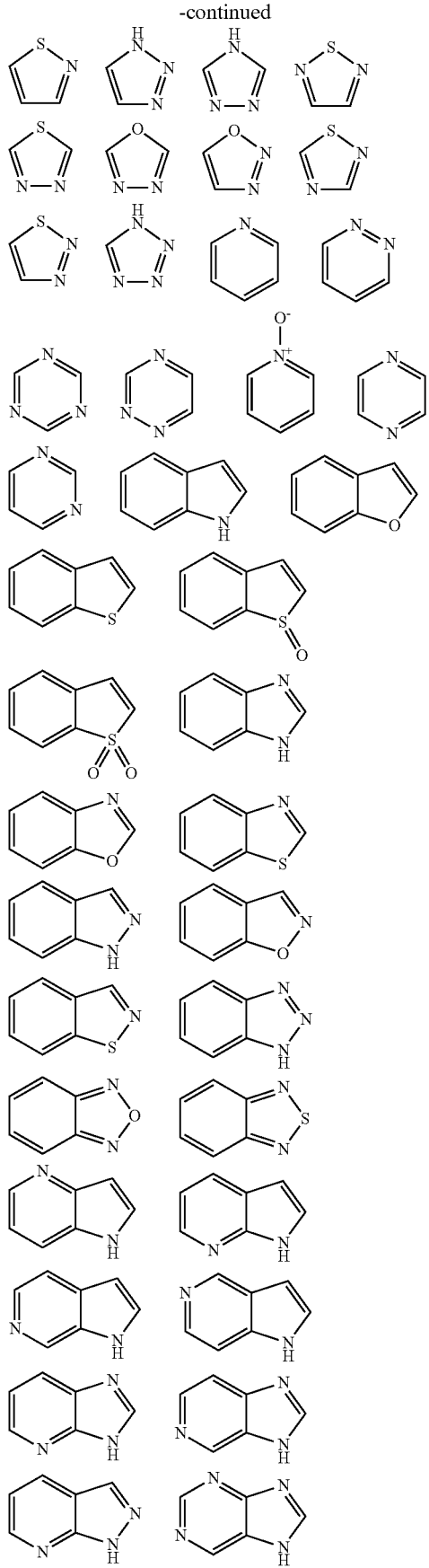
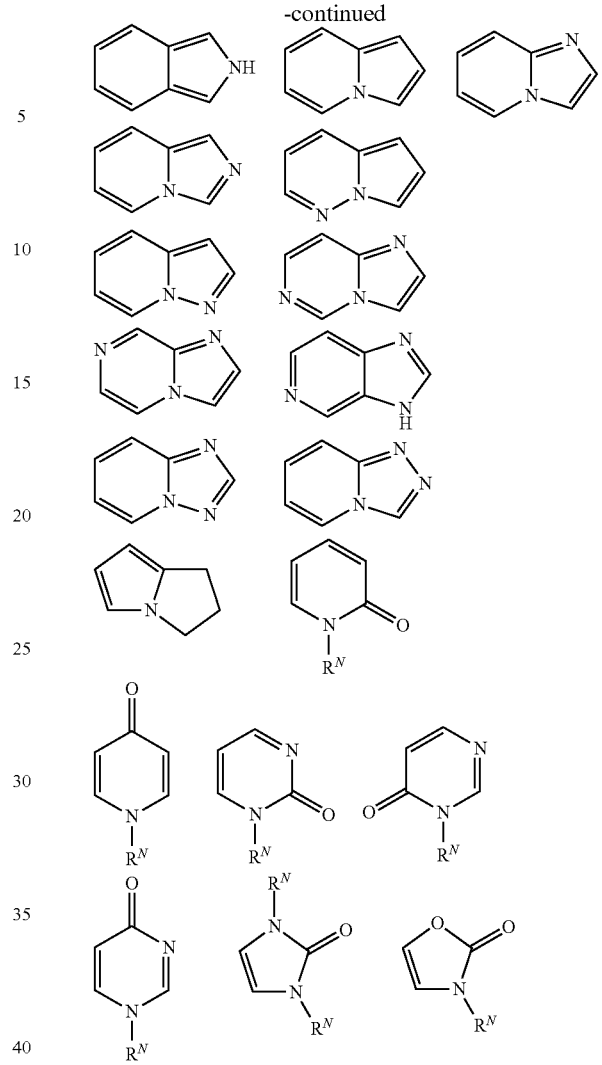

$R^N$=H or residue attached via a C atom

Many of the terms given above may be used repeatedly in the definition of a formula or group and in each case have one of the meanings given above, independently of one another.

Pharmacological Activity

The activity of the compounds of the invention may be demonstrated using the following assay:

The compounds of formula I according to the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat.No.#6760625R) made by PerkinElmer.

MIN6 cells [Miyazaki J et al. Endocrinology. 1990 July; 127(1):126-32] are stably transfected with an expression vector for human GPR119 cDNA (Acc. No. NP_848566). Min-6/hGPR119 cells are cultured in DMEM, 10% FBS, 50 μM β-mercaptoethanol, 0.3 mg/mL Geniticin, 2 mM GlutaMAX at 37° C. 5% CO2. For the assay, the cells are seeded in Optiplates (white, 384-well, 160W-barcoded, TC, sterile with lid, Cat.No.#6007688 (Perkin Elmer); 10000 cells/well; 50 μl). The plates covered with lids are then incubated for 24 hours at 37° C./5% $CO_2$. After the medium is aspirated from the wells completely, 10 μl of the test compound are added, the compounds are diluted using stimulating buffer (140 mM NaCl, 3.6 mM KCl, 0.5 mM NaH$_2$PO$_4$, 0.5 mM MgSO$_4$, 1.5 mM CaCl$_2$, 10 mM Hepes, 5 mM NaHCO$_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat.No.#6760625R from PerkinElmer). 10 µl of Biotin-cAMP (final concentration 1 U/well in lysing buffer (5 mM Hepes (pH 7.4), 0.1% BSA, 0.5% Tween) and 10 µL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the EC$_{50}$ value and the maximum value based on a positive control, using suitable software (Graphpad Prism). The compounds according to the invention increase the intracellular cAMP level in the range of 3-5.

The compounds according to the invention typically have EC$_{50}$ values in the range from about 1 nM to about 10 µM, preferably from 1 nM to 1 µM, preferably less than 1 µM, particularly preferably less than 500 nM, most particularly preferably less than 100 nM.

EC$_{50}$ values (cAMP assay) for compounds according to the invention are shown in the following table. The number of the compound corresponds to the number of the Example in the experimental section.

| Example No. | EC$_{50}$ [nM] |
| --- | --- |
| 1 | 31 |
| 2 | 11 |
| 3 | 487 |
| 4 | 94 |
| 5 | 118 |
| 6 | 96 |
| 7 | 25 |
| 8 | 36 |
| 9 | 19 |
| 10 | 101 |
| 11 | 32 |
| 12 | 35 |
| 13 | 24 |
| 14 | 21 |
| 15 | 60 |
| 16 | 159 |
| 17 | 964 |
| 18 | 7 |
| 19 | 97 |
| 20 | 92 |
| 21 | 123 |
| 22 | 137 |
| 23 | 103 |
| 24 | 83 |
| 25 | 103 |
| 26 | 156 |
| 27 | 6 |
| 28 | 3 |
| 29 | 3 |
| 30 | 5 |
| 31 | 6 |
| 32 | 14 |
| 33 | 25 |
| 34 | 27 |
| 35 | 33 |
| 36 | 46 |
| 37 | 59 |
| 38 | 63 |
| 39 | 67 |
| 40 | 89 |
| 41 | 159 |
| 42 | 231 |

Alternatively, the effect of the compounds on the activation of GPR119 are determined as follows:

Quantitative detection of cAMP accumulation from cells expressing human GPR119 receptor is achieved using Perkin Elmer's LANCE cAMP-384 Kit (Cat#AD0264) according to the manufacturer's protocol. Briefly, HEK293 cells stably expressing a mutant form of the human GPR119 receptor as assay tool (Methionine 1 replaced with the amino acid sequence MKTIIALSYIFCLVFADYKDDDDA, and T327 & S329 changed to alanines; SEQ ID No. 1) are grown to 50-70% confluency in cell culture media (DMEM, 10% heat inactivated Fetal Bovine Serum, 50 I.U./mL penicillin, 50 µg/mL streptomycin, 10 mM HEPES, 20 µg/mL G418 Sulfate). On the day of the assay, GPR119 stable HEK293 cells are lifted from the tissue culture plate and 1000 cells/well are incubated along with various concentrations of test compounds for 20 min at 37° C. Detection Buffer (50 mM HEPES, 10 mM calcium chloride, 0.35% Triton X-100, 1 mg/mL BSA) containing cAMP-specific antibody is then added to all wells and allowed to equilibrate in the dark for 10 minutes at room temperature. Upon equilibration, Detection Buffer containing europium-labeled cAMP tracer complex is added to all wells and allowed to react for 1 hour at room temperature. After 1 hour, bound europium-labeled cAMP tracer is measured using a Perkin Elmer Envision plate reader. The quantity of cAMP generated in each well is derived from a standard curve. EC$_{50}$ is determined using nonlinear regression analysis of the cAMP values over a range of agonist concentration (12 points spanning the range from 30 µM to 100 pM).

EC$_{50}$ values (determined as described immediately above) for compounds according to the invention are shown in the following table. The number of the compound corresponds to the number of the Example in the experimental section.

| Example No. | EC$_{50}$ [nM] |
| --- | --- |
| 43 | 73 |
| 44 | 22 |
| 45 | 16 |
| 46 | 78 |
| 47 | 125 |
| 48 | 27 |
| 49 | 9 |
| 50 | 148 |
| 51 | 593 |
| 52 | 231 |
| 53 | 808 |
| 54 | 812 |
| 55 | 512 |
| 56 | 473 |
| 57 | 231 |
| 58 | 553 |
| 59 | 1242 |
| 60 | 29 |
| 61 | 98 |
| 62 | 185 |
| 63 | 385 |
| 64 | 252 |
| 65 | 333 |
| 66 | 73 |
| 67 | 45 |
| 68 | 125 |
| 69 | 496 |
| 70 | 127 |
| 71 | 94 |
| 72 | 56 |
| 73 | 391 |
| 74 | 411 |
| 75 | 341 |
| 76 | 46 |

-continued

| Example No. | EC$_{50}$ [nM] |
|---|---|
| 77 | 13 |
| 78 | 9 |
| 79 | 6 |
| 80 | 111 |
| 81 | 34 |
| 82 | 35 |
| 83 | 12 |
| 84 | 15 |
| 85 | 20 |
| 86 | 5 |
| 87 | 4 |
| 88 | 29 |
| 89 | 18 |
| 90 | 44 |
| 91 | 202 |
| 92 | 609 |
| 93 | 24 |
| 94 | 8 |
| 95 | 7 |
| 96 | 65 |
| 97 | 32 |
| 98 | 14 |
| 99 | 18 |
| 100 | 136 |
| 101 | 5 |
| 102 | 50 |
| 103 | 391 |
| 104 | 61 |
| 105 | 233 |
| 106 | 57 |
| 107 | 188 |
| 108 | 82 |
| 109 | 53 |
| 110 | 363 |
| 111 | 1609 |
| 112 | 789 |

In view of their ability to modulate the activity of the G-protein-coupled receptor GPR119, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR119.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macro-angiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD1 inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates to a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm. The terms "ambient temperature" and "room temperature" are used interchangeably and designate a temperature of about 20° C.

Analytical HPLC and SFC parameters employed for characterization of products (TFA denotes trifluoroacetic acid):

| method 1 | Waters X-terra MS C18, 4.6 mm × 30 mm, 2.5 μm | | | method 2 | Waters XBridge C18, 4.6 × 30 mm, 2.5 μm, 60° C. | | |
|---|---|---|---|---|---|---|---|
| column | A: water + 0.1% HCO$_2$H | | | column | A: water + 0.1% TFA | | |
| | B: H$_3$CCN + 0.1% HCO$_2$H | | | | B: methanol + 0.1% TFA | | |
| | TIME (min) | A % | B % | | TIME (min) | A % | B % |
| | 0.00 | 95 | 5 | | 0.00 | 95 | 5 |
| | 0.10 | 95 | 5 | | 0.05 | 95 | 5 |
| | 3.10 | 2 | 98 | | 2.05 | 0 | 100 |
| | 4.50 | 2 | 98 | | 2.10 | 0 | 100 |
| | 5.00 | 95 | 5 | | 2.35 | 0 | 100 |
| flow rate | 1.0 mL/min | | | flow rate | 3-4 mL/min | | |
| wavelength | 210-420 nm | | | wavelength | UV 220, 230, or 254 nm | | |

| method 3 | Waters Sunfire C18, 4.6 × 30 mm, 2.5 μm, 60° C. | | | method 4 | Waters Sunfire C18, 3 × 30 mm, 2.5 μm, 60° C. | | |
|---|---|---|---|---|---|---|---|
| column | A: water + 0.1% TFA | | | column | A: water + 0.1% TFA | | |
| | B: methanol + 0.1% TFA | | | | B: methanol | | |
| | TIME (min) | A % | B % | | TIME (min) | A % | B % |
| | 0.00 | 95 | 5 | | 0.00 | 95 | 5 |
| | 0.05 | 95 | 5 | | 0.30 | 95 | 5 |
| | 2.05 | 0 | 100 | | 1.50 | 0 | 100 |
| | 2.10 | 0 | 100 | | 1.55 | 0 | 100 |
| | 2.35 | 0 | 100 | | 1.65 | 0 | 100 |
| flow rate | 3-4 mL/min | | | flow rate | 2.2-2.9 mL/min | | |
| wavelength | UV 220, 230, or 254 nm | | | wavelength | UV 220, 230, or 254 nm | | |

| method 5 | Waters XBridge C18, 4.6 × 30 mm, 3.5 μm, 60° C. | | | method 6 | Waters XBridge C18, 4.6 × 30 mm, 3.5 μm, 60° C. | | |
|---|---|---|---|---|---|---|---|
| column | A: water + 0.1% TFA | | | column | A: water + 0.1% TFA | | |
| | B: methanol + 0.1% TFA | | | | B: methanol + 0.1% TFA | | |
| | TIME (min) | A % | B % | | TIME (min) | A % | B % |
| | 0.00 | 95 | 5 | | 0.00 | 95 | 5 |
| | 0.15 | 95 | 5 | | 0.20 | 95 | 5 |
| | 1.70 | 0 | 100 | | 1.50 | 0 | 100 |
| | 2.25 | 0 | 100 | | 1.75 | 0 | 100 |
| | | | | | 1.85 | 95 | 5 |
| flow rate | 4 mL/min | | | flow rate | 4 mL/min | | |
| wavelength | UV 220, 230, or 254 nm | | | wavelength | UV 220, 230, or 254 nm | | |

| method 7 | Waters XBridge C18, 3 × 30 mm, 2.5 μm, 60° C. | | | method 8 | Waters XBridge C18, 4.6 × 30 mm, 3.5 μm, 60° C. | | |
|---|---|---|---|---|---|---|---|
| column | A: water + 0.2% TFA | | | column | A: water + 0.1% HCO$_2$H | | |
| | B: methanol | | | | B: methanol | | |
| | TIME (min) | A % | B % | | TIME (min) | A % | B % |
| | 0.00 | 95 | 5 | | 0.0 | 95 | 5 |
| | 0.05 | 95 | 5 | | 0.15 | 95 | 5 |

| | | | | | | | |
|---|---|---|---|---|---|---|---|
| | 1.40 | 0 | 100 | | 1.7 | 0 | 100 |
| | 1.80 | 0 | 100 | | 2.25 | 0 | 100 |
| flow rate | 2.2 mL/min | | | flow rate | 4 mL/min | | |
| wavelength | UV 220, 230, or 254 nm | | | wavelength | UV 220, 230, or 254 nm | | |

| | | | | | | | |
|---|---|---|---|---|---|---|---|
| method 9 column | Waters Sunfire C18, 3 × 30 mm, 2.5 µm, 60° C. A: water + 0.1% HCO₂H B: methanol | | | method 10 column | Waters Sunfire C18, 4.6 × 30 mm, 2.5 µm, 60° C. A: water + 0.1% TFA B: methanol | | |
| | TIME (min) | A % | B % | | TIME (min) | A % | B % |
| | 0.00 | 95 | 5 | | 0.00 | 95 | 5 |
| | 0.25 | 95 | 5 | | 0.05 | 95 | 5 |
| | 1.70 | 0 | 100 | | 2.05 | 0 | 100 |
| | 1.75 | 0 | 100 | | 2.10 | 0 | 100 |
| | 1.90 | 0 | 100 | | 2.40 | 0 | 100 |
| flow rate | 1.8-2.5 mL/min | | | flow rate | 3-4.5 mL/min | | |
| wavelength | UV 220, 230, or 254 nm | | | wavelength | UV 220, 230, or 254 nm | | |

| | | | | | | | |
|---|---|---|---|---|---|---|---|
| method 11 column | Waters Sunfire C18, 3 × 30 mm, 2.5 µm, 60° C. A: water + 0.1% TFA B: methanol | | | method 12 column | XBridge C18, 4.6 × 50 mm, 3.5 µm, 40° C. A: water + 0.1% NH₄OH B: methanol | | |
| | TIME (min) | A % | B % | | TIME (min) | A % | B % |
| | 0.00 | 95 | 5 | | 0.00 | 95 | 5 |
| | 0.25 | 95 | 5 | | 2.00 | 0 | 100 |
| | 1.70 | 0 | 100 | | | | |
| | 1.75 | 0 | 100 | | | | |
| | 1.90 | 0 | 100 | | | | |
| flow rate | 1.8-2.5 mL/min | | | flow rate | 1.5 mL/min | | |
| wavelength | UV 220, 230, or 254 nm | | | wavelength | 210-500 nm | | |

| | | | | | | | |
|---|---|---|---|---|---|---|---|
| method 13 column | XBridge C18, 4.6 × 50 mm, 3.5 µm, 40° C. A: water + 0.032 NH₄OH B: methanol | | | method 14 column | Waters XBridge C18, 4.6 × 30 mm, 3.5 µm, 60° C. A: water + 0.1% TFA B: methanol | | |
| | TIME (min) | A % | B % | | TIME (min) | A % | B % |
| | 0.00 | 95 | 5 | | 0.00 | 95 | 5 |
| | 2.00 | 0 | 100 | | 1.60 | 0 | 100 |
| | | | | | 1.85 | 0 | 100 |
| | | | | | 1.90 | 95 | 5 |
| flow rate | 1.5 mL/min | | | flow rate | 4 mL/min | | |
| wavelength | 210-500 nm | | | wavelength | UV 220, 230, or 254 nm | | |

| | | | | | | | |
|---|---|---|---|---|---|---|---|
| method 15 column | Waters XBridge C18, 4.6 × 30 mm, 3.5 µm, 60° C. A: water + 0.1% TFA B: methanol | | | method 16 column | Waters XBridge C18, 3.0 × 30 mm, 2.5 µm, 60° C. A: water + 0.1% NH₄OH B: methanol | | |
| | TIME (min) | A % | B % | | TIME (min) | A % | B % |
| | 0.0 | 95 | 5 | | 0.00 | 95 | 5 |
| | 1.6 | 0 | 100 | | 0.30 | 95 | 5 |
| | 1.85 | 0 | 100 | | 1.50 | 0 | 100 |
| | 1.9 | 95 | 5 | | 1.55 | 0 | 100 |
| | | | | | 1.70 | 0 | 100 |
| flow rate | 4.8 mL/min | | | flow rate | 2.2-2.9 mL/min | | |
| wavelength | UV 220, 230, or 254 nm | | | wavelength | UV 220, 230, or 254 nm | | |

| method 17 column | Waters X-terra MS C18, 2,5 μm 4,6 × 30 mm A: water + 0.1% HCO₂H B: H₃CCN + 0.1% HCO₂H | | | method 18 column | Waters XBridge C18, 3 × 30 mm, 2.5 μm, 60° C. A: water + 0.1% NH₄OH B: methanol | | |
|---|---|---|---|---|---|---|---|
| | TIME (min) | A % | B % | | TIME (min) | A % | B % |
| | 0.00 | 95 | 5 | | 0.00 | 95 | 5 |
| | 2.00 | 0 | 100 | | 0.05 | 95 | 5 |
| | 2.50 | 0 | 100 | | 1.40 | 0 | 100 |
| | 2.60 | 95 | 5 | | 1.80 | 0 | 100 |
| flow rate | 1.5 mL/min | | | flow rate | 2.2 mL/min | | |
| wavelength | 210-420 nm | | | wavelength | 210-420 nm | | |

| method 19 column | Waters XBridge C18, 4,6 × 30 mm, 3.5 μm, 60° C. A: water + 0.1% NH₄OH B: methanol | | | method 20 column | Phenomenex Synergi: MAX-RP, 2 × 50 mm A: water + 0025% TFA B: H₃CCN + 0.025% TFA | | |
|---|---|---|---|---|---|---|---|
| | TIME (min) | A % | B % | | TIME (min) | A % | B % |
| | 0.00 | 95 | 5 | | 0.00 | 95 | 5 |
| | 0.15 | 95 | 5 | | 2.50 | 10 | 90 |
| | 1.70 | 0 | 100 | | 3.50 | 10 | 90 |
| | 2.25 | 0 | 100 | | | | |
| flow rate | 4 mL/min | | | flow rate | 1.0 mL/min | | |
| wavelength | 210-420 nm | | | wavelength | 220 or 254 nm | | |

| method 21 column | Phenomenex Synergi: MAX-RP, 2 × 50 mm A: water + 0025% TFA B: H₃CCN + 0.025% TFA | | | method 22 column | Chiral SFC Technologies Chiralcel AD-H, 21 × 250 mm, 5 μm A: CO₂ B: EtOH + 0.5% N,N-dimethylethylamine | | |
|---|---|---|---|---|---|---|---|
| | TIME (min) | A % | B % | | TIME (min) | A % | B % |
| | 0.00 | 95 | 5 | | 0.00 | 90 | 10 |
| | 13.50 | 5 | 95 | | 15 | 90 | 10 |
| | 15.50 | 5 | 95 | | | | |
| flow rate | 1.0 mL/min | | | flow rate | 65 mL/min | | |
| wavelength | 220 or 254 nm | | | wavelength | 220 or 254 nm | | |

| method 23 column | Phenomenex Geminii: NX C18, 3 × 100 mm, 5 μm A: water + 0.04% NH₄OH B: H₃CCN + 0.04% NH₄OH | | |
|---|---|---|---|
| | TIME (min) | A % | B % |
| | 0.00 | 95 | 5 |
| | 5.20 | 5 | 95 |
| flow rate | 2.0 mL/min | | |
| wavelength | 220 or 254 nm | | |

Intermediate 1

1,4-Dioxa-8-aza-spiro[4.5]decane-8-carbonitrile

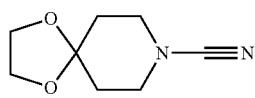 [SMILES: N#CN1CCC2(CC1)OCCO2]

Bromonitrile (11.12 g) is added to a mixture of 1,4-dioxa-8-aza-spiro[4.5]decane (10.00 g) and ethyldiisopropylamine (59.92 mL) in dichloromethane (125 mL) and tetrahydrofuran (125 mL). The reaction mixture is stirred over night at room temperature. Water is added and the organic phase is separated, dried over Na₂SO₄ and concentrated in vacuo to give the title compound. TLC: r$_f$=0.80 (aluminum oxide, ethyl acetate/petrol ether 3:1); Mass spectrum (ESI⁺): m/z=169 [M+H]⁺.

Intermediate 2

8-(3-Phenyl-[1,2,4]oxadiazol-5-yl)-1,4-dioxa-8-aza-spiro[4.5]decane

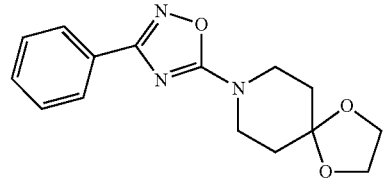 [SMILES: c1ccc(-c2noc(N3CCC4(CC3)OCCO4)n2)cc1]

A 0.5 M solution of zinc chloride in tetrahydrofuran (18.00 mL) is added dropwise at room temperature to a mixture of N-hydroxy-benzamidine (817 mg) and 1,4-dioxa-8-aza-spiro [4.5]decane-8-carbonitrile (1.00 g) in ethyl acetate (20 mL). The reaction mixture is stirred at 50° C. for 3 h and cooled to room temperature. The precipitate is filtered off and heated to 100° C. for 1 h in a mixture of ethanol (10 mL) and glacial acetic acid (5 mL). The solvents are evaporated and the crude product is purified by HPLC. TLC: r$_f$=0.88 (silica gel, CH₂Cl₂/MeOH 9:1); Mass spectrum (ESI⁺): m/z=288 [M+H]⁺.

Intermediate 3

1-(3-Phenyl-[1,2,4]oxadiazol-5-yl)-piperidin-4-one

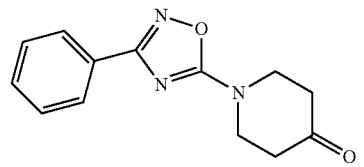 [SMILES: O=C1CCN(c2nc(-c3ccccc3)no2)CC1]

A mixture of 8-(3-phenyl-[1,2,4]oxadiazol-5-yl)-1,4-dioxa-8-aza-spiro[4.5]decane (660 mg), conc. aqueous HCl (5 mL), and water (5 mL) is kept at room temperature over night. The mixture is basified with conc. aqueous ammonia and the precipitate is filtered off and dissolved in dichloromethane. The resulting solution is dried over Na₂SO₄ and concentrated in vacuo to give the title compound. TLC: $r_f$=0.33 (silica gel, hexane/ethyl acetate 2:1); Mass spectrum (ESI$^+$): m/z=244 [M+H]$^+$.

Intermediate 4

Cyclopropyl-[1-(3-phenyl-[1,2,4]oxadiazol-5-yl)-piperidin-4-yl]-amine

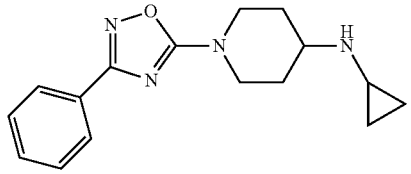 [SMILES: c1ccc(-c2noc(N3CCC(NC4CC4)CC3)n2)cc1]

A mixture of 1-(3-phenyl-[1,2,4]oxadiazol-5-yl)-piperidin-4-one (400 mg), cyclopropylamine (120 µL), sodium triacetoxyborohydride (420 mg), and glacial acetic acid (0.20 mL) in dichloromethane (7 mL) is stirred for two days at room temperature. Dichloromethane is added and the mixture is washed with aqueous $K_2CO_3$ solution. The organic phase is dried over $Na_2SO_4$ and concentrated in vacuo to afford the title compound. TLC: $r_f$=0.30 (silica gel, $CH_2Cl_2$/MeOH 95:5); Mass spectrum (ESI$^+$): m/z=285 [M+H]$^+$.

Intermediate 5

4-[(2-Chloro-pyrimidine-5-carbonyl)-cyclopropyl-amino]-piperidine-1-carboxylic acid tert-butyl ester

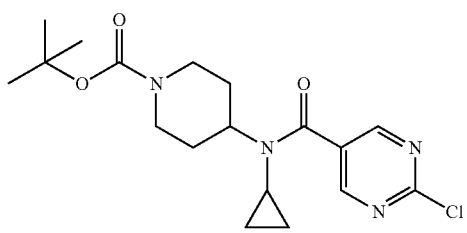 [SMILES: CC(C)(C)OC(=O)N1CCC(N(C(=O)c2cnc(Cl)nc2)C2CC2)CC1]

A mixture of 2-chloropyrimidine-5-carboxylic acid (2.00 g), ethyldiisopropylamine (6.39 mL), and chloro-N,N,N',N'-tetramethylformamidinium hexafluorophosphate (4.21 g) in tetrahydrofuran (15 mL) is stirred for 45 min at room temperature prior to the addition of 4-cyclopropylamino-piperidine-1-carboxylic acid tert-butyl ester (2.94 g). The resulting mixture is stirred at room temperature for 1 h. The solvent is evaporated in vacuo and the residue purified by HPLC($H_2O$/MeOH/TFA). LC (method 3): $t_R$=1.89 min; Mass spectrum (ESI$^+$): m/z=381/383 (Cl) [M+H]$^+$.

Intermediate 6

2-(6-Ethoxy-pyridin-3-yl)-pyrimidine-5-carboxylic acid cyclopropyl-piperidin-4-yl-amide

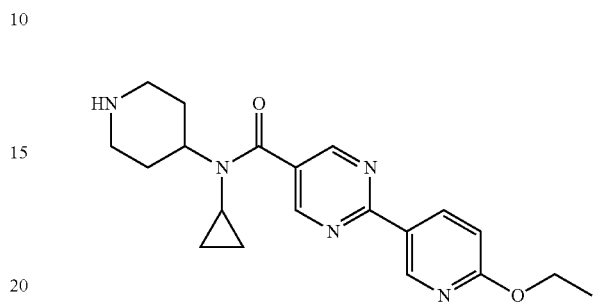

Aqueous $Na_2CO_3$ solution (2 M, 1.05 mL) and Pd(PPh$_3$)$_2$Cl$_2$ (22 mg) are added to a mixture of 4-[(2-chloro-pyrimidine-5-carbonyl)-cyclopropyl-amino]-piperidine-1-carboxylic acid tert-butyl ester (400 mg) and 2-ethoxy-5-pyridineboronic acid (351 mg) in 1,4-dioxane (20 mL) and methanol (10 mL) under argon atmosphere. The reaction mixture is stirred over night at 80° C. After cooling to room temperature, the solvents are evaporated and the residue is mixed with dichloromethane and water. The aqueous phase is extracted with dichloromethane and the combined organic phases are dried and concentrated in vacuo. The crude product is dissolved in dichloromethane and trifluoroacetic acid is added. The mixture is stirred for 1 h at room temperature and concentrated in vacuo. The crude product is purified by HPLC (MeOH/$H_2O$/TFA) to give the title compound as trifluoroacetic acid salt. LC (method 4): $t_R$=0.99 min; Mass spectrum (ESI$^+$): m/z=368 [M+H]$^+$.

Intermediate 7

2-(4-Cyano-3-fluoro-phenyl)-pyrimidine-5-carboxylic acid cyclopropyl-piperidin-4-yl-amide

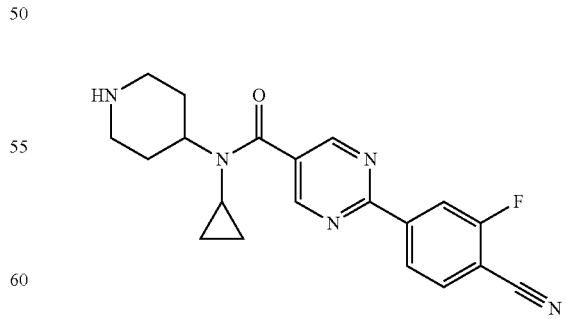

The title compound is prepared from 4-[(2-chloro-pyrimidine-5-carbonyl)-cyclopropyl-amino]-piperidine-1-carboxylic acid tert-butyl ester and 4-cyano-3-fluorophenylboronic acid following a procedure analogous to that described in Intermediate 6. LC (method 4): $t_R$=0.97 min; Mass spectrum (ESI$^+$): m/z=366 [M+H]$^+$.

Intermediate 8

2-(4-Cyanomethyl-phenyl)-pyrimidine-5-carboxylic acid cyclopropyl-piperidin-4-yl amide

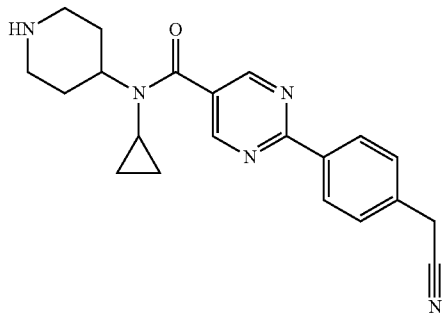 [SMILES: N#CCc1ccc(-c2ncc(C(=O)N(C3CCNCC3)C3CC3)cn2)cc1]

The title compound is prepared from 4-[(2-chloro-pyrimidine-5-carbonyl)-cyclopropyl-amino]-piperidine-1-carboxylic acid tert-butyl ester and (4-cyanomethylphenyl)boronic acid following a procedure analogous to that described in Intermediate 6. LC (method 4): $t_R$=0.85 min; Mass spectrum (ESI$^+$): m/z=362 [M+H]$^+$.

Intermediate 9

4-[(6-Bromo-pyridine-3-carbonyl)-cyclopropyl-amino]-piperidine-1-carboxylic acid tert-butyl ester

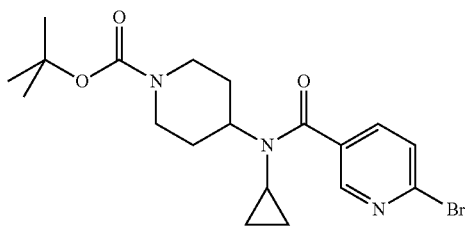 [SMILES: CC(C)(C)OC(=O)N1CCC(N(C(=O)c2ccc(Br)nc2)C2CC2)CC1]

2-(1H-Benzotriazol-1-yl)-1,1,3,3-tetramethyluronium tetrafluoroborate (2.80 g) is added to a mixture of 6-bromonicotinic acid (1.85 g) and triethylamine (1.28 mL) in N,N-dimethylformamide (25 mL) cooled in an ice bath. The mixture is stirred for 30 min prior to the addition of a solution of 4-cyclopropylamino-piperidine-1-carboxylic acid tert-butyl ester (2.00 g) in N,N-dimethylformamide (5 mL). The resulting mixture is stirred at room temperature over night. Water and ethyl acetate are added and the organic phase is separated, washed with water, 1N aqueous NaOH solution, and brine, and dried over MgSO$_4$. The solvent is evaporated in vacuo and the residue is triturated with diisopropyl ether to yield the title compound. LC (method 5): $t_R$=1.59 min; Mass spectrum (ESI$^+$): m/z=424/426 (Br) [M+H]$^+$.

Intermediate 10

4-{Cyclopropyl-[6-(4-methanesulfonyl-phenyl)-pyridine-3-carbonyl]-amino}-piperidine-1-carboxylic acid tert-butyl ester

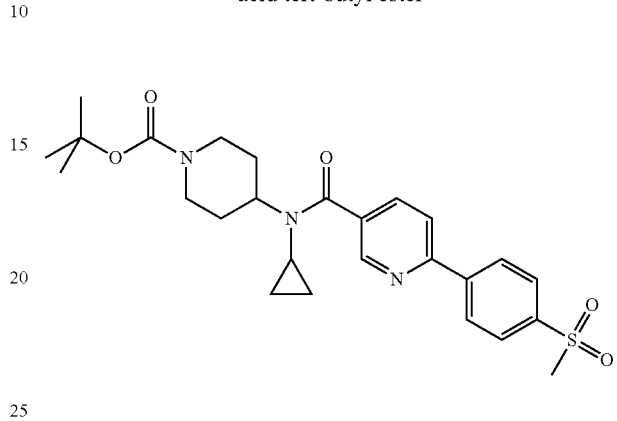

2 M aqueous Na$_2$CO$_3$ solution (8.26 mL) is added to a mixture of 4-[(6-bromo-pyridine-3-carbonyl)-cyclopropyl-amino]-piperidine-1-carboxylic acid tert-butyl ester (500 mg) and 4-(methanesulfonyl)phenylboronic acid (259 mg) in N,N-dimethylformamide (5 mL). The mixture is sparged with argon for 10 min and [1,1'-bis(diphenylphosphino)-ferrocene]dichloropalladium dichloromethane complex (96 mg) is added. The resulting mixture is stirred for 6 h at 90° C. After cooling to room temperature, water (50 mL) is added and the aqueous phase is extracted with ethyl acetate. The organic phase is dried over MgSO$_4$, the solvent is evaporated, and the residue is chromatographed on silica gel (ethyl acetate/cyclohexane 3:1→1:0) to afford the title compound. LC (method 6): $t_R$=1.17 min; Mass spectrum (ESI$^+$): m/z=500 [M+H]$^+$.

Intermediate 11

N-Cyclopropyl-6-(4-methanesulfonyl-phenyl)-N-piperidin-4-yl-nicotinamide

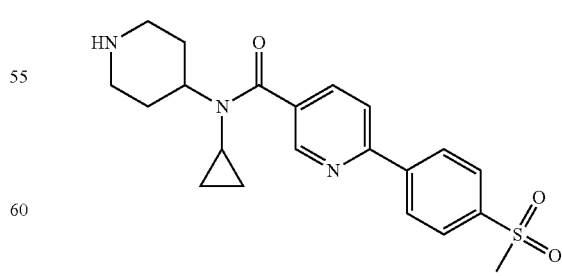

The title compound is prepared from 4-{cyclopropyl-[6-(4-methanesulfonyl-phenyl)-pyridine-3-carbonyl]-amino}-piperidine-1-carboxylic acid tert-butyl ester by treatment with trifluoroacetic acid in dichloromethane. LC (method 6): $t_R$=0.70 min; Mass spectrum (ESI$^+$): m/z=400 [M+H]$^+$.

Intermediate 12

N-(1-Cyano-piperidin-4-yl)-N-cyclopropyl-6-(4-methanesulfonyl-phenyl)-nicotinamide

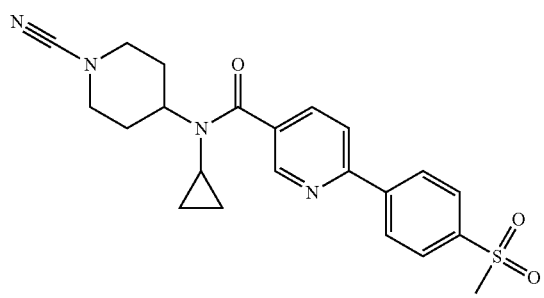 [SMILES: CS(=O)(=O)c1ccc(-c2ccc(C(=O)N(C3CC3)C3CCN(C#N)CC3)cn2)cc1]

Bromonitrile (44 mg) is added to a solution of N-cyclopropyl-6-(4-methanesulfonyl-phenyl)-N-piperidin-4-yl-nicotinamide (111 mg) and ethyldiisopropylamine (238 μL) in dichloromethane (2.5 mL) and tetrahydrofuran (2.5 mL). The reaction mixture is stirred for two days at room temperature prior to the addition of water and ethyl acetate. The organic phase is separated, washed with water and brine, dried over MgSO$_4$ and concentrated in vacuo. The crude product is used without further purification for the next reaction step. LC (method 7): $t_R$=0.87 min; Mass spectrum (ESI$^+$): m/z=425 [M+H]$^+$.

Intermediate 13

2-(6-Ethoxy-pyridin-3-yl)-pyrimidine-5-carboxylic acid (1-cyano-piperidin-4-yl)-cyclopropyl-amide

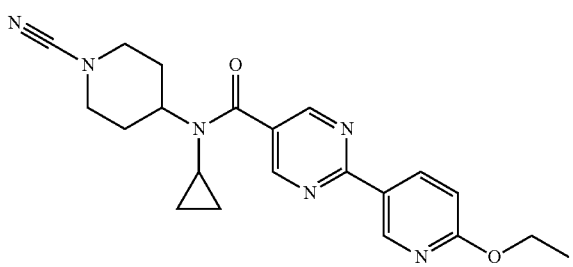 [SMILES: CCOc1ccc(-c2ncc(C(=O)N(C3CC3)C3CCN(C#N)CC3)cn2)cn1]

The title compound is prepared from 2-(6-ethoxy-pyridin-3-yl)-pyrimidine-5-carboxylic acid cyclopropyl-piperidin-4-yl-amide following a procedure analogous to that described in Intermediate 12. LC (method 3): $t_R$=1.89 min; Mass spectrum (ESI$^+$): m/z=393 [M+H]$^+$.

Intermediate 14

2-(4-Cyanomethyl-phenyl)-pyrimidine-5-carboxylic acid (1-cyano-piperidin-4-yl)-cyclopropyl-amide

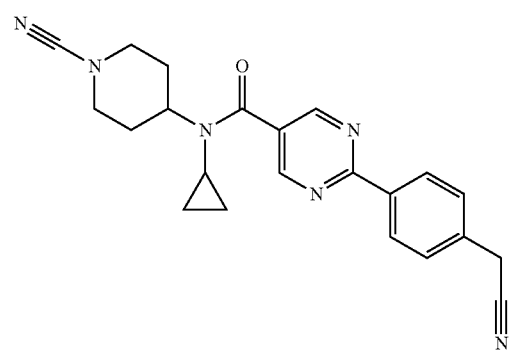 [SMILES: N#CCc1ccc(-c2ncc(C(=O)N(C3CC3)C3CCN(C#N)CC3)cn2)cc1]

The title compound is prepared from 2-(4-cyanomethyl-phenyl)-pyrimidine-5-carboxylic acid cyclopropyl-piperidin-4-yl amide following a procedure analogous to that described in Intermediate 12. LC (method 3): $t_R$=1.66 min; Mass spectrum (ESI$^+$): m/z=387 [M+H]$^+$.

Intermediate 15

2-(4-Cyano-3-fluoro-phenyl)-pyrimidine-5-carboxylic acid (1-cyano-piperidin-4-yl)-cyclopropyl-amide

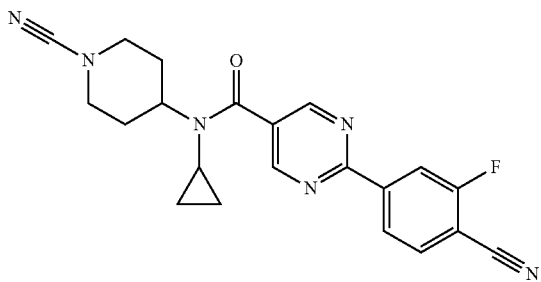 [SMILES: N#Cc1ccc(-c2ncc(C(=O)N(C3CC3)C3CCN(C#N)CC3)cn2)cc1F]

The title compound is prepared from 2-(4-cyano-3-fluoro-phenyl)-pyrimidine-5-carboxylic acid cyclopropyl-piperidin-4-yl-amide following a procedure analogous to that described in Intermediate 12. LC (method 3): $t_R$=1.85 min; Mass spectrum (ESI$^+$): m/z=391 [M+H]$^+$.

Intermediate 16

4-[Cyclopropyl-(2-imidazol-1-yl-pyrimidine-5-carbonyl)-amino]-piperidine-1-carboxylic acid tert-butyl ester

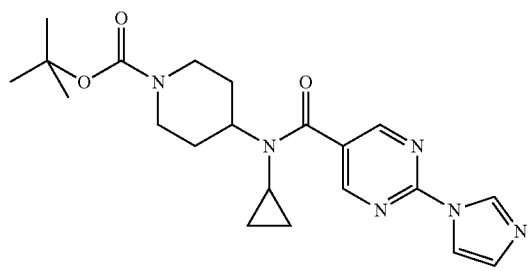 [SMILES: CC(C)(C)OC(=O)N1CCC(N(C(=O)c2cnc(-n3ccnc3)nc2)C2CC2)CC1]

A mixture of 4-[(2-chloro-pyrimidine-5-carbonyl)-cyclopropyl-amino]-piperidine-1-carboxylic acid tert-butyl ester (3.00 g), ethyldiisopropylamine (1.97 mL) and 1H-imidazole (520 mg) in N-methyl-2-pyrrolidinon (10 mL) is stirred over night at 100° C. After cooling to room temperature, water is added and the precipitate is filtered off and dried. LC (method 9): $t_R$=1.29 min; Mass spectrum (ESI$^+$): m/z=413 [M+H]$^+$.

Intermediate 17

2-Imidazol-1-yl-pyrimidine-5-carboxylic acid cyclopropyl-piperidin-4-yl-amide

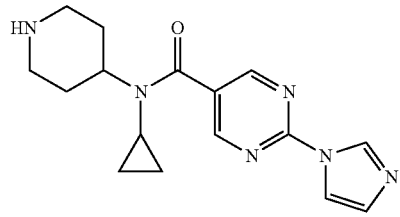 [SMILES: O=C(c1cnc(-n2ccnc2)nc1)N(C1CCNCC1)C1CC1]

The title compound is prepared from 4-[cyclopropyl-(2-imidazol-1-yl-pyrimidine-5-carbonyl)-amino]-piperidine-1-carboxylic acid tert-butyl ester by treatment with trifluoroacetic acid in dichloromethane. LC (method 10): $t_R$=0.68 min; Mass spectrum (ESI$^+$): m/z=313 [M+H]$^+$.

Intermediate 18

4-{Cyclopropyl-[2-(4-methanesulfonyl-phenyl)-pyrimidine-5-carbonyl]-amino}-piperidine-1-carboxylic acid tert-butyl ester

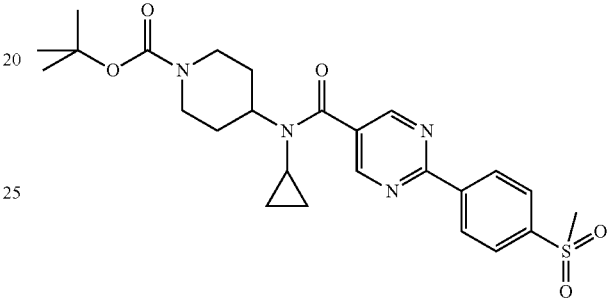

The title compound is prepared from 4-[(2-chloro-pyrimidine-5-carbonyl)-cyclopropyl-amino]-piperidine-1-carboxylic acid tert-butyl ester and 4-(methanesulfonyl)phenyl boronic acid following a procedure analogous to that described in Intermediate 6. LC (method 10): $t_R$=1.92 min; Mass spectrum (ESI$^-$): m/z=545 [M+HCOO]$^-$.

Intermediate 19

2-(4-Methanesulfonyl-phenyl)-pyrimidine-5-carboxylic acid cyclopropyl-piperidin-4-yl-amide

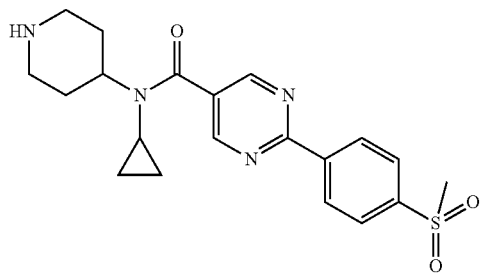 [SMILES: CS(=O)(=O)c1ccc(-c2ncc(C(=O)N(C3CCNCC3)C3CC3)cn2)cc1]

The title compound is prepared from 4-{cyclopropyl-[2-(4-methanesulfonyl-phenyl)-pyrimidine-5-carbonyl]-amino}-piperidine-1-carboxylic acid tert-butyl ester by treatment with trifluoroacetic acid in dichloromethane. LC (method 10): $t_R$=1.20 min; Mass spectrum (ESI+): m/z=401 [M+H]+.

Intermediate 20

2-(2-Methyl-imidazol-1-yl)-pyrimidine-5-carboxylic acid cyclopropyl-piperidin-4-yl-amide

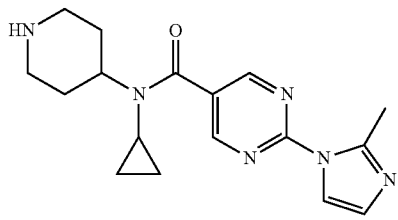 [SMILES: Cc1nccn1-c1ncc(C(=O)N(C2CCNCC2)C2CC2)cn1]

The title compound is prepared from 4-[(2-chloro-pyrimidine-5-carbonyl)-cyclopropyl-amino]-piperidine-1-carboxylic acid tert-butyl ester and 2-methyl-1H-imidazole following procedures analogous to those described in Intermediate 16 and Intermediate 17. LC (method 10): $t_R$=0.56 min; Mass spectrum (ESI+): m/z=327 [M+H]+.

Intermediate 21

2-(2-Ethyl-imidazol-1-yl)-pyrimidine-5-carboxylic acid cyclopropyl-piperidin-4-yl-amide

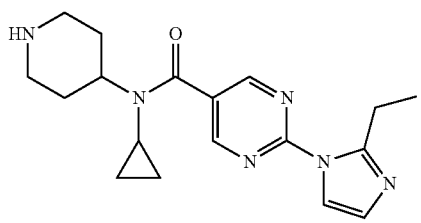 [SMILES: CCc1nccn1-c1ncc(C(=O)N(C2CCNCC2)C2CC2)cn1]

The title compound is prepared from 4-[(2-chloro-pyrimidine-5-carbonyl)-cyclopropyl-amino]-piperidine-1-carboxylic acid tert-butyl ester and 2-ethyl-1H-imidazole following procedures analogous to those described in Intermediate 16 and Intermediate 17. LC (method 10): $t_R$=0.56 min; Mass spectrum (ESI+): m/z=341 [M+H]+.

Intermediate 22

2-(4-Methanesulfonyl-phenyl)-pyrimidine-5-carboxylic acid (1-cyano-piperidin-4-yl)-cyclopropyl-amide

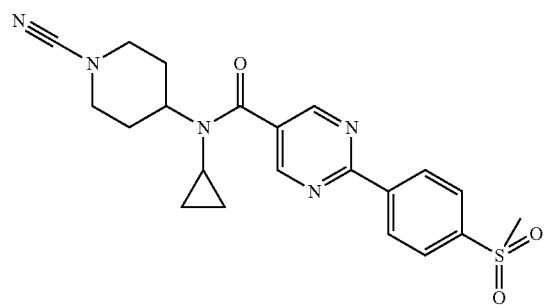 [SMILES: CS(=O)(=O)c1ccc(-c2ncc(C(=O)N(C3CC3)C3CCN(C#N)CC3)cn2)cc1]

The title compound is prepared from 2-(4-methanesulfonyl-phenyl)-pyrimidine-5-carboxylic acid cyclopropyl-piperidin-4-yl-amide following a procedure analogous to that described in Intermediate 12. LC (method 10): $t_R$=1.58 min; Mass spectrum (ESI+): m/z=426 [M+H]+.

Intermediate 23

8-(5-Ethyl-pyrimidin-2-yl)-1,4-dioxa-8-aza-spiro[4.5]decane

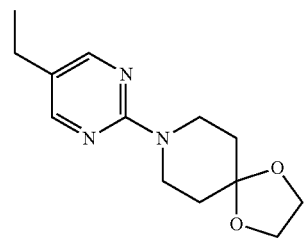 [SMILES: CCc1cnc(N2CCC3(CC2)OCCO3)nc1]

A mixture of 1,4-dioxa-8-aza-spiro[4.5]decane (11.08 mL), 2-chloro-5-ethylpyrimidine (7.50 mL), and ethyldiisopropylamine (15.50 mL) in tetrahydrofuran (60 mL) is heated under reflux for 30 min. After cooling to room temperature, the reaction mixture is diluted with dichloromethane and washed with 0.1 M citric acid and brine. The aqueous phase is basified with 1 M aqueous NaOH solution and extracted with dichloromethane. The combined organic phases are dried over MgSO$_4$ and the solvent is evaporated in vacuo to give the title compound. LC (method 11): $t_R$=1.10 min; Mass spectrum (ESI$^+$): m/z=250 [M+H]$^+$.

Intermediate 24

1-(5-Ethyl-pyrimidin-2-yl)-piperidin-4-one

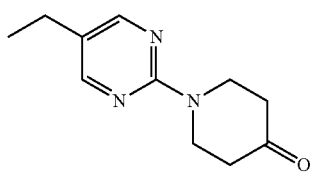

The title compound is prepared from 8-(5-ethyl-pyrimidin-2-yl)-1,4-dioxa-8-aza-spiro[4.5]decane following a procedure analogous to that described in Intermediate 3. LC (method 11): $t_R$=0.92 min; Mass spectrum (ESI$^+$): m/z=206 [M+H]$^+$.

Intermediate 25

Cyclopropyl-[1-(5-ethyl-pyrimidin-2-yl)-piperidin-4-yl] amine

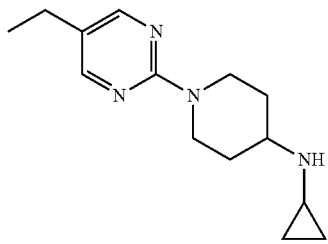 [SMILES: CCc1cnc(N2CCC(NC3CC3)CC2)nc1]

The title compound is prepared from 1-(5-ethyl-pyrimidin-2-yl)-piperidin-4-one and cyclopropylamine following a procedure analogous to that described in Intermediate 4. LC (method 12): $t_R$=2.53 min; Mass spectrum (ESI$^+$): m/z=247 [M+H]$^+$.

Intermediate 26

8-(3-Propyl-[1,2,4]oxadiazol-5-yl)-1,4-dioxa-8-aza-spiro[4.5]decane

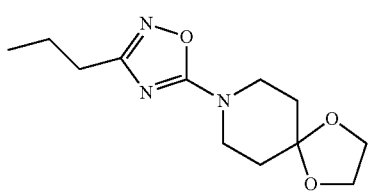 [SMILES: CCCc1noc(N2CCC3(CC2)OCCO3)n1]

The title compound is prepared from 1,4-dioxa-8-aza-spiro[4.5]decane-8-carbonitrile and N-hydroxy-butyramidine following a procedure analogous to that described in Intermediate 2. LC (method 14): $t_R$=1.16 min; Mass spectrum (ESI$^+$): m/z=254 [M+H]$^+$.

Intermediate 27

1-(3-Propyl-[1,2,4]oxadiazol-5-yl)-piperidin-4-one

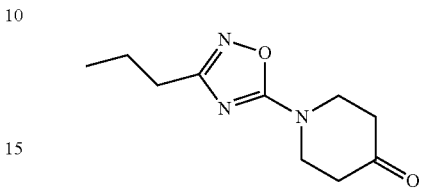

The title compound is prepared from 8-(3-propyl-[1,2,4] oxadiazol-5-yl)-1,4-dioxa-8-aza-spiro[4.5]decane following a procedure analogous to that described in Intermediate 3. LC (method 14): $t_R$=0.95 min; Mass spectrum (ESI$^+$): m/z=210 [M+H]$^+$.

Intermediate 28

Cyclopropyl-[1-(3-propyl-[1,2,4]oxadiazol-5-yl)-piperidin-4-yl]-amine

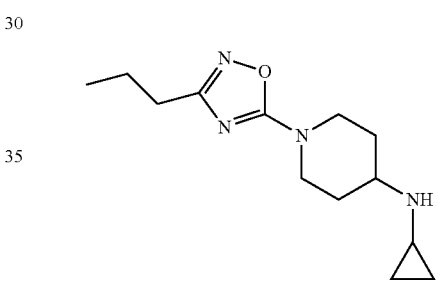

The title compound is prepared from 1-(3-propyl-[1,2,4] oxadiazol-5-yl)-piperidin-4-one following a procedure analogous to that described in Intermediate 4. LC (method 14): $t_R$=0.79 min; Mass spectrum (ESI$^+$): m/z=251 [M+H]$^+$.

Intermediate 29

5-(4-Cyano-2-fluoro-phenyl)-[1,2,4]oxadiazole-3-carboxylic acid ethyl ester

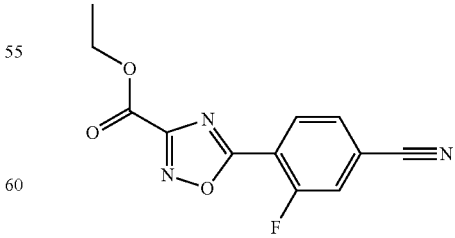

A solution of 4-cyano-2-fluorobenzoyl chloride (450 mg) in dichloromethane (5 mL) is added to a solution of amino-hydroxyimino-acetic acid ethyl ester (350 mg) in 2,6-dimethyl-pyridine (1 mL) and the reaction mixture is stirred at room temperature over night. Water is added and the organic phase is separated, washed with 1 N hydrochloric acid, water, and brine, dried over MgSO$_4$, and concentrated in vacuo. The dark residue is heated to 170° C. for 2 h. The crude product is purified by silica gel chromatography (cyclohexane/ethyl acetate 65:35). LC (method 15): t$_R$=1.08 min; Mass spectrum (ESI$^+$): m/z=262 [M+H]$^+$.

Intermediate 30

5-(4-Cyano-2-fluoro-phenyl)-[1,2,4]oxadiazole-3-carboxylic acid

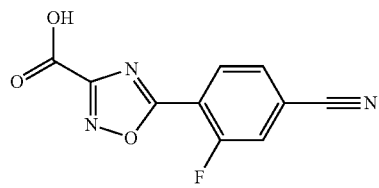 [SMILES: N#Cc1ccc(-c2nc(C(=O)O)no2)c(F)c1]

The title compound is prepared from 5-(4-cyano-2-fluoro-phenyl)-[1,2,4]oxadiazole-3-carboxylic acid ethyl ester by treatment with aqueous LiOH solution in tetrahydrofuran. LC (method 15): t$_R$=0.69 min; Mass spectrum (ESI$^+$): m/z=234 [M+H]$^+$.

Intermediate 31

2-(2-Methyl-imidazol-1-yl)-pyrimidine-5-carboxylic acid (1-cyano-piperidin-4-yl)-cyclopropyl-amide

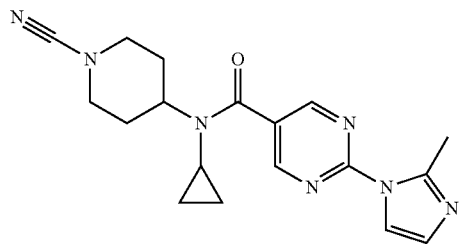 [SMILES: Cc1nccn1-c1ncc(C(=O)N(C2CC2)C2CCN(C#N)CC2)cn1]

To 2-(2-methyl-imidazol-1-yl)-pyrimidine-5-carboxylic acid cyclopropyl-piperidin-4-yl-amide (310 mg, Intermediate 20) and DIPEA (0.42 mL) in CH$_2$Cl$_2$ (10 mL) and THF (10 mL) is added bromocyane (120 mg) and the mixture is stirred at room temperature for 12 h. The mixture is concentrated, ethyl acetate and water are added, the organic layer is dried (MgSO$_4$) and concentrated to yield the title compound. LC (method 3): t$_R$=1.07 min; Mass spectrum (ESI$^+$): m/z=352 [M+H]$^+$.

Intermediate 32

2-(2-Ethyl-imidazol-1-yl)-pyrimidine-5-carboxylic acid (1-cyano-piperidin-4-yl)-cyclopropyl-amide

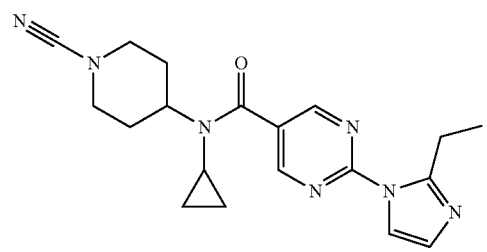 [SMILES: CCc1nccn1-c1ncc(C(=O)N(C2CC2)C2CCN(C#N)CC2)cn1]

The title compound is prepared from 2-(2-ethyl-imidazol-1-yl)-pyrimidine-5-carboxylic acid cyclopropyl-piperidin-4-yl-amide (Intermdiate 21) following a procedure analogous to that described in Intermediate 31. LC (method 3): t$_R$=1.16 min; Mass spectrum (ESI$^+$): m/z=366 [M+H]$^+$.

Intermediate 33

2-Imidazol-1-yl-pyrimidine-5-carboxylic acid (1-cyano-piperidin-4-yl)-cyclopropyl-amide

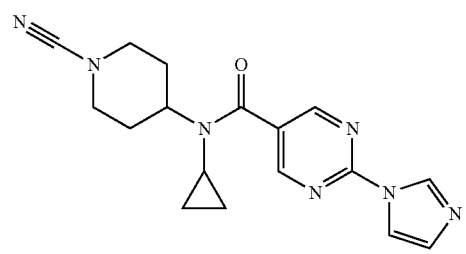 [SMILES: N#CN1CCC(N(C(=O)c2cnc(-n3ccnc3)nc2)C2CC2)CC1]

The title compound is prepared from 2-imidazol-1-yl-pyrimidine-5-carboxylic acid cyclopropyl-piperidin-4-yl-amide (Intermediate 17) following a procedure analogous to that described in Intermediate 31. LC (method 16): t$_R$=0.93 min; Mass spectrum (ESI$^+$): m/z=338 [M+H]$^+$.

Intermediate 34

8-(3-Isopropyl-[1,2,4]oxadiazol-5-yl)-1,4-dioxa-8-aza-spiro[4.5]decane

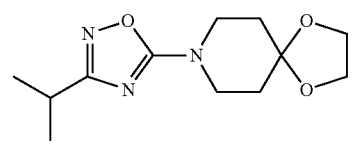 [SMILES: CC(C)c1noc(N2CCC3(CC2)OCCO3)n1]

The title compound is prepared from 1,4-dioxa-8-aza-spiro[4.5]decane-8-carbonitrile and N-hydroxy-isobutyramidine following a procedure analogous to that described in Intermediate 2. LC (method 17): $t_R$=1.56 min; Mass spectrum (ESI$^+$): m/z=254 [M+H]$^+$.

Intermediate 35

1-(3-Isopropyl-[1,2,4]oxadiazol-5-yl)-piperidin-4-one

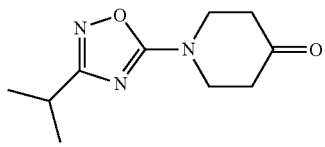

The title compound is prepared from 8-(3-isopropyl-[1,2,4]oxadiazol-5-yl)-1,4-dioxa-8-aza-spiro[4.5]decane following a procedure analogous to that described in Intermediate 3. Mass spectrum (ESI$^+$): m/z=210 [M+H]$^+$.

Intermediate 36

Cyclopropyl-[1-(3-isopropyl-[1,2,4]oxadiazol-5-yl)-piperidin-4-yl]-amine

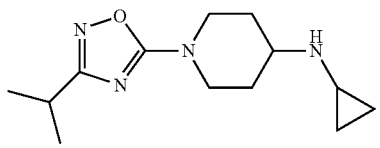 [SMILES: CC(C)c1noc(N2CCC(NC3CC3)CC2)n1]

The title compound is prepared from 1-(3-isopropyl-[1,2,4]oxadiazol-5-yl)-piperidin-4-one and cyclopropylamine following a procedure analogous to that described in Intermediate 4. Mass spectrum (ESI$^+$): m/z=251 [M+H]$^+$.

Intermediate 37

3-(4-Cyano-2-fluoro-phenyl)-5-methoxy-4,5-dihydro-isoxazole-5-carboxylic acid methyl ester

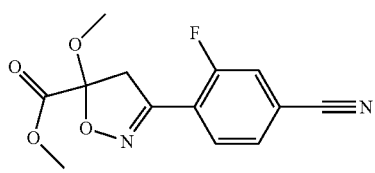 [SMILES: COC(=O)C1(OC)CC(c2ccc(C#N)cc2F)=NO1]

Triethylamine (1.05 mL) is added drop wise to a mixture of (4-cyano-2-fluoro-benzaldehyde chlorooxime (600 mg) and 2-methoxyacrylate (421 mg) in dichloromethane (7.5 mL). The reaction mixture is stirred over night at room temperature. Water is added and the aqueous phase is extracted with ethyl acetate. The combined organic phases are washed with brine, dried over MgSO$_4$, and concentrated in vacuo. The residue is chromatographed on silica gel (cyclohexane/ethyl acetate 80:20→50:50) to afford the title compound. LC (method 18): $t_R$=0.93 min; Mass spectrum (ESI$^+$): m/z=279 [M+H]$^+$.

Intermediate 38

3-(4-Cyano-2-fluoro-phenyl)-isoxazole-5-carboxylic acid

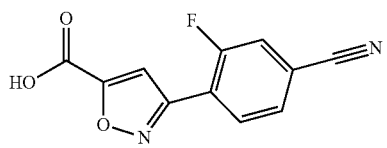 [SMILES: N#Cc1ccc(-c2cc(C(=O)O)on2)c(F)c1]

A mixture of 3-(4-cyano-2-fluoro-phenyl)-5-methoxy-4,5-dihydro-isoxazole-5-carboxylic acid methyl ester (172 mg), 1N aqueous NaOH solution (2 mL), and tetrahydrofuran (5 mL) is stirred at room temperature for 3 h. The reaction mixture is acidified with 1 N hydrochloric acid (approximately pH 3) and concentrated in vacuo. The residue is triturated with water and the precipitate is filtered off and dried to give the title compound. LC (method 18): $t_R$=0.38 min; Mass spectrum (ESI$^-$): m/z=231 [M−H]$^-$.

Intermediate 39

5-(4-Cyano-2-fluoro-phenyl)-isoxazole-3-carboxylic acid ethyl ester

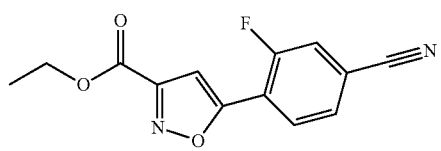 [SMILES: CCOC(=O)c1cc(-c2ccc(C#N)cc2F)on1]

A mixture of 5-chloro-isoxazole-3-carboxylic acid ethyl ester (600 mg), 4-cyano-2-fluorophenylboronic acid (665 mg), and aqueous Na$_2$CO$_3$ solution (2 M; 4.41 mL) in 1,4-dioxane (15 mL) is purged with argon for 15 min prior to the addition of Pd(PPh$_3$)$_4$ (276 mg). The reaction mixture is heated under an argon atmosphere to 140° C. for 20 min in a microwave oven. The solvent is evaporated in vacuo and the residue is mixed with water and ethyl acetate. The aqueous phase is extracted with ethyl acetate and the combined extracts are washed with brine, dried over MgSO$_4$ and concentrated in vacuo. The crude product is purified by silica gel chromatography (cyclohexane/ethyl acetate 80:20→50:50). LC (method 19): $t_R$=1.50 min; Mass spectrum (ESI$^+$): m/z=261 [M+H]$^+$.

Intermediate 40

5-(4-Cyano-2-fluoro-phenyl)-isoxazole-3-carboxylic acid

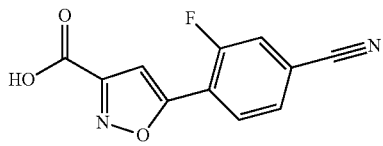 [SMILES: N#Cc1ccc(-c2cc(C(=O)O)no2)c(F)c1]

The title compound is prepared from 5-(4-cyano-2-fluoro-phenyl)-isoxazole-3-carboxylic acid ethyl ester by treatment with aqueous NaOH solution in tetrahydrofuran. LC (method 18): $t_R$=0.32 min; Mass spectrum (EI): m/z=232 [M]$^+$.

Intermediate 41

8-(3-tert-Butyl-[1,2,4]oxadiazol-5-yl)-1,4-dioxa-8-aza-spiro[4.5]decane

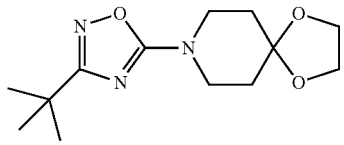 [SMILES: CC(C)(C)c1noc(N2CCC3(CC2)OCCO3)n1]

The title compound is prepared from 1,4-dioxa-8-aza-spiro [4.5]decane-8-carbonitrile and N-hydroxy-2,2-dimethyl-propionamidine following a procedure analogous to that described in Intermediate 2. LC (method 8): $t_R$=1.53 min; Mass spectrum (ESI$^+$): m/z=268 [M+H]$^+$.

Intermediate 42

1-(3-tert-Butyl-[1,2,4]oxadiazol-5-yl)-piperidin-4-one

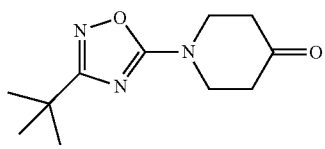 [SMILES: CC(C)(C)c1noc(N2CCC(=O)CC2)n1]

The title compound is prepared from 8-(3-tert-Butyl-[1,2,4]oxadiazol-5-yl)-1,4-dioxa-8-aza-spiro[4.5]decane follow-ing a procedure analogous to that described in Intermediate 3. LC (method 8): $t_R$=1.31 min, Mass spectrum (ESI$^+$): m/z=224 [M+H]$^+$.

Intermediate 43

[1-(3-tert-Butyl-[1,2,4]oxadiazol-5-yl)-piperidin-4-yl]-cyclopropyl-amine

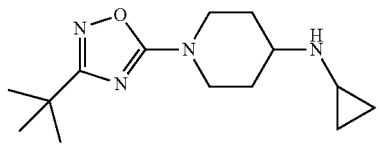 [SMILES: CC(C)(C)c1noc(N2CCC(NC3CC3)CC2)n1]

The title compound is prepared from 1-(3-tert-butyl-[1,2,4]oxadiazol-5-yl)-piperidin-4-one and cyclopropylamine following a procedure analogous to that described in Intermediate 4. LC (method 8): $t_R$=0.95 min, Mass spectrum (ESI$^+$): m/z=265 [M+H]$^+$.

Intermediate 44

5-Oxazol-5-yl-pyrazine-2-carboxylic acid

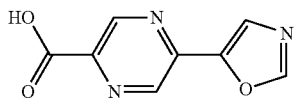 [SMILES: O=C(O)c1cnc(-c2cnco2)cn1]

Aqueous Na$_2$CO$_3$ solution (2 M, 14.5 mL) and [1,1'-bis (diphenylphosphino)-ferrocene]dichloropalladium dichloromethane complex (950 mg) are added to a mixture of 5-chloropyrazine-2-carboxylic acid methyl ester (2.00 g) and 5-(4,4,5,5-tetramethyl-1,3,2-dioxaborolan-2-yl)-2-[tris(isopropyl)silyl]-oxazole (4.70 g) in N,N-dimethylformamide (20 mL) under an argon atmosphere. The reaction mixture is stirred overnight at 80° C. After cooling to room temperature, the solvents are evaporated, the residue is mixed water and acidified with 4 N hydrochloric acid (12 mL). A precipitate is formed upon addition of ethyl acetate, which is filtered off, washed with ethyl acetate and methanol, and dried. LC (method 7): $t_R$=0.46 min; Mass spectrum (ESI$^-$): m/z=190 [M−H]$^-$.

Intermediate 45

6-Oxazol-5-yl-nicotinic acid

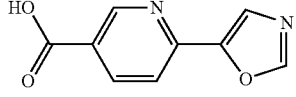 [SMILES: O=C(O)c1ccc(-c2cnco2)nc1]

The title compound is prepared from 6-bromo-nicotinic acid and 5-(4,4,5,5-tetramethyl-1,3,2-dioxaborolan-2-yl)-2-[tris(isopropyl)silyl]-oxazole and following a procedure analogous to that described in Intermediate 45. Mass spectrum (ESI+): m/z=189 [M–H]−.

Intermediate 46

1-(5-Ethyl-pyrazin-2-yl)-piperidin-4-ol

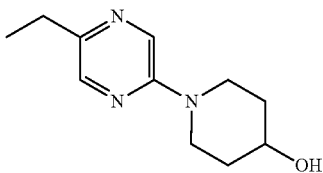

A mixture of 2-bromo-5-ethyl-pyrazine (1.66 g) and 4-hydroxy-piperidine (2.24 g) in isopropanol (15 mL) is heated in an autoclave to 150° C. over night. The solvent is evaporated in vacuo and the residue is mixed with water and dichloromethane. The aqueous phase is extracted with dichloromethane and the combined organic phases are washed with brine, dried over MgSO$_4$, and concentrated in vacuo to give the title compound. LC (method 7): t$_R$=0.66 min; Mass spectrum (ESI+): m/z=208 [M+H]+.

Intermediate 47

1-(5-Ethyl-pyrazin-2-yl)-piperidin-4-one

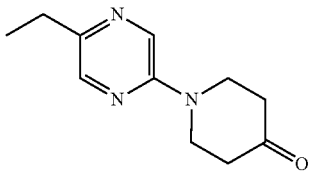

The title compound is prepared from 1-(5-ethyl-pyrazin-2-yl)-piperidin-4-ol by oxidation with Dess-Martin periodinane in dichloromethane at room temperature. LC (method 7): t$_R$=0.73 min; Mass spectrum (ESI+): m/z=206 [M+H]+.

Intermediate 48

Cyclopropyl-[1-(5-ethyl-pyrazin-2-yl)-piperidin-4-yl]-amine

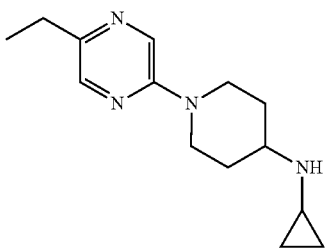 [SMILES: CCc1cnc(N2CCC(NC3CC3)CC2)cn1]

The title compound is prepared from 1-(5-ethyl-pyrazin-2-yl)-piperidin-4-one and cyclopropylamine following a procedure analogous to that described in Intermediate 4. LC (method 7): t$_R$=0.65 min; Mass spectrum (ESI+): m/z=247 [M+H]+.

Intermediate 49

1-(5-Methyl-pyrimidin-2-yl)-piperidin-4-ol

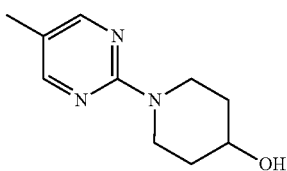

The title compound is prepared from 2-chloro-5-methyl-pyrimidne and 4-hydroxy-piperidine following a procedure analogous to that described in Intermediate 47. LC (method 7): t$_R$=0.48 min; Mass spectrum (ESI+): m/z=194 [M+H]+.

Intermediate 50

1-(5-Methyl-pyrimidin-2-yl)-piperidin-4-one

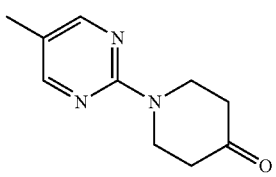

The title compound is prepared from 1-(5-methyl-pyrimidin-2-yl)-piperidin-4-ol following a procedure analogous to that described in Intermediate 48. LC (method 7): t$_R$=0.54 min; Mass spectrum (ESI+): m/z=192 [M+H]+.

Intermediate 51

Cyclopropyl-[1-(5-methyl-pyrimidin-2-yl)-piperidin-4-yl]amine

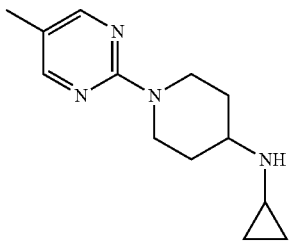 [SMILES: Cc1cnc(N2CCC(NC3CC3)CC2)nc1]

The title compound is prepared from 1-(5-methyl-pyrimidin-2-yl)-piperidin-4-one and cyclopropylamine following a procedure analogous to that described in Intermediate 4. LC (method 7): $t_R$=0.55 min; Mass spectrum (ESI$^+$): m/z=233 [M+H]$^+$.

Intermediate 52

1-(5-Methyl-pyrazin-2-yl)-piperidin-4-ol

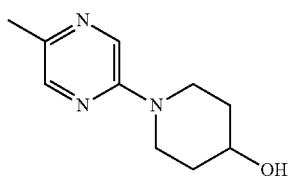

The title compound is prepared from 2-bromo-5-methyl-pyrazine and 4-hydroxy-piperidine following a procedure analogous to that described in Intermediate 47. LC (method 8): $t_R$=0.94 min; Mass spectrum (ESI$^+$): m/z=194 [M+H]$^+$.

Intermediate 53

1-(5-Methyl-pyrazin-2-yl)-piperidin-4-one

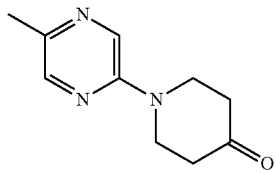

The title compound is prepared from 1-(5-methyl-pyrazin-2-yl)-piperidin-4-ol following a procedure analogous to that described in Intermediate 48. LC (method 7): $t_R$=0.56 min; Mass spectrum (ESI$^+$): m/z=192 [M+H]$^+$.

Intermediate 54

Cyclopropyl-[1-(5-methyl-pyrazin-2-yl)-piperidin-4-yl]-amine

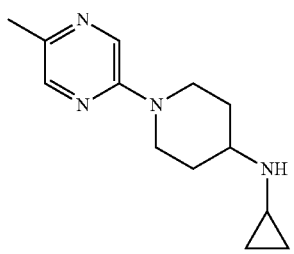 [SMILES: Cc1cnc(N2CCC(NC3CC3)CC2)cn1]

The title compound is prepared from 1-(5-methyl-pyrazin-2-yl)-piperidin-4-one and cyclopropylamine following a procedure analogous to that described in Intermediate 4. LC (method 7): $t_R$=0.68 min; Mass spectrum (ESI$^+$): m/z=233 [M+H]$^+$.

Intermediate 55

6-(2-Methyl-1H-imidazol-1-yl)pyridine-3-carboxylic acid

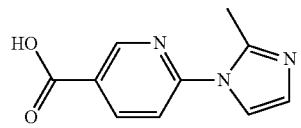

A mixture of methyl 6-chloropyridine-3-carboxylate (0.75 g), N,N-diisopropyl-ethyl-amine (1.75 mL) and 2-methyl-1H-imidazole (0.58 g) in N-methylpyrrolidone (6 mL) is heated to 100° C. overnight. Additional 2-methyl-1H-imidazole (0.58 g) is added and the reaction continues at 100° C. for two days. Ethyl acetate is added and the mixture is washed with saturated ammonium chloride. The organic phase is dried over MgSO$_4$ and concentrated in vacuo. The crude ester is dissolved in MeOH (4 mL) and KOH (1.5 g) in water (2 mL) is added and kept at room temperature for 2 h. The MeOH is removed in vacuo and the aqueous phase is acidified with 1N HCl and extracted with dichloromethane. The organic phase is dried over MgSO$_4$ and concentrated to afford the title compound. LC (method 20): $t_R$=0.51 min; Mass spectrum (APCI): m/z=204 [M+H]$^+$.

Intermediate 56

5-(2-Methyl-1H-imidazol-1-yl)pyrazine-2-carboxylic acid

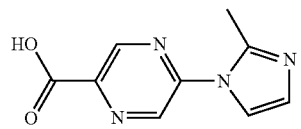

A mixture of methyl 5-chloropyrazine-2-carboxylate (0.75 g), K$_2$CO$_3$ (1.8 g) and 2-methyl-1H-imidazole (1.3 g) in N,N-dimethylformamide (6 mL) is heated to 100° C. overnight. Analysis of the crude mixture by LCMS shows saponified product. The solvents are evaporated and the crude product is purified by HPLC. LC (method 20): $t_R$=0.27 min; Mass spectrum (APCI): m/z=205 [M+H]$^+$.

Intermediate 57

5-(1H-1,2,4-Triazol-1-yl)pyrazine-2-carboxylic acid

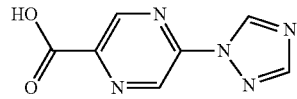

A mixture of methyl 5-chloropyrazine-2-carboxylate (0.75 g), K$_2$CO$_3$ (1.8 g) and 1H-1,2,4-triazole (1.2 g) in N,N-dimethylformamide (6 mL) is heated to 100° C. overnight. Analysis of the crude mixture by LCMS shows saponified product. The product is acidified with 1N HCl and the precipitate is filtered and washed with water and diethyl ether to afford the title compound. LC (method 20): $t_R$=1.06 min; Mass spectrum (APCI): m/z=192 [M+H]$^+$.

Intermediate 58

5-(3-Methyl-1H-1,2,4-triazol-1-yl)pyrazine-2-carboxylic acid

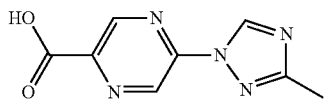

A mixture of methyl 5-chloropyrazine-2-carboxylate (0.75 g), K$_2$CO$_3$ (1.8 g) and 3-methyl-1H-1,2,4-triazole (1.2 g) in N,N-dimethylformamide (6 mL) is heated to 100° C. overnight. Analysis of the crude mixture by LCMS shows saponified product. The product is acidified with 1N HCl and the precipitate is filtered and washed with water and diethyl ether to afford the title compound. LC (method 20): $t_R$=1.21 min; Mass spectrum (APCI): m/z=206 [M+H]$^+$.

Intermediate 59

6-(5-Methyl-1H-1,2,3,4-tetrazol-1-yl)pyridine-3-carboxylic acid

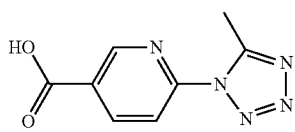

To a solution of methyl 6-aminopyridine-3-carboxylate (1.52 g) in dichloromethane (10 mL) and pyridine (3 mL) is added acetic anhydride (2 g) and the solution is stirred at r.t. overnight. After concentration water and dichloromethane are added and the organic layer is separated, washed with saturated aqueous CuSO$_4$, then water, dried over MgSO$_4$ and concentrated. The N-acyl compound is dissolved in MeCN (20 mL) and sodium azide (4 g) and SiCl$_4$ (4 mL) are added and the mixture is stirred at r.t. overnight. The reaction is quenched by slow addition to an ice/NaHCO$_3$ mixture and extracted with ethyl acetate. The organic extracts are dried over MgSO$_4$ and concentrated. The crude ester is dissolved in MeOH (30 mL) and 4 M NaOH (3 mL) is added and stirred at r.t. for 2 h. The mixture is neutralized to pH 7 with 6 M HCl, concentrated and then acidified with 6 M HCl and the precipitate is filtered off washing with water and dried by suction to give the title compound. LC (method 20): $t_R$=1.52 min; Mass spectrum (APCI): m/z=206 [M+H]$^+$.

Intermediate 60

2-(5-Methyl-1H-1,2,4-triazol-1-yl)pyrimidine-5-carboxylic acid

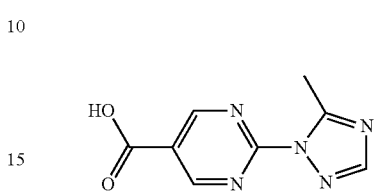

2-Chloropyrimidine-5-carboxylic acid (1.5 g) is dissolved in MeOH (25 mL) and hydrazine (5 mL) is added at r.t. An exothermic reaction occurs and a solid precipitate forms. The solid is filtered off washing with a little MeOH and is dried by suction to give the hydrazine intermediate. The hydrazine is dissolved in acetic acid (4 mL) and N-((dimethylamino)methylene)acetamide [made from acetamide and N,N-dimethylformamide-dimethylacetal by procedure in US2007/0111984A1] (2.0 g) is added and heated at 90° C. for 1 h. After cooling and concentrating the residue is purified by HPLC to give the title compound. LC (method 20): $t_R$=1.24 min; Mass spectrum (APCI): m/z=206 [M+H]$^+$.

Intermediate 61

6-(5-methyl-1H-1,2,4-triazol-1-yl)pyridine-3-carboxylic acid

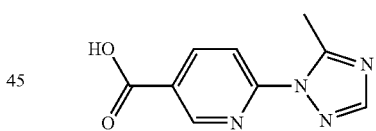

2-Chloro-5-cyanopyridine (1.5 g) is dissolved in hydrazine (6 mL) at r.t. and an exothermic reaction occurs and a solid precipitate forms. Water is added and the solid is filtered off washing with water and is dried by suction to give the hydrazine intermediate. The hydrazine is suspended in acetic acid (7 mL) and N-((dimethylamino)methylene)acetamide [made from acetamide and DMF-dimethylacetal by procedure in US2007/0111984A1] (700 mg) is added and heated at 90° C. for 5.5 h. Additional N-((dimethylamino)methylene)acetamide (200 mg) is added and the mixture is heated at 90° C. for 3 h. After cooling and concentrating the residue is purified by chromatography on silica gel eluting with 0% to 100% ethyl acetate/hexane to give the intermediate nitrile. The nitrile is dissolved in MeOH (10 mL) and 4 M NaOH (2 mL) is added and heated at 65° C. for 16 h. The mixture is neutralized with 6 M HCl, concentrated, and then acidified to pH 2 with 6 M HCl. The precipitate is filtered off washing with water and dried by suction to give the title compound. LC (method 20): t$_R$=1.53 min; Mass spectrum (APCI): m/z=205 [M+H]$^+$.

Intermediate 62

1-(4-Cyano-2-fluorophenyl)-1H-imidazole-4-carboxylic acid

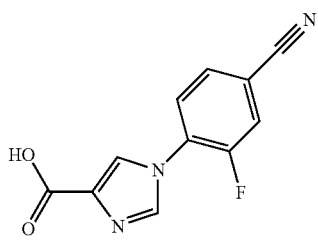 [SMILES: N#Cc1ccc(-n2cnc(C(=O)O)c2)c(F)c1]

A mixture of 1H-imidazole-4-carboxylic acid (500 mg), 4-fluoro-3-fluorobenzonitrile (0.93 g), and N,N-diisopropyl-ethyl amine (3.6 mL) in N,N-dimethylformamide (6 mL) is heated to 120° C. overnight. The crude product is purified by HPLC. LC (method 20): t$_R$=1.85 min; Mass spectrum (APCI): m/z=232 [M+H]$^+$.

Intermediate 63

1-(5-Cyanopyridin-2-yl)-1H-imidazole-4-carboxylic acid

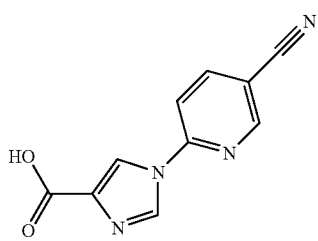 [SMILES: N#Cc1ccc(-n2cnc(C(=O)O)c2)nc1]

A mixture of 1H-imidazole-4-carboxylic acid (500 mg), 6-chloropyridine-3-carbonitrile (0.93 g), and N,N-diisopropyl-ethyl-amine (3.6 mL) in N,N-dimethylformamide (6 mL) is heated to 120° C. overnight. The crude product is purified by HPLC. LC (method 20): t$_R$=1.73 min; Mass spectrum (APCI): m/z=215 [M+H]$^+$.

Intermediate 64

1-(2-Fluoro-4-methanesulfonylphenyl)-1H-imidazole-4-carboxylic acid

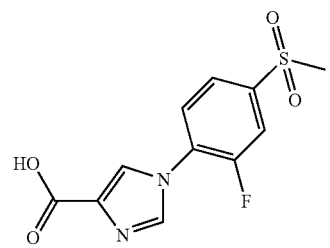 [SMILES: CS(=O)(=O)c1ccc(-n2cnc(C(=O)O)c2)c(F)c1]

A mixture of 1H-imidazole-4-carboxylic acid (500 mg), 1,2-difluoro-4-methanesulfonylbenzene (1.2 g), and N,N-di-isopropyl-ethyl-amine (4 mL) in N,N-dimethylformamide (6 mL) is heated to 120° C. overnight. The crude product is purified by HPLC. LC (method 20): t$_R$=1.69 min; Mass spectrum (APCI): m/z=285 [M+H]$^+$.

Intermediate 65

1-(4-Cyano-2-fluorophenyl)-2-methyl-1H-imidazole-4-carboxylic acid

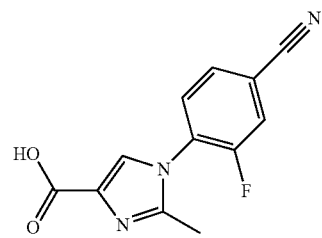 [SMILES: Cc1nc(C(=O)O)cn1-c1ccc(C#N)cc1F]

A mixture of 2-methyl-1H-imidazole-4-carboxylic acid (400 mg), 4-fluoro-3-fluorobenzonitrile (0.53 g), and K$_2$CO$_3$ (1.3 g) in N,N-dimethylformamide (6 mL) is heated to 100° C. for 30 minutes in a microwave. The crude product is Intermediate 65

1-(5-Cyanopyridin-2-yl)-2-methyl-1H-imidazole-4-carboxylic acid

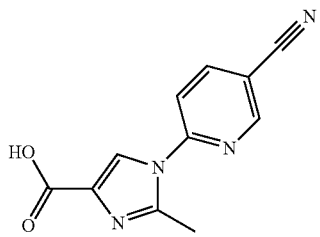 [SMILES: Cc1nc(C(=O)O)cn1-c1ccc(C#N)cn1]

A mixture of 2-methyl-1H-imidazole-4-carboxylic acid (490 mg), 6-chloropyridine-3-carbonitrile (800 mg), and $K_2CO_3$ (1.1 g) in DMF (6 mL) is heated to 100° C. overnight. The crude product is purified by HPLC. LC (method 20): $t_R$=0.73 min; Mass spectrum (APCI): m/z=229 [M+H]$^+$.

Intermediate 66

1-(2-Fluoro-4-methanesulfonylphenyl)-2-methyl-1H-imidazole-4-carboxylic acid

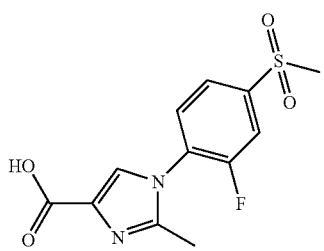 [SMILES: Cc1nc(C(=O)O)cn1-c1ccc(S(C)(=O)=O)cc1F]

A mixture of 2-methyl-1H-imidazole-4-carboxylic acid (500 mg), N,N-diisopropyl-ethyl-amine (4 mL), and 1,2-difluoro-4-methanesulfonylbenzene (1.2 g), in N,N-dimethylformamide (6 mL) is heated to 120° C. overnight. The crude product is purified by HPLC. LC (method 20): $t_R$=0.90 min; Mass spectrum (APCI): m/z=299 [M+H]$^+$.

Intermediate 67

2-(2-Methyl-1H-imidazol-1-yl)pyrimidine-5-carboxylic acid

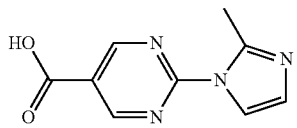

2-Chloropyrimidine-5-carboxylic acid (0.75 g), 2-methylimidazole (0.117 g) and potassium carbonate (1.96 g) in 3.75 mL of N,N-dimethylformamide are heated in microwave at 50° C. for 30 min, then cooled to room temperature and acidified with 3 mL of 1 N HCl, followed by addition of conc. HCl to pH 2. The precipitate is filtered, washed with minimum amount of water, diethyl ether and dried in vacuo to afford the title compound. LC (method 20): $t_R$=0.48 min; Mass spectrum (APCI): m/z=205 [M+H]$^+$.

Intermediate 68

2-(1H-1,2,4-Triazol-1-yl)pyrimidine-5-carboxylic acid

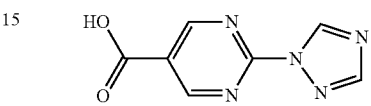

2-Chloropyrimidine-5-carboxylic acid (0.75 g), 1,2,4-1H-triazole (0.98 g) and potassium carbonate (1.96 g) in 3.75 mL of N,N-dimethylformamide are heated in microwave at 50° C. for 30 min, then cooled to room temperature and acidified with 3 mL of 1N HCl, followed by addition of conc. HCl to pH 2. The precipitate is filtered, washed with minimum amount of water, diethyl ether and dried in vacuo to afford the title compound. LC (method 20): $t_R$=0.82 min; Mass spectrum (APCI): m/z=192 [M+H]$^+$.

Intermediate 69

4-Hydroxypiperidine-1-carbonitrile

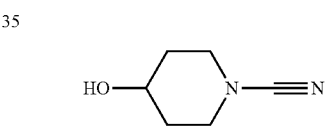

4-Hydroxypiperidine (10 g) is dissolved in 20 ml dichloromethane and added dropwise to a solution of $NaHCO_3$ (16.6 g) in $H_2O$ (10 ml) at 0° C. The mixture is stirred at 0° C. for 30 min then 3 M cyanogen bromide (36.3 ml) is added. The mixture is stirred at 0° C. for 30 min then warmed to room temperature for 12 h. The mixture is diluted with dichloroemthane (30 ml) and extracted. The organic layer is washed with brine (15 ml), dried over $MgSO_4$, filtered and concentrated. The crude product is purified by silica gel chromatography (0% to 100% ethyl acetate/hexanes) to afford the title compound. LC (method 20): $t_R$=0.49 min; Mass spectrum (APCI): m/z=127 [M+H]$^+$.

Intermediate 70

N-Hydroxy-2-methylpropanimidamide

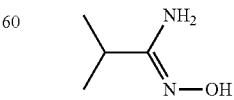

Isobutyronitrile (5 ml) and 50% hydroxylamine in $H_2O$ (15 ml) are combined in a sealed tube and heated to 80° C. for 4 h. The mixture is concentrated and dried under high vacuum overnight to yield N-hydroxy-2-methylpropanimidamide (4.7 g) which was used without further purification.

Intermediate 71

1-[3-(Propan-2-yl)-1,2,4-oxadiazol-5-yl]piperidin-4-ol

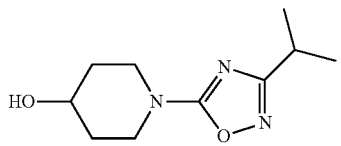

4-Hydroxypiperidine-1-carbonitrile (3.0 g) and N-hydroxy-2-methylpropanimidamide (2.9 g) are dissolved in ethyl acetate (20 ml) and 1 M $ZnCl_2$ in $Et_2O$ (29 ml) is added. A precipitate forms and the solvent is decanted off. Additional $Et_2O$ (20 ml) is added to wash the precipitate and is decanted off. EtOH (20 ml) is added followed by conc. HCl (7.5 ml) and the mixture is heated to 100° C. for 3.5 h. The mixture is concentrated, redissolved in $H_2O$ (5 ml) and made basic by addition of concentrated $NaHCO_3$. The aqueous layer is extracted with dichloromethane (2×50 mL) and the organic layer is dried over $MgSO_4$, filtered and concentrated. The crude product is purified by silica gel chromatography (0% to 100% ethyl acetate/hexanes) to afford the title compound. LC (method 20): $t_R$=1.56 min; Mass spectrum (APCI): m/z=212 [M+H]$^+$.

Intermediate 72

1-[3-(Propan-2-yl)-1,2,4-oxadiazol-5-yl]piperidin-4-one

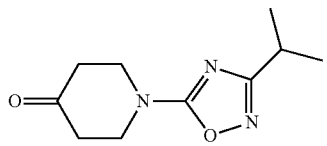

1-[3-(Propan-2-yl)-1,2,4-oxadiazol-5-yl]piperidin-4-ol (0.5 g) is dissolved in dichloromethane (75 mL) and 4 A molecular sieves (4 g) are added followed by N-methylmorpholine-N-oxide (1.52 g) and tetrapropylammonium perrhutenate (0.018 g) and the mixture is stirred at room temperature for 1 h. The reaction is then filtered through celite and the mother liquor washed with water (2×50 mL). The water layers are then combined and back extracted with dichloroemthane (100 mL). The dichloromethane layers are combined, dried over $Na_2SO_4$, filtered and concentrated to give the title compound. LC (method 20): $t_R$=1.67 min; Mass spectrum (APCI): m/z=210 [M+H]$^+$.

Intermediate 73

8-(5-Chloropyrimidin-2-yl)-1,4-dioxa-8-azaspiro[4.5]decane

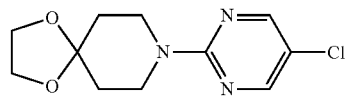 [SMILES: Clc1cnc(N2CCC3(CC2)OCCO3)nc1]

1,4-Dioxa-8-azaspiro[4.5]decane (2.39 g) is combined with 2,5-dichloropyrimidine (2.44 g) in N,N-dimethylformamide (50 mL), 1,4-dioxane (75 mL) and triethylamine (6.7 mL) in a glass pressure reaction vessel and heated with stirring at 120° C. for 16 h. After cooling the orange solution is concentrated and partitioned between dichloromethane (100 mL) and water (100 mL). The water layer is extracted with dichloromethane (100 mL). The dichloromethane layers are combined, washed with water (2×100 mL), dried over $Na_2SO_4$, filtered and concentrated to give the title compound. LC (method 20): $t_R$=2.24 min; Mass spectrum (APCI): m/z=256 [M+H]$^+$.

Intermediate 74

8-[3-Fluoro-5-(trifluoromethyl)pyridin-2-yl]-1,4-dioxa-8-azaspiro[4.5]decane

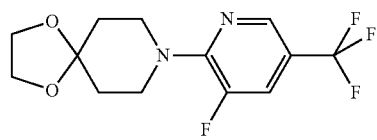 [SMILES: Fc1cc(C(F)(F)F)cnc1N1CCC2(CC1)OCCO2]

1,4-Dioxa-8-azaspiro[4.5]decane (1.76 g), 2-bromo-3-fluoro-5-(trifluoromethyl)-pyridine (2.95 g), N,N-dimethylformamide (50 mL), 1,4-dioxane (75 mL) and triethylamine (5.07 ml) are heated in a sealed vessel at 120° C. with stirring for 1 h. After cooling the mixture is concentrated and partitioned between ethyl acetate (100 mL) and water (100 mL). The water layer is extracted with ethyl acetate (100 mL) and the combined ethyl acetate layers are dried over $Na_2SO_4$, filtered and concentrated to give the title compound. LC (method 21): $t_R$=7.59 min; Mass spectrum (APCI): m/z=307 [M+H]$^+$.

Intermediate 75

8-(5-Ethylpyrimidin-2-yl)-1,4-dioxa-8-azaspiro[4.5]decane

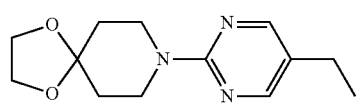 [SMILES: CCc1cnc(N2CCC3(CC2)OCCO3)nc1]

1,4-Dioxa-8-azaspiro[4.5]decane (1.76 g), 2-chloro-5-ethylpyrimidine (1.7 g), N,N-dimethylformamide (50 mL), 1,4- dioxane (75 mL) and triethylamine (5.07 ml) are heated in a sealed vessel at 120° C. with stirring for 22 h. After cooling the mixture is concentrated and partitioned between ethyl acetate (100 mL) and water (100 mL). The water layer is extracted with ethyl acetate (100 mL) and the combined ethyl acetate layers are dried over Na$_2$SO$_4$, filtered and concentrated to give the title compound. LC (method 20): t$_R$=1.73 min; Mass spectrum (APCI): m/z=250 [M+H]$^+$.

Intermediate 76

1-(5-Chloropyrimidin-2-yl)piperidin-4-one

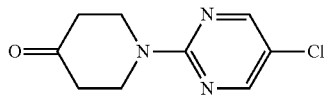 [SMILES: O=C1CCN(c2ncc(Cl)cn2)CC1]

8-(5-Chloropyrimidin-2-yl)-1,4-dioxa-8-azaspiro[4.5]decane (4.2 g) is dissolved in 6 M HCl (50 mL) and stirred at r.t. for 60 h. The solution is cooled in an ice bath and 4 M NaOH (90 mL) is added in portions to make the solution strongly basic (pH ~14). The mixture is extracted with dichloroemethane (2×200 mL) and the combined dichloromethane layers are dried over Na$_2$SO$_4$, filtered and concentrated to yield the title compound. LC (method 21): t$_R$=4.21 min; Mass spectrum (APCI): m/z=212 [M+H]$^+$.

Intermediate 77

1-(3-Fluoro-5-(trifluoromethyl)pyridin-2-yl)piperidin-4-one

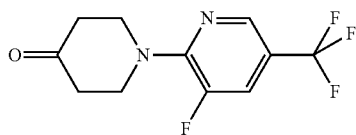 [SMILES: O=C1CCN(c2ncc(C(F)(F)F)cc2F)CC1]

The title compound is prepared from 8-[3-fluoro-5-(trifluoromethyl)pyridin-2-yl]-1,4-dioxa-8-azaspiro[4.5]decane following a procedure analogous to that described for Intermediate 76. LC (method 20): t$_R$=2.27 min; Mass spectrum (APCI): m/z=263 [M+H]$^+$.

Intermediate 78

1-(5-Ethylpyrimidin-2-yl)piperidin-4-one

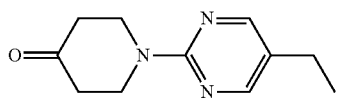

The title compound is prepared from (8-(5-ethylpyrimidin-2-yl)-1,4-dioxa-8-azaspiro[4.5]decane following a procedure analogous to that described for Intermediate 76. LC (method 21): t$_R$=2.74 min; Mass spectrum (APCI): m/z=206 [M+H]$^+$.

Intermediate 79

1-(5-Chloropyrimidin-2-yl)-N-cyclopropylpiperidin-4-amine

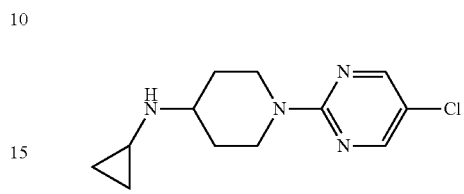

1-(5-Chloropyrimidin-2-yl)piperidin-4-one (1.5 g) is dissolved in anhydrous dichloromethane (25 mL) and cyclopropylamine (0.42 g) is added followed by glacial acetic acid (0.80 mL). Sodium triacetoxyborohydride (1.8 g) is then added in one portion under nitrogen and the resulting mixture stirred at r.t. for 17 h. The mixture is diluted with dichloroemthane (25 mL) and extracted with 3 M HCl (75 mL and 50 mL). The combined HCl layers are cooled on ice and 4 M NaOH (100 mL) is added in portions until the mixture is strongly basic (pH ~14). The mixture is then extracted with dichloroemthane (150 mL and 100 mL) and the combined dichloromethane layers are dried over Na$_2$SO$_4$, filtered and concentrated to yield the title compound. LC (method 21): t$_R$=2.57 min; Mass spectrum (APCI): m/z=253 [M+H]$^+$.

Intermediate 80

N-Cyclopropyl-1-[3-fluoro-5-(trifluoromethyl)pyridin-2-yl]piperidin-4-amine

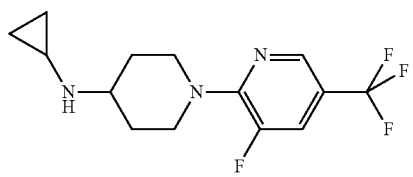 [SMILES: Fc1cc(C(F)(F)F)cnc1N1CCC(NC2CC2)CC1]

The title compound is prepared from 1-(3-fluoro-5-(trifluoromethyl)pyridin-2-yl)piperidin-4-onefollowing a procedure analogous to that described for Intermediate 79. LC (method 21): t$_R$=3.76 min; Mass spectrum (APCI): m/z=304 [M+H]$^+$.

Intermediate 81

N-Cyclopropyl-1-(5-ethylpyrimidin-2-yl)piperidin-4-amine

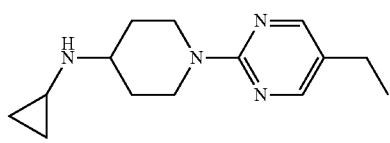 [SMILES: CCc1cnc(N2CCC(NC3CC3)CC2)nc1]

The title compound is prepared from 1-(5-ethylpyrimidin-2-yl)piperidin-4-one following a procedure analogous to that described for Intermediate 79. LC (method 21): $t_R$=2.08 min; Mass spectrum (APCI): m/z=247 [M+H]$^+$.

Intermediate 82

N-Cyclopropyl-1-[3-(propan-2-yl)-1,2,4-oxadiazol-5-yl]piperidin-4-amine

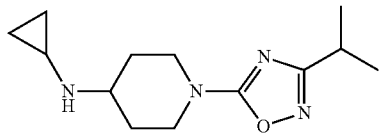 [SMILES: CC(C)c1noc(N2CCC(NC3CC3)CC2)n1]

The title compound is prepared from 1-[3-(propan-2-yl)-1,2,4-oxadiazol-5-yl]piperidin-4-one following a procedure analogous to that described for Intermediate 79. LC (method 21): $t_R$=2.09 min; Mass spectrum (APCI): m/z=251 [M+H]$^+$.

Intermediates 83 and 84

Benzyl (3R,4S)-4-(cyclopropylamino)-3-fluoropiperidine-1-carboxylate arbitrarily assigned as Isomer 1 (first eluting) and Benzyl (3S,4R)-4-(cyclopropylamino)-3-fluoropiperidine-1-carboxylate arbitrarily assigned as Isomer 2 (second eluting)

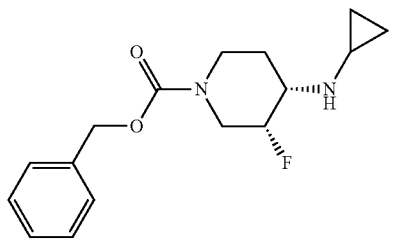

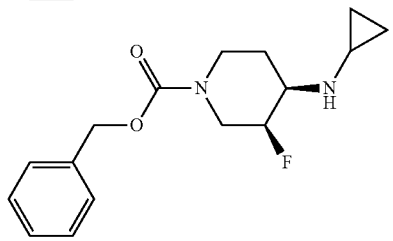

To a solution of benzyl-3-fluoro-4-oxopiperidine-1-carboxylate (10.0 g) and cyclopropylamine (2.5 g) in dichloromethane (100 mL) are added sodium triacetoxyborohydride (10.1 g) and glacial acetic acid (5.0 g). The reaction mixture is stirred at room temperature for 20 h. Then 60 mL of 2 N NaOH is added to reach pH 10. The mixture is extracted with dichloromethane (2×50 mL). The combined organic phases are dried over sodium sulfate, filtered and concentrated in vacuo and purified by silica gel chromatography (dichloromethane/MeOH 90:10) to afford the desired product as a mixture of mainly cis isomers [LC (method 20): $t_R$=1.98 min; mass spectrum (APCI): m/z=293 [M+H]$^+$.]. Chiral SFC separation (chiral SFC method 22) gives the separated title compounds (cis isomers of unknown absolute stereochemistry) arbitrarily assigned as Isomer 1 (first eluting; 7.25 min) and Isomer 2 (second eluting; 9.41 min).

In the following, all compounds derived from Intermediates 83 and 84 are assigned the same arbitrarily assigned configurations as the ones chosen here for each of them.

Intermediate 85 tert-Butyl N-cyclopropyl-N-[(3R,4S)-3-fluoropiperidin-4-yl]carbamate

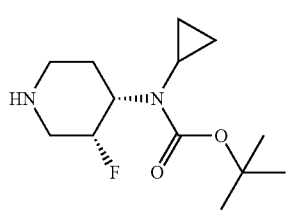 [SMILES: CC(C)(C)OC(=O)N(C1CC1)[C@H]1CCNC[C@H]1F]

Benzyl (3R,4S)-4-(cyclopropylamino)-3-fluoropiperidine-1-carboxylate (arbitrarily assigned as Isomer 1) (3.0 g) is dissolved in 1:1 tetrahydrofuran/water (100 mL) and NaOH (800 mg, 20 mmol) is added followed by Boc$_2$O (2.6 g) and stirred rapidly at r.t overnight. The reaction is heated to reflux and additional portions of Boc$_2$O are added over 2 d (3×2.6 g). The reaction is extracted with ethyl acetate and the organic extracts are washed with brine, dried over MgSO$_4$ and concentrated. Chromatography on silica gel eluting with ethyl acetate/hexane gives the Boc-protected intermediate and elution with MeOH/dichloromethane gives recovered amine. The intermediate is re-dissolved in ethyl acetate (30 mL) and 10% Pd/C (200 mg) is added and the reaction mixture stirred under an atmosphere of H$_2$ for 2 h at r.t. Filtration through celite and concentration gives the title compound. LC (method 20): $t_R$=1.95 min; Mass spectrum (APCI): m/z=259 [M+H]$^+$.

Intermediate 86 tert-Butyl N-cyclopropyl-N-[(3S,4R)-3-fluoropiperidin-4-yl]carbamate

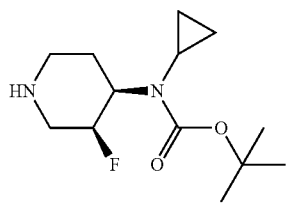 [SMILES: CC(C)(C)OC(=O)N(C1CC1)[C@@H]1CCNC[C@@H]1F]

The title compound is prepared from benzyl (3S,4R)-4-(cyclopropylamino)-3-fluoropiperidine-1-carboxylate (arbitrarily assigned as Isomer 2) following a procedure analogous to that described for Intermediate 85. LC (method 20): $t_R$=2.02 min; Mass spectrum (APCI): m/z=259 [M+H]⁺.

Intermediate 87

(3R,4S)-N-Cyclopropyl-3-fluoro-1-[5-(trifluoromethyl)pyridin-2-yl]piperidin-4-amine

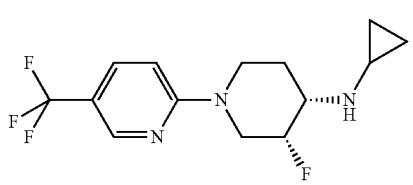 [SMILES: F[C@@H]1CN(c2ccc(C(F)(F)F)cn2)CC[C@@H]1NC1CC1]

A solution of tert-butyl N-cyclopropyl-N-[(3R,4S)-3-fluoropiperidin-4-yl]carbamate (100 mg), 2-chloro-5-trifluoromethylpyridine (141 mg) and Et₃N (78 mg) in N,N-dimethylformamide (2 mL) is heated in a microwave reactor at 130° C. for 3 h. After concentration the residue is purified by chromatography on silica gel eluting with 0% to 30% ethyl acetate/hexane to give the intermediate product [LC (method 20): $t_R$=3.19 min; mass spectrum (APCI): m/z=404 [M+H]⁺]. The Boc-amine is dissolved in dichloromethane (3 mL) and trifluoroacetic acid (0.5 mL) is added and the solution is stirred at r.t. for 1 h. After concentration dichloromethane (3 mL) and 2 M NaOH (2 mL) are added and the organic layer is separated, dried over MgSO₄ and concentrated to give the title compound. LC (method 20): $t_R$=1.99 min; Mass spectrum (APCI): m/z=304 [M+H]⁺.

Intermediate 88

(3S,4R)-N-Cyclopropyl-3-fluoro-1-[5-(trifluoromethyl)pyridin-2-yl]piperidin-4-amine

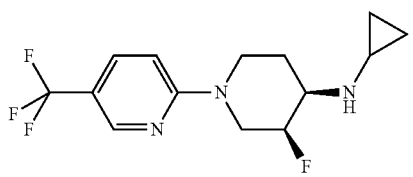 [SMILES: F[C@H]1CN(c2ccc(C(F)(F)F)cn2)CC[C@H]1NC1CC1]

The title compound is prepared from tert-butyl N-cyclopropyl-N-[(3S,4R)-3-fluoropiperidin-4-yl]carbamate following a procedure analogous to that described for Intermediate 87. LC (method 20): $t_R$=1.99 min; Mass spectrum (APCI): m/z=304 [M+H]⁺.

Intermediate 89

3R,4S)-N-Cyclopropyl-1-(5-ethylpyrimidin-2-yl)-3-fluoropiperidin-4-amine

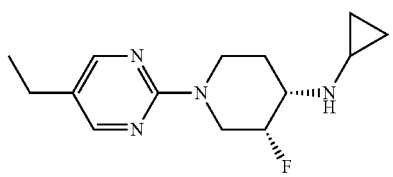 [SMILES: CCc1cnc(N2CC[C@H](NC3CC3)[C@H](F)C2)nc1]

The title compound is prepared from tert-butyl N-cyclopropyl-N-[(3R,4S)-3-fluoropiperidin-4-yl]carbamate and 2-chloro-5-ethylpyrimidine following a procedure analogous to that described for Intermediate 87. LC (method 20): $t_R$=1.80 min; Mass spectrum (APCI): m/z=265 [M+H]⁺.

Intermediate 90

(3S,4R)-N-Cyclopropyl-1-(5-ethylpyrimidin-2-yl)-3-fluoropiperidin-4-amine

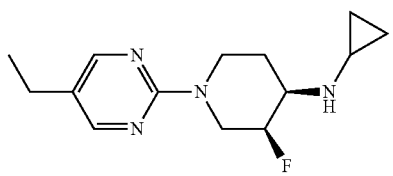 [SMILES: CCc1cnc(N2CC[C@@H](NC3CC3)[C@@H](F)C2)nc1]

The title compound is prepared from tert-butyl N-cyclopropyl-N-[(3S,4R)-3-fluoropiperidin-4-yl]carbamate and 2-chloro-5-ethylpyrimidine following a procedure analogous to that described for Intermediate 87. LC (method 20): $t_R$=1.80 min; Mass spectrum (APCI): m/z=265 [M+H]⁺.

Intermediate 91

(3S,4R)-1-(5-Chloropyrimidin-2-yl)-N-cyclopropyl-3-fluoropiperidin-4-amine

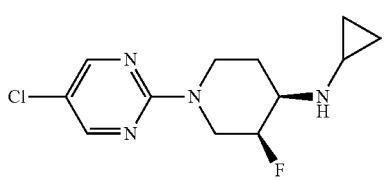 [SMILES: F[C@H]1CN(c2ncc(Cl)cn2)CC[C@H]1NC1CC1]

The title compound is prepared from tert-butyl N-cyclopropyl-N-[(3S,4R)-3-fluoropiperidin-4-yl]carbamate and 2,5-dichloropyrimidine following a procedure analogous to that described for Intermediate 87. LC (method 20): $t_R$=1.86 min; Mass spectrum (APCI): m/z=271 [M+H]$^+$.

Intermediate 92

(3S,4R)-N-Cyclopropyl-3-fluoro-1-[5-(trifluoromethyl)pyrimidin-2-yl]piperidin-4-amine

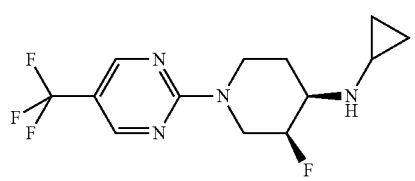 [SMILES: F[C@H]1CN(c2ncc(C(F)(F)F)cn2)CC[C@H]1NC1CC1]

The title compound is prepared from tert-butyl N-cyclopropyl-N-[(3S,4R)-3-fluoropiperidin-4-yl]carbamate and 2-chloro-5-trifluoromethyl-pyrimidine following a procedure analogous to that described for Intermediate 87.

Example 1

2-Imidazol-1-yl-pyrimidine-5-carboxylic acid cyclopropyl-[1-(3-phenyl-[1,2,4]oxadiazol-5-yl)-piperidin-4-yl]-amide

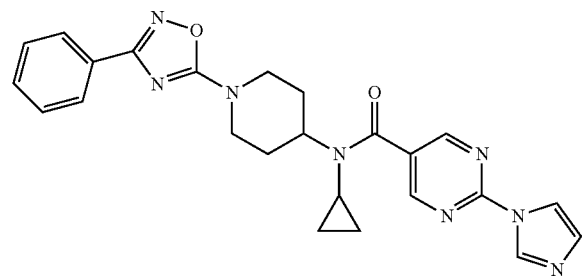 [SMILES: O=C(c1cnc(-n2ccnc2)nc1)N(C1CC1)C1CCN(c2nc(-c3ccccc3)no2)CC1]

2-(1H-Benzotriazol-1-yl)-1,1,3,3-tetramethyluronium tetrafluoroborate (75 mg) and ethyldiisopropylamine (74 μL) are added to a solution of 2-imidazol-1-yl-pyrimidine-5-carboxylic acid (40 mg) in N,N-dimethylformamide (5 mL) at room temperature. The solution is stirred for 10 min prior to the addition of cyclopropyl-[1-(3-phenyl-[1,2,4]oxadiazol-5-yl)-piperidin-4-yl]amine (60 mg). The resulting mixture is stirred at 60° C. for 3 h, cooled to room temperature over night, and concentrated in vacuo. The crude product is purified by HPLC(H$_2$O/MeOH/TFA). LC (method 1): $t_R$=1.50 min; Mass spectrum (ESI$^+$): m/z=457 [M+H]$^+$.

Example 2

2-Pyridin-4-yl-pyrimidine-5-carboxylic acid cyclopropyl-[1-(3-phenyl-[1,2,4]oxadiazol-5-yl)-piperidin-4-yl]-amide

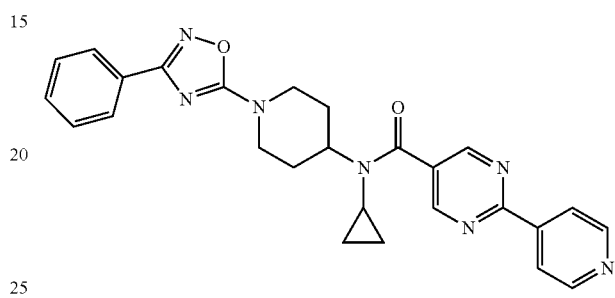

The title compound is prepared from cyclopropyl-[1-(3-phenyl-[1,2,4]oxadiazol-5-yl)-piperidin-4-yl]-amine and 2-pyridin-4-yl-pyrimidine-5-carboxylic acid following a procedure analogous to that described in Example 1. LC (method 2): $t_R$=1.76 min; Mass spectrum (ESI$^+$): m/z=468 [M+H]$^+$.

Example 3

2-(6-Ethoxy-pyridin-3-yl)-pyrimidine-5-carboxylic acid cyclopropyl-[1-(5-ethyl-pyrimidin-2-yl)-piperidin-4-yl]-amide

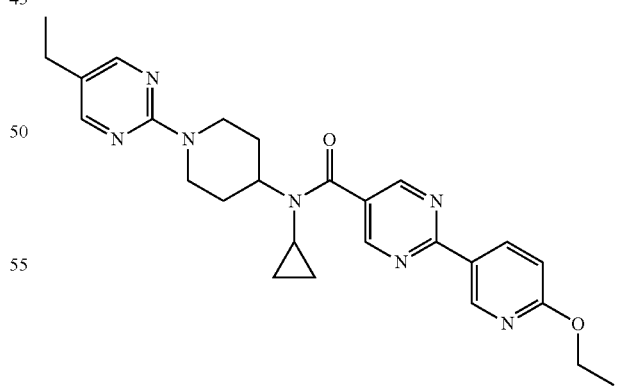

A mixture of 2-(6-ethoxy-pyridin-3-yl)-pyrimidine-5-carboxylic acid cyclopropyl-piperidin-4-yl-amide trifluoroacetic acid salt (48 mg), ethyldiisopropylamine (52 μL), and 2-chloro-5-ethylpyrimidine (14 mg) in N,N-dimethylformamide (2.0 mL) is stirred at 120° C. for 4 h. After cooling to room temperature, the reaction mixture is purified by HPLC (H₂O/MeOH/TFA) to give the title compound. LC (method 3): $t_R$=2.10 min; Mass spectrum (ESI⁺): m/z=474 [M+H]⁺.

Example 4

2-(6-Ethoxy-Pyridin-3-yl)-pyrimidine-5-carboxylic acid cyclopropyl-[1-(5-ethyl-pyrimidin-2-yl)-piperidin-4-yl]-amide

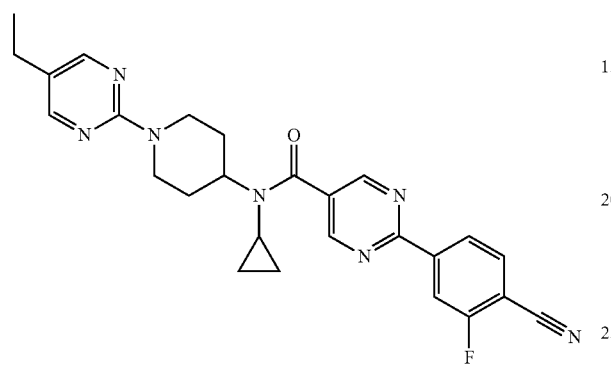

The title compound is prepared from 2-(4-cyano-3-fluoro-phenyl)-pyrimidine-5-carboxylic acid cyclopropyl-piperidin-4-yl-amide and 2-chloro-5-ethylpyrimidine following a procedure analogous to that described in Example 3. LC (method 3): $t_R$=2.01 min; Mass spectrum (ESI⁺): m/z=472 [M+H]⁺.

Example 5

2-(4-Cyanomethyl-phenyl)-pyrimidine-5-carboxylic acid cyclopropyl-[1-(5-ethyl-pyrimidin-2-yl)-piperidin-4-yl]-amide

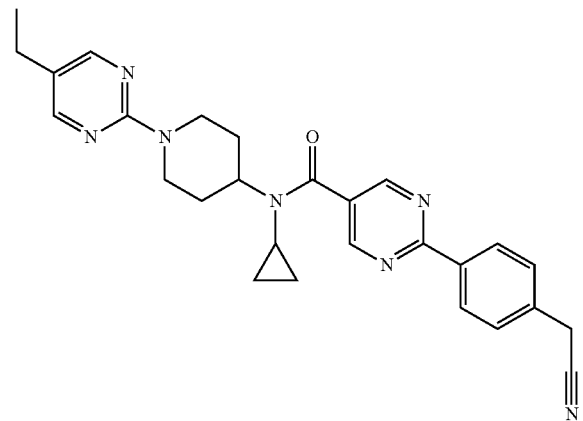 [SMILES: CCc1cnc(N2CCC(N(C(=O)c3cnc(-c4ccc(CC#N)cc4)nc3)C3CC3)CC2)nc1]

The title compound is prepared from 2-(4-cyanomethyl-phenyl)-pyrimidine-5-carboxylic acid cyclopropyl-piperidin-4-yl amide and 2-chloro-5-ethylpyrimidine following a procedure analogous to that described in Example 3. LC (method 3): $t_R$=1.84 min; Mass spectrum (ESI⁺): m/z=468 [M+H]⁺.

Example 6

N-Cyclopropyl-N-[1-(3-isopropyl-[1,2,4]oxadiazol-5-yl)-piperidin-4-yl]-6-(4-methanesulfonyl-phenyl)-nicotinamide

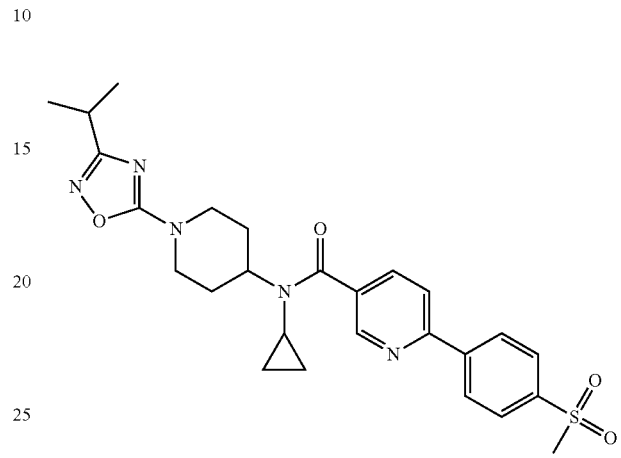

0.5 M solution of zinc chloride in tetrahydrofuran (4.52 mL) is added dropwise at room temperature to a mixture of N-hydroxy-isobutyramidine (58 mg) and N-(1-cyano-piperidin-4-yl)-N-cyclopropyl-6-(4-methanesulfonyl-phenyl)-nicotinamide (160 mg) in ethyl acetate (8 mL). The reaction mixture is stirred at 50° C. for two days and cooled to room temperature. The precipitate is filtered off and heated to 100° C. for 1 h in a mixture of ethanol (6 mL) and glacial acetic acid (3 mL). The solvents are evaporated in vacuo and dichloromethane and 10% aqueous K₂CO₃ solution are added to the residue. The organic phase is separated, washed with brine, dried over MgSO₄ and concentrated in vacuo. The residue is triturated with diethyl ether to give the title compound. LC (method 8): $t_R$=1.51 min; Mass spectrum (ESI⁺): m/z=510 [M+H]⁺.

Example 7

2-(6-Ethoxy-pyridin-3-yl)-pyrimidine-5-carboxylic acid cyclopropyl-[1-(3-phenyl[1,2,4]oxadiazol-5-yl)-piperidin-4-yl]amide

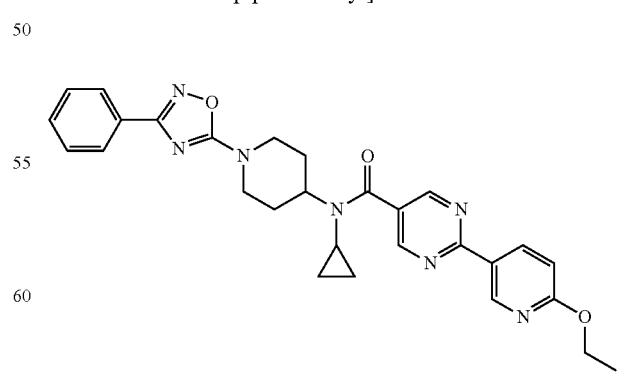

The title compound is prepared from 2-(6-ethoxy-pyridin-3-yl)-pyrimidine-5-carboxylic acid (1-cyano-piperidin-4-yl)-cyclopropyl-amide and N-hydroxy-benzamidine follow-

Example 8

2-(4-Cyanomethyl-phenyl)-pyrimidine-5-carboxylic acid cyclopropyl-[1-(3-ethyl-[1,2,4]oxadiazol-5-yl)-piperidin-4-yl]-amide

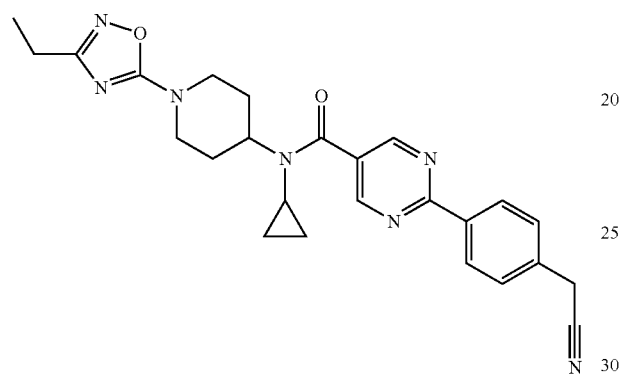

The title compound is prepared from 2-(4-cyanomethyl-phenyl)-pyrimidine-5-carboxylic acid (1-cyano-piperidin-4-yl)-cyclopropyl-amide and N-hydroxy-propionamidine following a procedure analogous to that described in Example 6. LC (method 3): $t_R$=1.86 min; Mass spectrum (ESI$^+$): m/z=458 [M+H]$^+$.

Example 9

2-(4-Cyanomethyl-phenyl)-pyrimidine-5-carboxylic acid cyclopropyl-[1-(3-phenyl-[1,2,4]oxadiazol-5-yl)-piperidin-4-yl]-amide

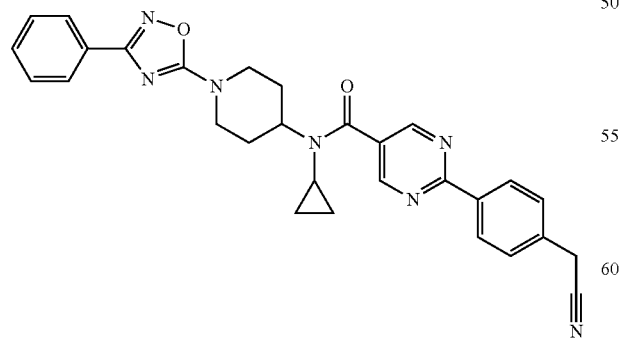

The title compound is prepared from 2-(4-cyanomethyl-phenyl)-pyrimidine-5-carboxylic acid (1-cyano-piperidin-4-yl)-cyclopropyl-amide and N-hydroxy-benzamidine following a procedure analogous to that described in Example 6. LC (method 3): $t_R$=2.20 min; Mass spectrum (ESI$^+$): m/z=512 [M+H]$^+$.

Example 10

2-(6-Ethoxy-pyridin-3-yl)-pyrimidine-5-carboxylic acid cyclopropyl-[1-(3-ethyl-[1,2,4]oxadiazol-5-yl)-piperidin-4-yl]-amide

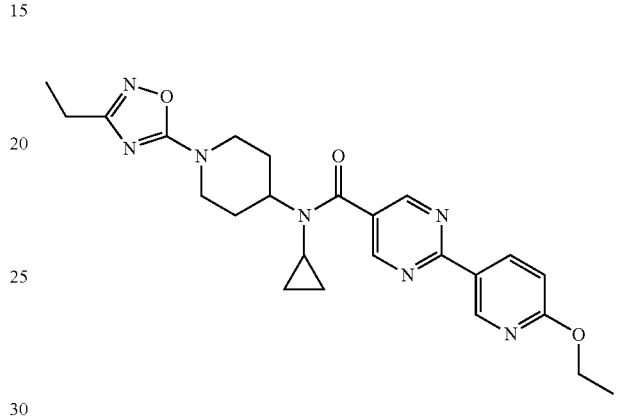

The title compound is prepared from 2-(6-ethoxy-pyridin-3-yl)-pyrimidine-5-carboxylic acid (1-cyano-piperidin-4-yl)-cyclopropyl-amide and N-hydroxy-propionamidine following a procedure analogous to that described in Example 6. LC (method 3): $t_R$=1.96 min; Mass spectrum (ESI$^+$): m/z=464 [M+H]$^+$.

Example 11

2-(4-Cyano-3-fluoro-phenyl)-pyrimidine-5-carboxylic acid cyclopropyl-[1-(3-ethyl-[1,2,4]oxadiazol-5-yl)-piperidin-4-yl]-amide

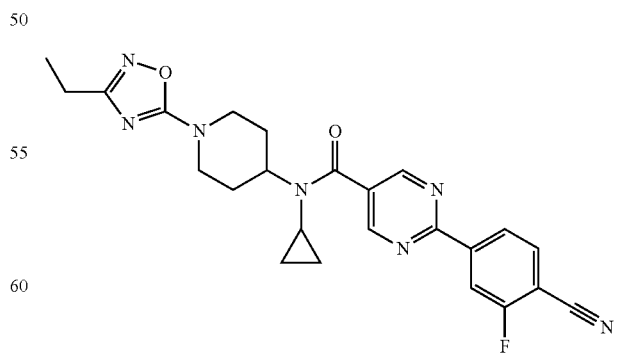

The title compound is prepared from 2-(4-cyano-3-fluoro-phenyl)-pyrimidine-5-carboxylic acid (1-cyano-piperidin-4-yl)-cyclopropyl-amide and N-hydroxy-propionamidine following a procedure analogous to that described in Example 6. LC (method 3): $t_R$=1.94 min; Mass spectrum (ESI$^+$): m/z=462 [M+H]$^+$.

Example 12

2-Imidazol-1-yl-pyrimidine-5-carboxylic acid cyclopropyl-[1-(5-ethyl-pyrimidin-2-yl)-piperidin-4-yl]-amide

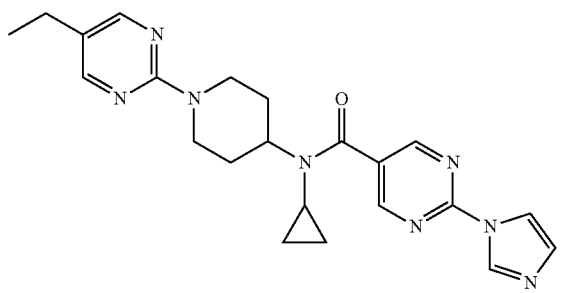 [SMILES: CCc1cnc(N2CCC(N(C(=O)c3cnc(-n4ccnc4)nc3)C3CC3)CC2)nc1]

The title compound is prepared from 2-imidazol-1-yl-pyrimidine-5-carboxylic acid cyclopropyl-piperidin-4-yl-amide and 2-chloro-5-ethylpyrimidine following a procedure analogous to that described in Example 3. LC (method 10): $t_R$=1.40 min; Mass spectrum (ESI$^+$): m/z=419 [M+H]$^+$.

Example 13

2-(4-Methanesulfonyl-phenyl)-pyrimidine-5-carboxylic acid cyclopropyl-[1-(5-ethyl-pyrimidin-2-yl)-piperidin-4-yl]-amide

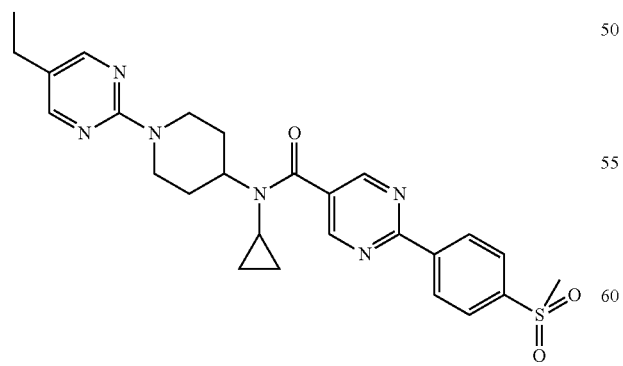

The title compound is prepared from 2-(4-methanesulfonyl-phenyl)-pyrimidine-5-carboxylic acid cyclopropyl-piperidin-4-yl-amide and 2-chloro-5-ethylpyrimidine following a procedure analogous to that described in Example 3. LC (method 10): $t_R$=1.80 min; Mass spectrum (ESI$^+$): m/z=507 [M+H]$^+$.

Example 14

2-(2-Methyl-imidazol-1-yl)-pyrimidine-5-carboxylic acid cyclopropyl-[1-(5-ethyl-pyrimidin-2-yl)-piperidin-4-yl]-amide The title compound is prepared from 2-(2-methyl-imidazol-1-yl)-pyrimidine-5-carboxylic acid cyclopropyl-piperidin-4-yl-amide and 2-chloro-5-ethylpyrimidine following a procedure analogous to that described in Example 3. LC (method 10): $t_R$=1.39 min; Mass spectrum (ESI$^+$): m/z=433 [M+H]$^+$.

Example 15

2-(2-Ethyl-imidazol-1-yl)-pyrimidine-5-carboxylic acid cyclopropyl-[1-(5-ethyl-pyrimidin-2-yl)-piperidin-4-yl]-amide

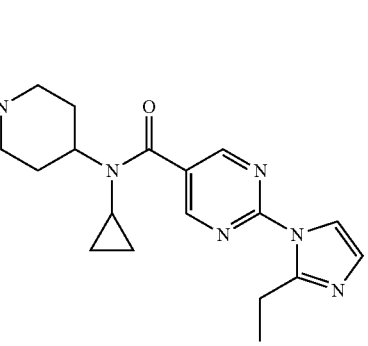

The title compound is prepared from 2-(2-ethyl-imidazol-1-yl)-pyrimidine-5-carboxylic acid cyclopropyl-piperidin-4-yl-amide and 2-chloro-5-ethylpyrimidine following a procedure analogous to that described in Example 3. LC (method 10): $t_R$=1.46 min; Mass spectrum (ESI⁺): m/z=447 [M+H]⁺.

Example 16

2-(4-Methanesulfonyl-phenyl)-pyrimidine-5-carboxylic acid cyclopropyl-[1-(3-propyl-[1,2,4]oxadiazol-5-yl)-piperidin-4-yl]-amide

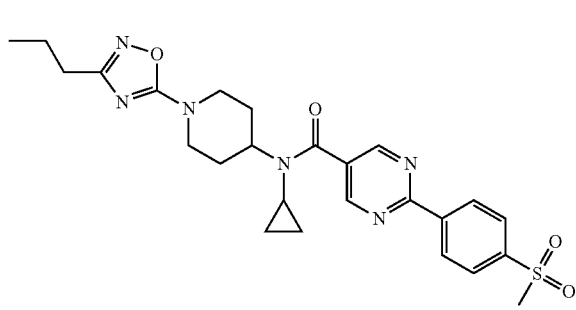 [SMILES: CCCc1noc(N2CCC(N(C(=O)c3cnc(-c4ccc(S(C)(=O)=O)cc4)nc3)C3CC3)CC2)n1]

The title compound is prepared from 2-(4-methanesulfonyl-phenyl)-pyrimidine-5-carboxylic acid (1-cyano-piperidin-4-yl)-cyclopropyl-amide and N-hydroxy-butyramidine following a procedure analogous to that described in Example 6. LC (method 10): $t_R$=1.87 min; Mass spectrum (ESI⁺): m/z=511 [M+H]⁺.

Example 17

6-Imidazol-1-yl-pyridazine-3-carboxylic acid cyclopropyl-[1-(5-ethyl-pyrimidin-2-yl)-piperidin-4-yl]-amide

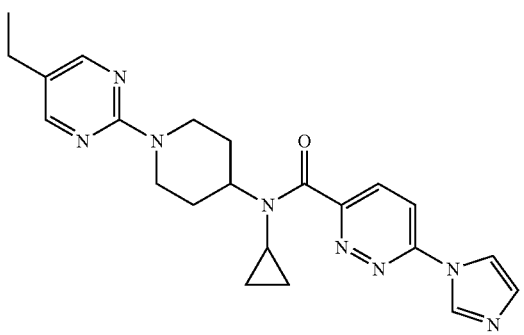 [SMILES: CCc1cnc(N2CCC(N(C(=O)c3ccc(-n4ccnc4)nn3)C3CC3)CC2)nc1]

The title compound is prepared from cyclopropyl-[1-(5-ethyl-pyrimidin-2-yl)-piperidin-4-yl]-amine and 6-imidazol-1-yl-pyridazine-3-carboxylic acid following a procedure analogous to that described in Example 1. LC (method 13): $t_R$=2.44 min; Mass spectrum (ESI⁺): m/z=419 [M+H]⁺.

Example 18

5-(4-Cyano-2-fluoro-phenyl)-[1,2,4]oxadiazole-3-carboxylic acid cyclopropyl-[1-(3-propyl-[1,2,4]oxadiazol-5-yl)-piperidin-4-yl]-amide

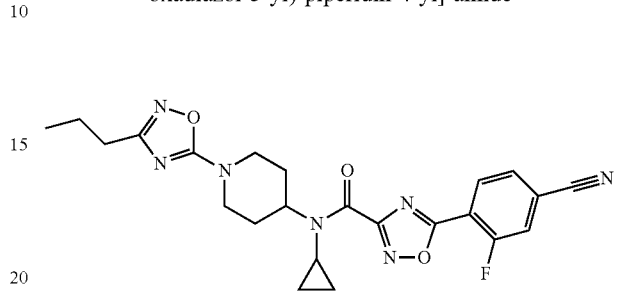

Oxalyl chloride (80 µL) is added dropwise to 5-(4-cyano-2-fluoro-phenyl)-[1,2,4]oxadiazole-3-carboxylic acid (50 mg) in dichloromethane (3 mL) chilled in an ice bath. One drop of N,N-dimethylformamide is added, the ice bath is removed, and the reaction mixture is stirred at room temperature for 1.5 h. The reaction mixture is concentrated in vacuo and dichloromethane (3 mL) is added to the residue. Cyclopropyl-[1-(3-propyl-[1,2,4]oxadiazol-5-yl)-piperidin-4-yl]-amine (59 mg) and triethylamine (60 µL) are added and the mixture is stirred for 1 h at room temperature. The reaction mixture is concentrated in vacuo and the crude product is purified by HPLC(H₂O/MeOH/TFA) to give the title compound. LC (method 14): $t_R$=1.40 min; Mass spectrum (ESI⁺): m/z=466 [M+H]⁺.

Example 19

2-(2-Methyl-imidazol-1-yl)-pyrimidine-5-carboxylic acid cyclopropyl-[1-(5-methyl-pyrazin-2-yl)-piperidin-4-yl]-amide

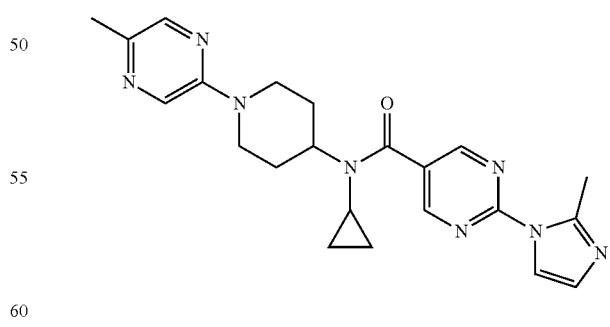

A mixture of 2-(2-methyl-imidazol-1-yl)-pyrimidine-5-carboxylic acid cyclopropyl-piperidin-4-yl-amide (44 mg, Intermediate 20), 2-chloro-5-methylpyrazine (15 mg) and ethyldiisopropylamine (35 µL) in N-methyl-2-pyrrolidinone (1.0 mL) is heated in a microwave oven for 30 min at 200° C. After removal of the solvent the residue is purified by HPLC (H₂O/MeOH/TFA) to give the title compound. LC (method 3): $t_R$=0.92 min; Mass spectrum (ESI⁺): m/z=419 [M+H]⁺.

Example 20

2-(4-Methanesulfonyl-phenyl)-pyrimidine-5-carboxylic acid cyclopropyl-[1-(5-cyclopropyl-[1,2,4]oxadiazol-3-yl)-piperidin-4-yl]-amide

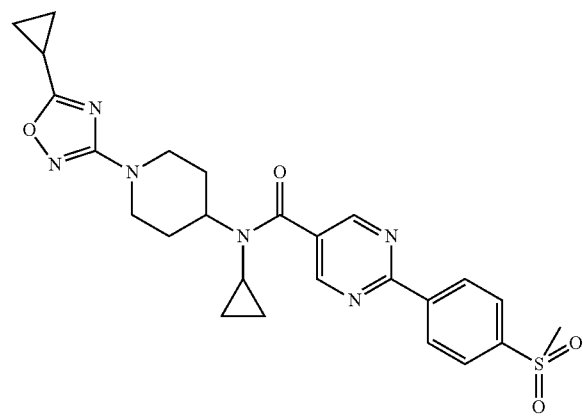 [SMILES: CS(=O)(=O)c1ccc(-c2ncc(C(=O)N(C3CC3)C3CCN(c4noc(C5CC5)n4)CC3)cn2)cc1]

Hydroxylamine hydrochloride (21 mg) is added to 2-(4-methanesulfonyl-phenyl)-pyrimidine-5-carboxylic acid (1-cyano-piperidin-4-yl)-cyclopropyl-amide (130 mg, Intermediate 22) and ethyldiisopropylamine (634) in ethanol (30 mL) and the mixture is refluxed for 4 h. Another 10 mg hydroxylamine hydrochloride is added and the mixture is refluxed for 1 h and stirred at room temperature for 12 h. The solvent is removed in vacuo and the residue is purified by preparative HPLC (MeOH/H₂O/TFA) to yield 2-(4-methanesulfonyl-phenyl)-pyrimidine-5-carboxylic acid cyclopropyl-[1-(N-hydroxycarbamimidoyl)-piperidin-4-yl]-amide as an intermediate. Subsequently 50 mg of the aforementioned intermediate are added to tetrahydrofuran (10 mL) followed by ethyldiisopropylamine (28 µL) and cyclopropanecarbonyl chloride (10 µL). The mixture is stirred at room temperature for 3 h. Acetonitrile is added and the mixture is refluxed for 12 h. After removal of the solvents the residue is purified by HPLC (MeOH/H₂O/ammonia) to yield the desired product. LC (method 16): $t_R$=1.17 min; Mass spectrum (ESI⁺): m/z=509 [M+H]⁺.

Example 21

2-Imidazol-1-yl-pyrimidine-5-carboxylic acid cyclopropyl-[1-(3-propyl-[1,2,4]oxadiazol-5-yl)-piperidin-4-yl]-amide

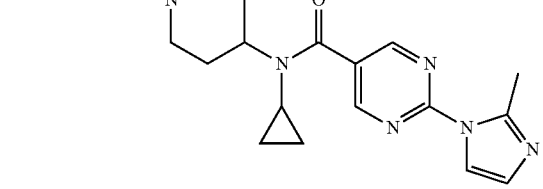

To 2-imidazol-1-yl-pyrimidine-5-carboxylic acid (1-cyano-piperidin-4-yl)-cyclopropyl-amide (50 mg, Intermediate 33) and N-hydroxy-butyramidine (30 mg) in ethyl acetate (12 mL) and tetrahydrofuran is added zinc chloride (0.64 mL, 0.7 M in tetrahydrofuran) and the mixture is stirred for two weeks. Again zinc chloride solution and N-hydroxy-butyramidine are added and stirring is continued at room temperature for 24 h. The solvents are removed in vacuo, ethanol (15 mL) and concentrated HCl solution (0.5 mL) are added and the mixture is stirred for 3 h under reflux. After removal of the solvent the residue is purified by HPLC (MeOH, H₂O, ammonia) to yield the desired product. LC (method 3): $t_R$=1.51 min; Mass spectrum (ESI⁺): m/z=423 [M+H]⁺.

Example 22

2-(2-Methyl-imidazol-1-yl)-pyrimidine-5-carboxylic acid cyclopropyl-[1-(3-propyl-[1,2,4]oxadiazol-5-yl)-piperidin-4-yl]-amide The title compound is prepared from 2-(2-methyl-imidazol-1-yl)-pyrimidine-5-carboxylic acid (1-cyano-piperidin-4-yl)-cyclopropyl-amide (Intermediate 31) following a procedure analogous to that described in Example 21. LC (method 3): $t_R$=1.55 min; Mass spectrum (ESI$^+$): m/z=437 [M+H]$^+$.

Example 23

2-(2-Ethyl-imidazol-1-yl)-pyrimidine-5-carboxylic acid cyclopropyl-[1-(3-propyl-[1,2,4]oxadiazol-5-yl)-piperidin-4-yl]-amide

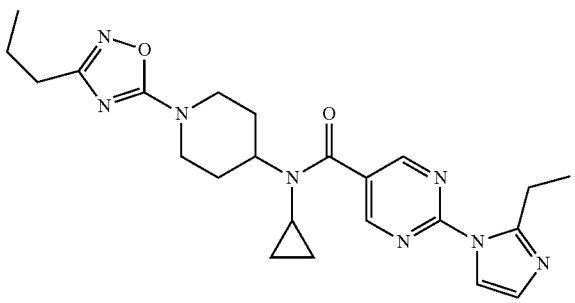 [SMILES: CCCc1noc(N2CCC(N(C(=O)c3cnc(-n4ccnc4CC)nc3)C3CC3)CC2)n1]

The title compound is prepared from 2-(2-ethyl-imidazol-1-yl)-pyrimidine-5-carboxylic acid (1-cyano-piperidin-4-yl)-cyclopropyl-amide (Intermediate 32) following a procedure analogous to that described in Example 21. LC (method 3): $t_R$=1.56 min; Mass spectrum (ESI$^+$): m/z=451 [M+H]$^+$.

Example 24

2-(2-Methyl-imidazol-1-yl)-pyrimidine-5-carboxylic acid cyclopropyl-[1-(5-cyclopropyl-[1,2,4]oxadiazol-3-yl)-piperidin-4-yl]-amide

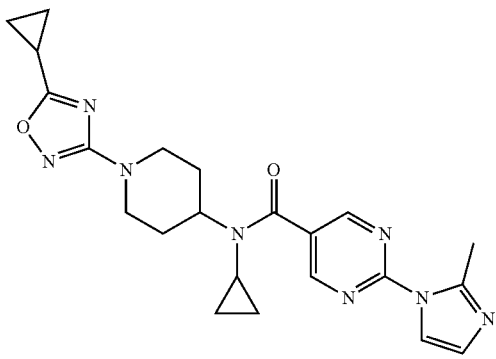 [SMILES: Cc1nccn1-c1ncc(C(=O)N(C2CC2)C2CCN(c3noc(C4CC4)n3)CC2)cn1]

The title compound is prepared from 2-(2-methyl-imidazol-1-yl)-pyrimidine-5-carboxylic acid (1-cyano-piperidin-4-yl)-cyclopropyl-amide (Intermediate 31) following a procedure analogous to that described in Example 20, except that the intermediate (N-hydroxycarbamimidoyl)-piperidine derivative is used without further purification and 1,4-dioxane is used as solvent for the subsequent second step. LC (method 16): $t_R$=0.88 min; Mass spectrum (ESI$^+$): m/z=435 [M+H]$^+$.

Example 25

2-Imidazol-1-yl-pyrimidine-5-carboxylic acid cyclopropyl-[1-(5-cyclopropyl-[1,2,4]oxadiazol-3-yl)-piperidin-4-yl]-amide

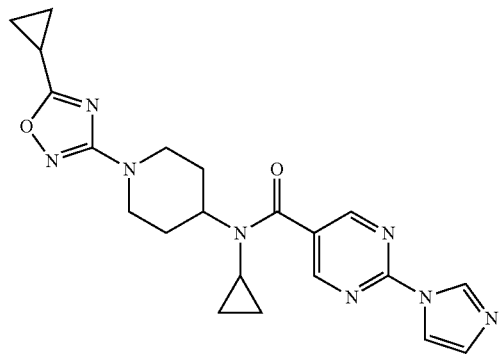 [SMILES: O=C(c1cnc(-n2ccnc2)nc1)N(C1CC1)C1CCN(c2noc(C3CC3)n2)CC1]

The title compound is prepared from 2-imidazol-1-yl-pyrimidine-5-carboxylic acid (1-cyano-piperidin-4-yl)-cyclopropyl-amide (Intermediate 33) following a procedure analogous to that described in Example 20, except that the intermediate (N-hydroxycarbamimidoyl)-piperidine derivative is used without further purification and 1,4-dioxane is used as solvent for the subsequent second step. LC (method 16): $t_R$=0.83 min; Mass spectrum (ESI$^+$): m/z=421 [M+H]$^+$.

Example 26

2-(2-Ethyl-imidazol-1-yl)-pyrimidine-5-carboxylic acid cyclopropyl-[1-(5-cyclopropyl-[1,2,4]oxadiazol-3-yl)-piperidin-4-yl]-amide

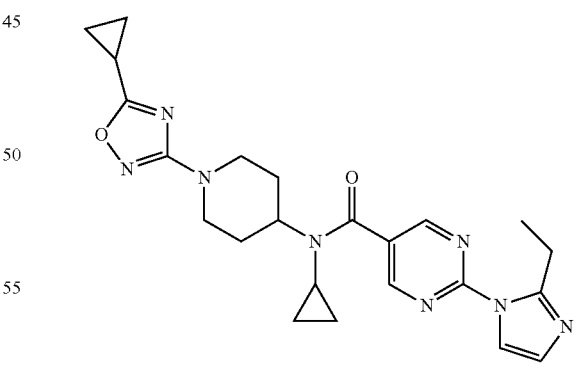

Hydroxylamine hydrochloride (36 mg) is added to 2-(2-ethyl-imidazol-1-yl)-pyrimidine-5-carboxylic acid (1-cyano-piperidin-4-yl)-cyclopropyl-amide (180 mg, Intermediate 32) and ethyldiisopropylamine (0.1 mL) in ethanol (30 mL) and the mixture is refluxed for 4 h. Another 10 mg hydroxylamine hydrochloride is added and the mixture is refluxed for 1 h and stirred at room temperature for 12 h. The solvent is removed in vacuo to yield the respective (N-hydroxycarbamimidoyl)-piperidine derivative as an intermediate. Subsequently 50 mg of the aforementioned intermediate are added to tetrahydrofuran (10 mL) followed by ethyldiisopropylamine (32 µL) and cyclopropanecarbonyl chloride (11 µL). The mixture is stirred at room temperature for 1.5 h. Acetonitrile is added and the mixture is refluxed for 5 h. The mixture is concentrated and 1,2-dicholorethane (2.0 mL) and (methoxycarbonylsulfamoyl) triethylammonium hydroxide (Burgess reagent, 75 mg) are added and the mixture is heated in a microwave oven to 130° C. for 15 min. The solvent is removed in vacuo and the residue is purified by HPLC (MeOH/H$_2$O/TFA) to yield the desired product. LC (method 9): t$_R$=1.09 min; Mass spectrum (ESI$^+$): m/z=449 [M+H]$^+$.

Example 27

2-(2-Methyl-imidazol-1-yl)-pyrimidine-5-carboxylic acid cyclopropyl-(3'-fluoro-5'-trifluoromethyl-3,4,5,6-tetrahydro-2H-[1,2']bipyridinyl-4-yl)-amide

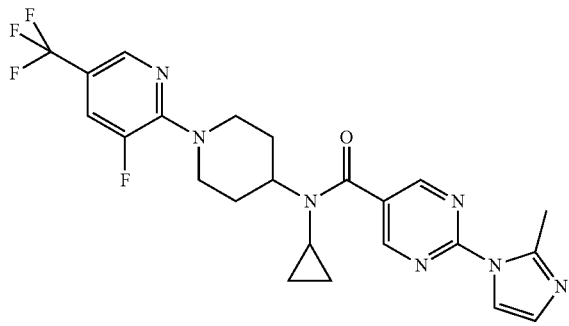 [SMILES: Cc1nccn1-c1ncc(C(=O)N(C2CC2)C2CCN(c3ncc(C(F)(F)F)cc3F)CC2)cn1]

A mixture of 2-(2-methyl-imidazol-1-yl)-pyrimidine-5-carboxylic acid cyclopropyl-piperidin-4-yl-amide (44 mg), 2,3-difluoro-5-(trifluoromethyl)pyridine (22 mg), and ethyldiisopropylamine (35 µL) in N-methyl-2-pyrrolidinone (1 mL) is heated to 200° C. for 0.5 h in a microwave oven. The reaction mixture is concentrated and the crude product is purified by preparative HPLC (MeOH/H$_2$O/ammonia). LC (method 16): t$_R$=1.29 min; Mass spectrum (ESI$^+$): m/z=490 [M+H]$^+$.

Example 28

3-(4-Cyano-2-fluoro-phenyl)-isoxazole-5-carboxylic acid cyclopropyl-[1-(3-isopropyl-[1,2,4]oxadiazol-5-yl)-piperidin-4-yl]-amide

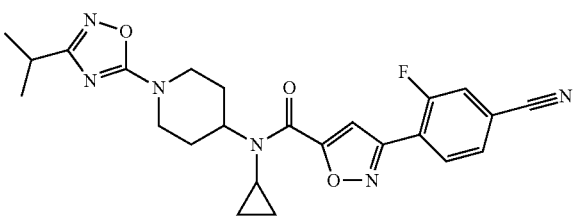 [SMILES: CC(C)c1noc(N2CCC(N(C(=O)c3cc(-c4ccc(C#N)cc4F)no3)C3CC3)CC2)n1]

The title compound is prepared from 3-(4-cyano-2-fluorophenyl)-isoxazole-5-carboxylic acid and cyclopropyl-[1-(3-isopropyl-[1,2,4]oxadiazol-5-yl)-piperidin-4-yl]-amine following a procedure analogous to that described in Example 18. LC (method 18): t$_R$=1.23 min; Mass spectrum (ESI$^+$): m/z=465 [M+H]$^+$.

Example 29

5-(4-Cyano-2-fluoro-phenyl)-isoxazole-3-carboxylic acid cyclopropyl-[1-(3-isopropyl-[1,2,4]oxadiazol-5-yl)-piperidin-4-yl]-amide

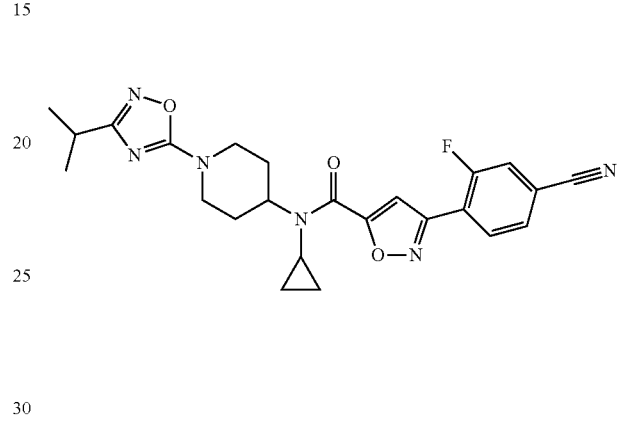

The title compound is prepared from 5-(4-cyano-2-fluorophenyl)-isoxazole-3-carboxylic acid and cyclopropyl-[1-(3-isopropyl-[1,2,4]oxadiazol-5-yl)-piperidin-4-yl]-amine following a procedure analogous to that described in Example 18. LC (method 18): t$_R$=1.23 min; Mass spectrum (ESI$^+$): m/z=465 [M+H]$^+$.

Example 30

5-(4-Cyano-2-fluoro-phenyl)-isoxazole-3-carboxylic acid [1-(3-tert-butyl-[1,2,4]oxadiazol-5-yl)-piperidin-4-yl]-cyclopropyl-amide

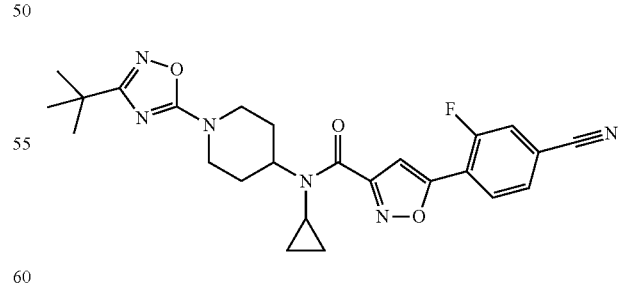

The title compound is prepared from 5-(4-cyano-2-fluorophenyl)-isoxazole-3-carboxylic acid and [1-(3-tert-butyl-[1,2,4]oxadiazol-5-yl)-piperidin-4-yl]-cyclopropyl-amine fol-

Example 31

3-(4-Cyano-2-fluoro-phenyl)-isoxazole-5-carboxylic acid [1-(3-tert-butyl-[1,2,4]oxadiazol-5-yl)-piperidin-4-yl]-cyclopropyl-amide

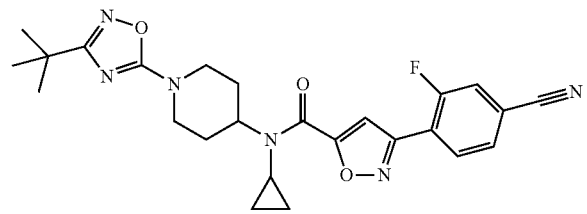 [SMILES: CC(C)(C)c1noc(N2CCC(N(C(=O)c3cc(-c4ccc(C#N)cc4F)no3)C3CC3)CC2)n1]

The title compound is prepared from 3-(4-cyano-2-fluoro-phenyl)-isoxazole-5-carboxylic acid and [1-(3-tert-butyl-[1,2,4]oxadiazol-5-yl)-piperidin-4-yl]-cyclopropyl-amine following a procedure analogous to that described in Example 18. LC (method 18): $t_R$=1.29 min; Mass spectrum (ESI⁺): m/z=479 [M+H]⁺.

Example 32

5-Oxazol-5-yl-pyrazine-2-carboxylic acid [1-(3-tert-butyl-[1,2,4]oxadiazol-5-yl)-piperidin-4-yl]-cyclopropyl-amide

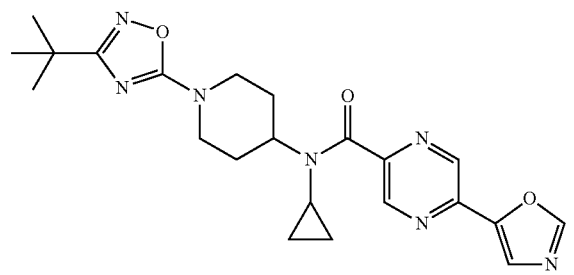 [SMILES: CC(C)(C)c1noc(N2CCC(N(C(=O)c3cnc(-c4cnco4)cn3)C3CC3)CC2)n1]

The title compound is prepared from [1-(3-tert-butyl-[1,2,4]oxadiazol-5-yl)-piperidin-4-yl]-cyclopropyl-amine and 5-oxazol-5-yl-pyrazine-2-carboxylic acid following a procedure analogous to that described in Example 1. LC (method 8): $t_R$=1.57 min; Mass spectrum (ESI⁺): m/z=438 [M+H]⁺.

Example 33

5-Oxazol-5-yl-pyrazine-2-carboxylic acid cyclopropyl-[1-(3-isopropyl-[1,2,4]oxadiazol-5-yl)-piperidin-4-yl]amide

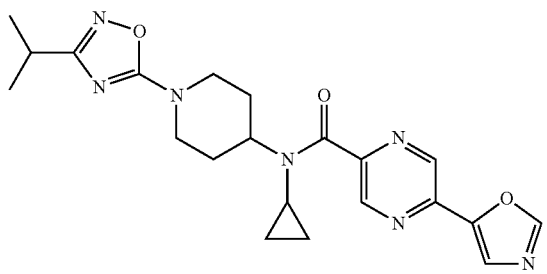 [SMILES: CC(C)c1noc(N2CCC(N(C(=O)c3cnc(-c4cnco4)cn3)C3CC3)CC2)n1]

The title compound is prepared from cyclopropyl-[1-(3-isopropyl-[1,2,4]oxadiazol-5-yl)-piperidin-4-yl]-amine and 5-oxazol-5-yl-pyrazine-2-carboxylic acid following a procedure analogous to that described in Example 1 using chloro-N,N,N',N'-tetramethylformamidinium hexafluorophosphate as reagent and tetrahydrofuran as solvent. LC (method 8): $t_R$=1.47 min; Mass spectrum (ESI⁺): m/z=424 [M+H]⁺.

Example 34

N-Cyclopropyl-N-[1-(5-ethyl-pyrimidin-2-yl)-piperidin-4-yl]-6-oxazol-5-yl-nicotinamide

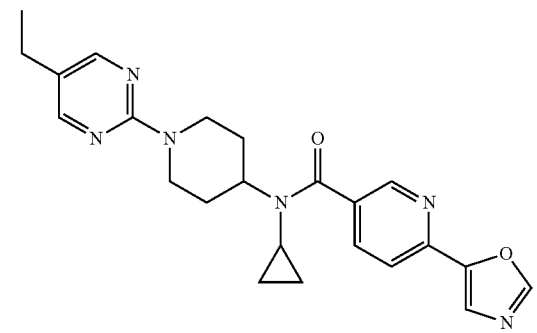 [SMILES: CCc1cnc(N2CCC(N(C(=O)c3ccc(-c4cnco4)nc3)C3CC3)CC2)nc1]

The title compound is prepared from cyclopropyl-[1-(5-ethyl-pyrimidin-2-yl)-piperidin-4-yl]-amine and 6-oxazol-5-yl-nicotinic acid following a procedure analogous to that

Example 35

N-Cyclopropyl-N-[1-(3-isopropyl-[1,2,4]oxadiazol-5-yl)-piperidin-4-yl]-6-oxazol-5-yl-nicotinamide

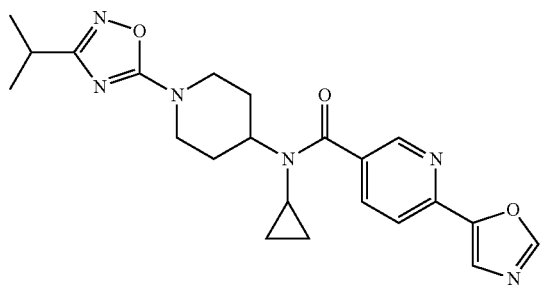 [SMILES: CC(C)c1noc(N2CCC(N(C(=O)c3ccc(-c4cnco4)nc3)C3CC3)CC2)n1]

The title compound is prepared from cyclopropyl-[1-(3-isopropyl-[1,2,4]oxadiazol-5-yl)-piperidin-4-yl]-amine and 6-oxazol-5-yl-nicotinic acid following a procedure analogous to that described in Example 1. LC (method 7): $t_R$=1.08 min; Mass spectrum (ESI$^+$): m/z=423 [M+H]$^+$.

Example 36

N-[1-(3-tert-Butyl-[1,2,4]oxadiazol-5-yl)-piperidin-4-yl]-N-cyclopropyl-6-oxazol-5-yl-nicotinamide

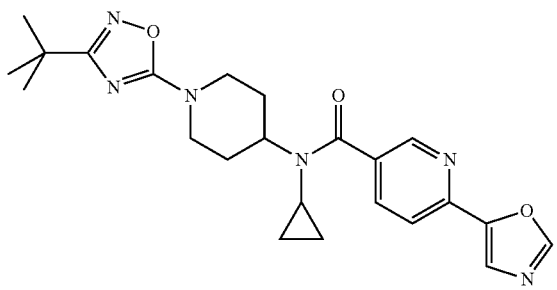 [SMILES: CC(C)(C)c1noc(N2CCC(N(C(=O)c3ccc(-c4cnco4)nc3)C3CC3)CC2)n1]

The title compound is prepared from [1-(3-tert-butyl-[1,2,4]oxadiazol-5-yl)-piperidin-4-yl]-cyclopropyl-amine and 6-oxazol-5-yl-nicotinic acid following a procedure analogous to that described in Example 1. LC (method 7): $t_R$=1.02 min; Mass spectrum (ESI$^+$): m/z=419 [M+H]$^+$.

Example 37

N-Cyclopropyl-N-[1-(5-ethyl-pyrazin-2-yl)-piperidin-4-yl]-6-oxazol-5-yl-nicotinamide

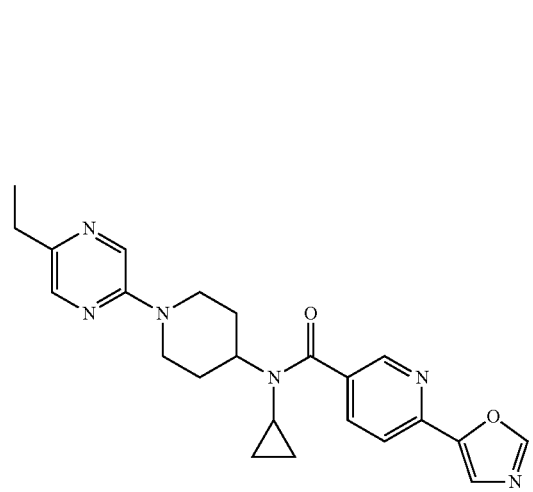 [SMILES: CCc1cnc(N2CCC(N(C(=O)c3ccc(-c4cnco4)nc3)C3CC3)CC2)cn1]

The title compound is prepared from cyclopropyl-[1-(5-ethyl-pyrazin-2-yl)-piperidin-4-yl]-amine and 6-oxazol-5-yl-nicotinic acid following a procedure analogous to that described in Example 1. LC (method 7): $t_R$=1.05 min; Mass spectrum (ESI$^+$): m/z=419 [M+H]$^+$.

Example 38

5-Oxazol-5-yl-pyrazine-2-carboxylic acid cyclopropyl-[1-(5-ethyl-pyrimidin-2-yl)-piperidin-4-yl]-amide

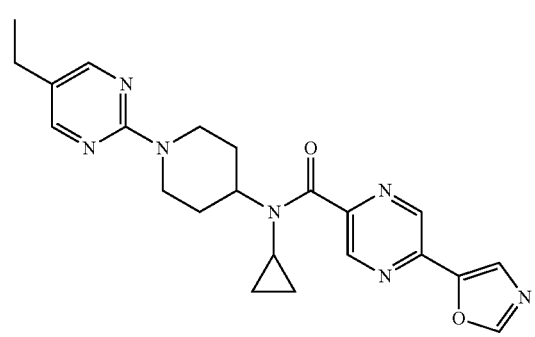 [SMILES: CCc1cnc(N2CCC(N(C(=O)c3cnc(-c4cnco4)cn3)C3CC3)CC2)nc1]

The title compound is prepared from cyclopropyl-[1-(5-ethyl-pyrimidin-2-yl)-piperidin-4-yl]-amine and 5-oxazol-5-yl-pyrazine-2-carboxylic following a procedure analogous to that described in Example 18 using thionyl chloride instead of oxalyl chloride. LC (method 7): $t_R$=1.03 min; Mass spectrum (ESI$^+$): m/z=420 [M+H]$^+$.

Example 39

5-Oxazol-5-yl-pyrazine-2-carboxylic acid cyclopropyl-[1-(3-propyl-[1,2,4]oxadiazol-5-yl)-piperidin-4-yl]-amide

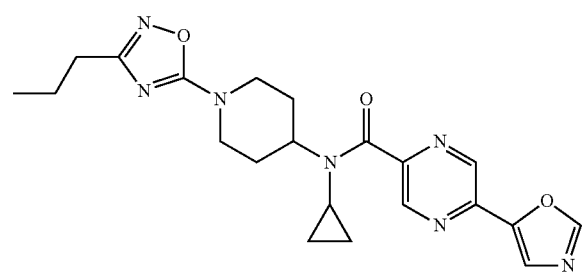 [SMILES: CCCc1noc(N2CCC(N(C(=O)c3cnc(-c4cnco4)cn3)C3CC3)CC2)n1]

The title compound is prepared from cyclopropyl-[1-(3-propyl-[1,2,4]oxadiazol-5-yl)-piperidin-4-yl]-amine and 5-oxazol-5-yl-pyrazine-2-carboxylic acid following a procedure analogous to that described in Example 1. LC (method 8): $t_R$=1.48 min; Mass spectrum (ESI$^+$): m/z=424 [M+H]$^+$.

Example 40

N-Cyclopropyl-6-oxazol-5-yl-N-[1-(3-propyl-[1,2,4]oxadiazol-5-yl)-piperidin-4-yl]-nicotinamide

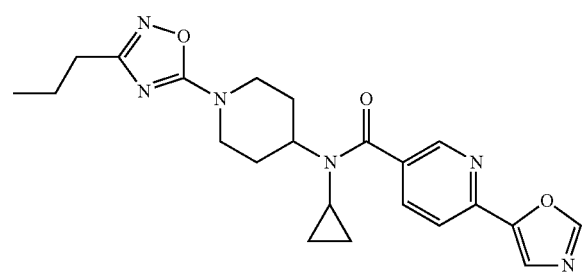 [SMILES: CCCc1noc(N2CCC(N(C(=O)c3ccc(-c4cnco4)nc3)C3CC3)CC2)n1]

The title compound is prepared from cyclopropyl-[1-(3-propyl-[1,2,4]oxadiazol-5-yl)-piperidin-4-yl]-amine and 6-oxazol-5-yl-nicotinic acid following a procedure analogous to that described in Example 1. LC (method 7): $t_R$=1.09 min; Mass spectrum (ESI$^+$): m/z=423 [M+H]$^+$.

Example 41

N-Cyclopropyl-N-[1-(5-methyl-pyrimidin-2-yl)-piperidin-4-yl]-6-oxazol-5-yl-nicotinamide

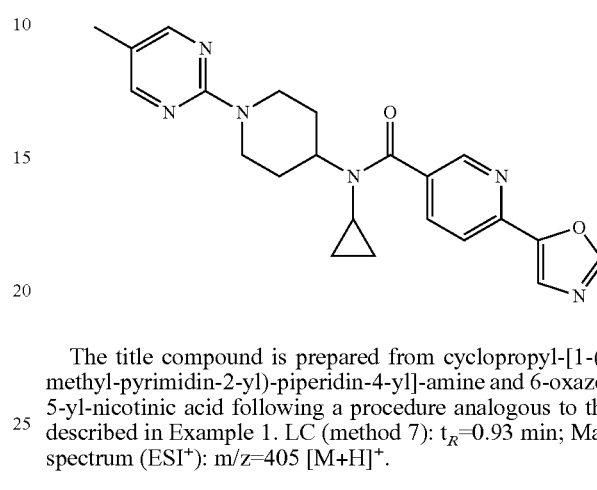

The title compound is prepared from cyclopropyl-[1-(5-methyl-pyrimidin-2-yl)-piperidin-4-yl]-amine and 6-oxazol-5-yl-nicotinic acid following a procedure analogous to that described in Example 1. LC (method 7): $t_R$=0.93 min; Mass spectrum (ESI$^+$): m/z=405 [M+H]$^+$.

Example 42

N-Cyclopropyl-N-[1-(5-methyl-pyrazin-2-yl)-piperidin-4-yl]-6-oxazol-5-yl-nicotinamide

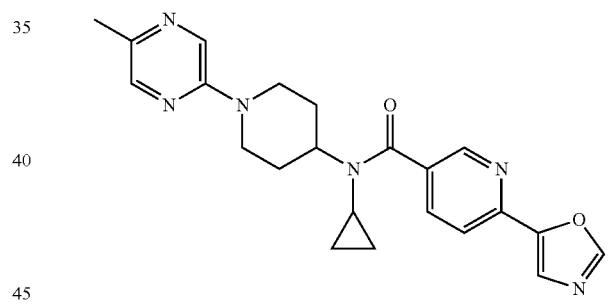

The title compound is prepared from cyclopropyl-[1-(5-methyl-pyrazin-2-yl)-piperidin-4-yl]-amine and 6-oxazol-5-yl-nicotinic acid following a procedure analogous to that described in Example 1. LC (method 7): $t_R$=0.96 min; Mass spectrum (ESI$^+$): m/z=405 [M+H]$^+$.

General Procedure for the Synthesis of Amides in Table 1 from their Respective Amines and Carboxylic Acids.

Amines (~5 mg) and acids (~6 mg) are combined with Et$_3$N (0.015 mL) and 1-hydroxybenzotriazole (3 mg) in N,N-dimethylformamide (0.4 mL) and 1-(3-dimethylaminopropyl)-3-ethylcarbodiimide (12 mg) is added in N,N-dimethylformamide (0.1 mL) and the mixture is stirred at room temperature for 18 h. The product amides are purified by preparative HPLC.

Examples 69-75 compiled in Table 1 are derived from Intermediate 83 and are assigned the same arbitrarily assigned configuration as the one chosen for Intermediate 83.

Examples 76-103 and 107-112 compiled in Table 1 are derived from Intermediate 84 and are assigned the same arbitrarily assigned configuration as the one chosen for Intermediate 84.

TABLE 1

| Example | Structure/Name | Mass spectrum (APCI): m/z | LC |
|---|---|---|---|
| 43 | 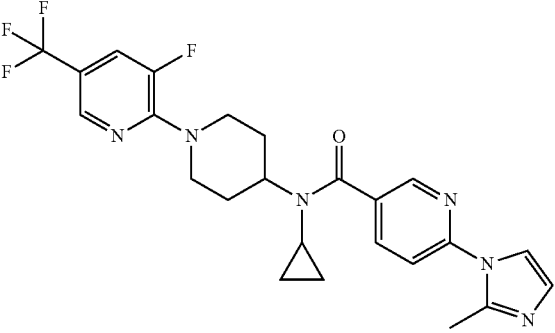<br>N-cyclopropyl-N-{1-[3-fluoro-5-(trifluoromethyl)pyridin-2-yl]piperidin-4-yl}-6-(2-methyl-1H-imidazol-1-yl)pyridine-3-carboxamide | 489.2 | method 23: $t_R$ = 4.18 min |
| 44 | 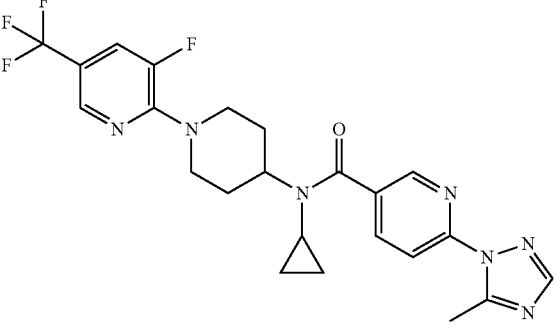<br>N-cyclopropyl-N-{1-[3-fluoro-5-(trifluoromethyl)pyridin-2-yl]piperidin-4-yl}-6-(5-methyl-1H-1,2,4-triazol-1-yl)pyridine-3-carboxamide | 490.2 | method 23: $t_R$ = 4.35 min |
| 45 | 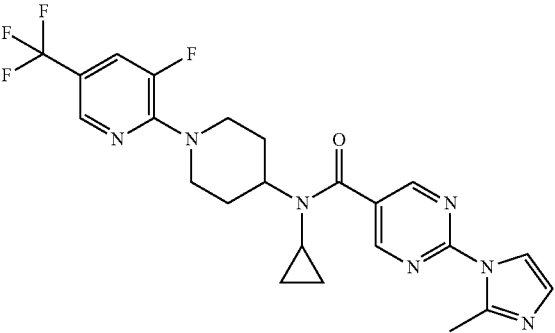<br>N-cyclopropyl-N-{1-[3-fluoro-5-(trifluoromethyl)pyridin-2-yl]piperidin-4-yl}-5-(2-methyl-1H-imidazol-1-yl)pyrazine-2-carboxamide | 490.2 | method 23: $t_R$ = 4.36 min |

TABLE 1-continued

| Example | Structure/Name | Mass spectrum (APCI): m/z | LC |
|---|---|---|---|
| 46 | 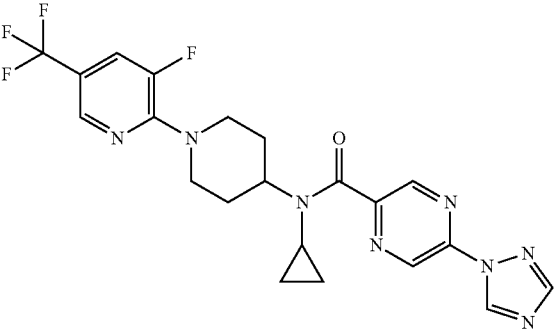<br>N-cyclopropyl-N-{1-[3-fluoro-5-(trifluoromethyl)pyridin-2-yl]piperidin-4-yl}-5-(1H-1,2,4-triazol-1-yl)pyrazine-2-carboxamide | 477.2 | method 23:<br>$t_R =$<br>4.76 min |
| 47 | 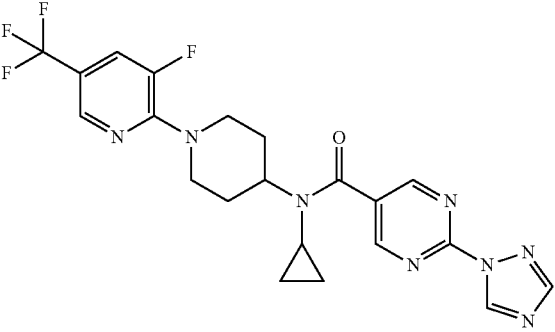<br>N-cyclopropyl-N-{1-[3-fluoro-5-(trifluoromethyl)pyridin-2-yl]piperidin-4-yl}-2-(1H-1,2,4-triazol-1-yl)pyrimidine-5-carboxamide | 477.2 | method 23:<br>$t_R =$<br>4.09 min |
| 48 | 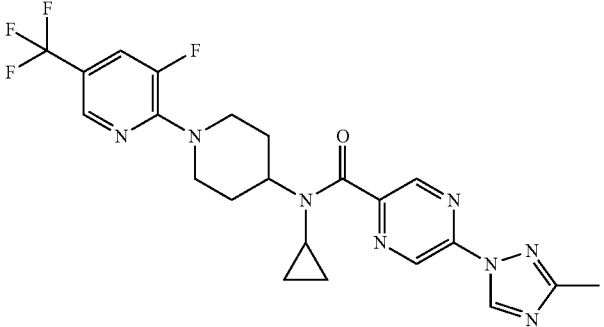<br>N-cyclopropyl-N-{1-[3-fluoro-5-(trifluoromethyl)pyridin-2-yl]piperidin-4-yl}-5-(3-methyl-1H-1,2,4-triazol-1-yl)pyrazine-2-carboxamide | 491.2 | method 23:<br>$t_R =$<br>4.63 min |

TABLE 1-continued

| Example | Structure/Name | Mass spectrum (APCI): m/z | LC |
|---|---|---|---|
| 49 | 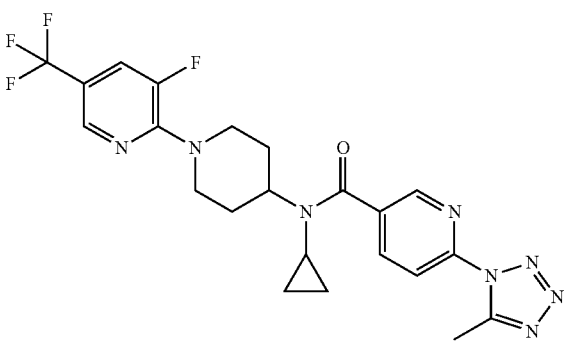<br>N-cyclopropyl-N-{1-[3-fluoro-5-(trifluoromethyl)pyridin-2-yl]piperidin-4-yl}-6-(5-methyl-1H-1,2,3,4-tetrazol-1-yl)pyridine-3-carboxamide | 491.2 | method 23:<br>$t_R$ =<br>4.51 min |
| 50 | 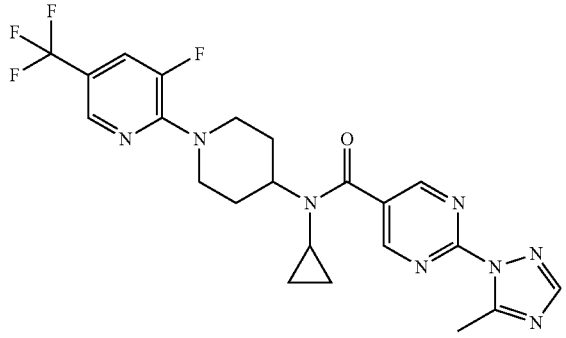<br>N-cyclopropyl-N-{1-[3-fluoro-5-(trifluoromethyl)pyridin-2-yl]piperidin-4-yl}-2-(5-methyl-1H-1,2,4-triazol-1-yl)pyrimidine-5-carboxamide | 491.2 | method 23:<br>$t_R$ =<br>4.20 min |
| 51 | 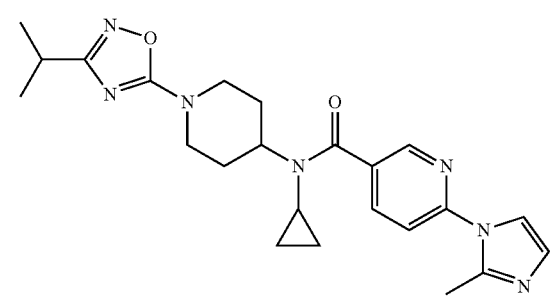<br>N-cyclopropyl-6-(2-methyl-1H-imidazol-1-yl)-N-{1-[3-(propan-2-yl)-1,2,4-oxadiazol-5-yl]piperidin-4-yl}pyridine-3-carboxamide | 436.3 | method 23:<br>$t_R$ =<br>3.24 min |

TABLE 1-continued

| Example | Structure/Name | Mass spectrum (APCI): m/z | LC |
|---|---|---|---|
| 52 | 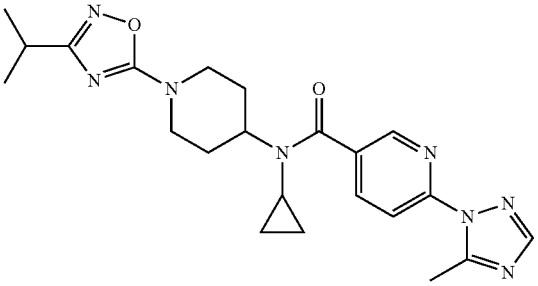<br>N-cyclopropyl-6-(5-methyl-1H-1,2,4-triazol-1-yl)-N-{1-[3-(propan-2-yl)-1,2,4-oxadiazol-5-yl]piperidin-4-yl}pyridine-3-carboxamide | 437.2 | method 23:<br>$t_R$ = 2.91 min |
| 53 | 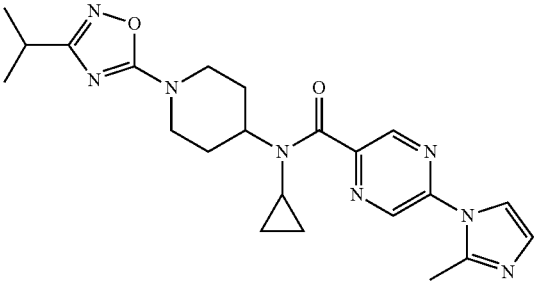<br>N-cyclopropyl-5-(2-methyl-1H-imidazol-1-yl)-{1-[3-(propan-2-yl)-1,2,4-oxadiazol-5-yl]piperidin-4-yl}pyrazine-2-carboxamide | 437.3 | method 23:<br>$t_R$ = 3.23 min |
| 54 | 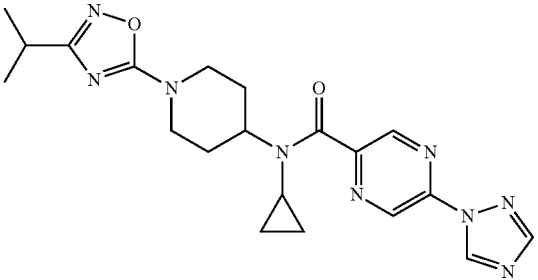<br>N-cyclopropyl-N-{1-[3-(propan-2-yl)-1,2,4-oxadiazol-5-yl]piperidin-4-yl}-5-(1H-1,2,4-triazol-1-yl)pyrazine-2-carboxamide | 424.2 | method 23:<br>$t_R$ = 3.49 min |

TABLE 1-continued

| Example | Structure/Name | Mass spectrum (APCI): m/z | LC |
|---|---|---|---|
| 55 | 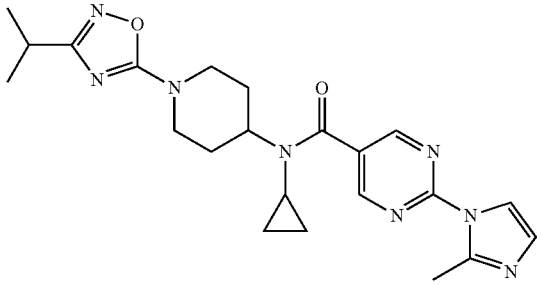<br>N-cyclopropyl-2-(2-methyl-1H-imidazol-1-yl)-N-{1-[3-(propan-2-yl)-1,2,4-oxadiazol-5-yl]piperidin-4-yl}pyrimidine-5-carboxamide | 437.3 | method 23:<br>$t_R$ = 3.41 min |
| 56 | 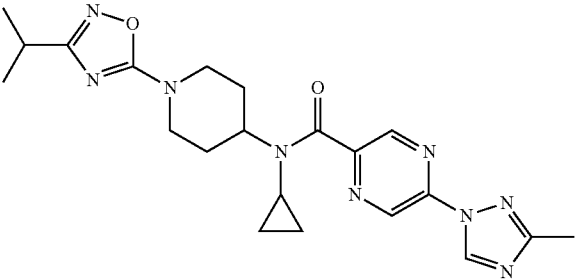<br>N-cyclopropyl-5-(3-methyl-1H-1,2,4-triazol-1-yl)-N-{1-[3-(propan-2-yl)-1,2,4-oxadiazol-5-yl]piperidin-4-yl}pyrazine-2-carboxamide | 438.2 | method 23:<br>$t_R$ = 3.55 min |
| 57 | 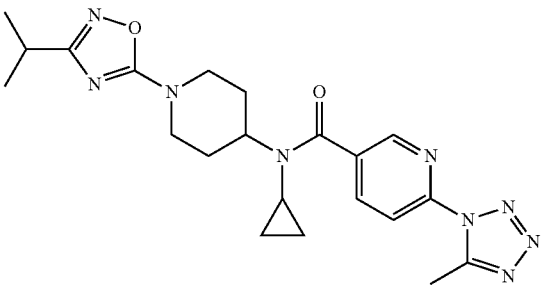<br>N-cyclopropyl-6-(5-methyl-1H-1,2,3,4-tetrazol-1-yl)-N-{1-[3-(propan-2-yl)-1,2,4-oxadiazol-5-yl]piperidin-4-yl}pyridine-3-carboxamide | 438.2 | method 23:<br>$t_R$ = 3.10 min |

TABLE 1-continued

| Example | Structure/Name | Mass spectrum (APCI): m/z | LC |
|---|---|---|---|
| 58 | 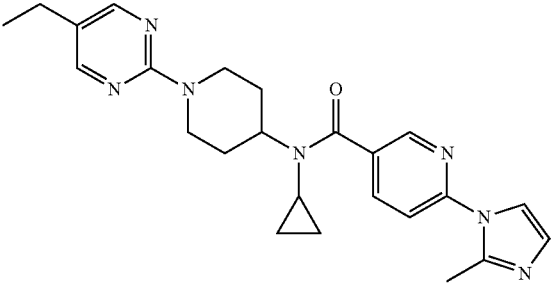<br>N-cyclopropyl-N-[1-(5-ethylpyrimidin-2-yl)piperidin-4-yl]-6-(2-methyl-1H-imidazol-1-yl)pyridine-3-carboxamide | 432.3 | method 23:<br>$t_R =$<br>4.20 min |
| 59 | 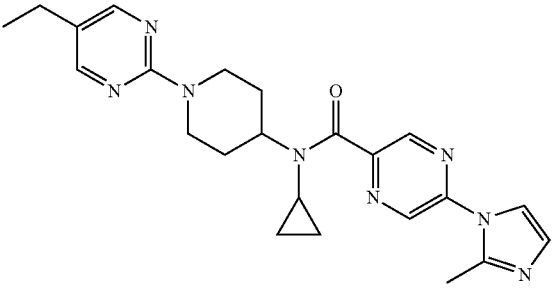<br>N-cyclopropyl-N-[1-(5-ethylpyrimidin-2-yl)piperidin-4-yl]-5-(2-methyl-1H-imidazol-1-yl)pyrazine-2-carboxamide | 433.3 | method 23:<br>$t_R =$<br>3.76 min |
| 60 | 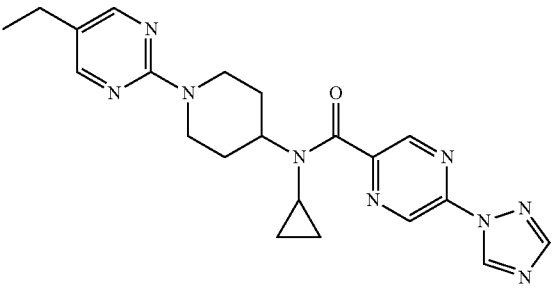<br>N-cyclopropyl-N-[1-(5-ethylpyrimidin-2-yl)piperidin-4-yl]-5-(1H-1,2,4-triazol-1-yl)pyrazine-2-carboxamide | 420.2 | method 23:<br>$t_R =$<br>3.81 min |

| Example | Structure/Name | Mass spectrum (APCI): m/z | LC |
|---|---|---|---|
| 61 | 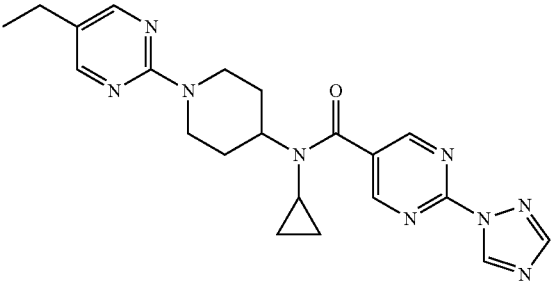<br>N-cyclopropyl-N-[1-(5-ethylpyrimidin-2-yl)piperidin-4-yl]-2-(1H-1,2,4-triazol-1-yl)pyrimidine-5-carboxamide | 420.2 | method 23: $t_R$ = 3.41 min |
| 62 | 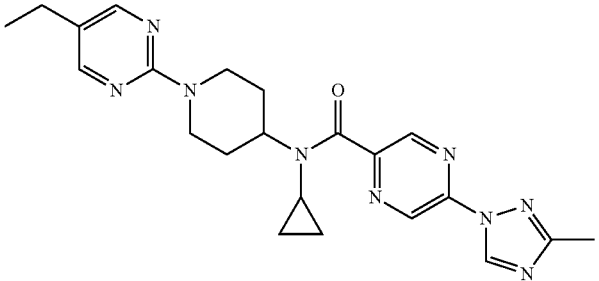<br>N-cyclopropyl-N-[1-(5-ethylpyrimidin-2-yl)piperidin-4-yl]-5-(3-methyl-1H-1,2,4-triazol-1-yl)pyrazine-2-carboxamide | 434.3 | method 23: $t_R$ = 5.21 min |
| 63 | 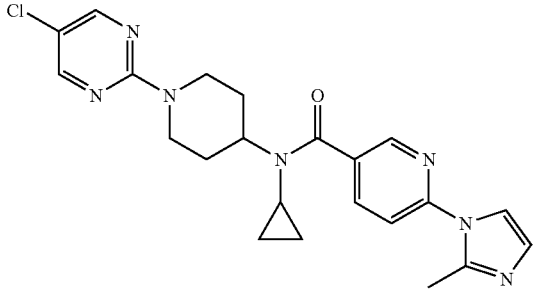<br>N-[1-(5-chloropyrimidin-2-yl)piperidin-4-yl]-N-cyclopropyl-6-(2-methyl-1H-imidazol-1-yl)pyridine-3-carboxamide | 438.2 | method 23: $t_R$ = 3.83 min |

TABLE 1-continued

| Example | Structure/Name | Mass spectrum (APCI): m/z | LC |
|---|---|---|---|
| 64 | 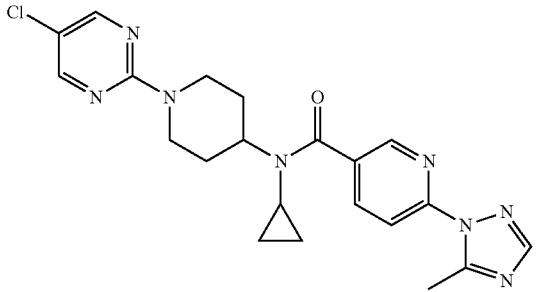<br>N-[1-(5-chloropyrimidin-2-yl)piperidin-4-yl]-N-cyclopropyl-6-(5-methyl-1H-1,2,4-triazol-1-yl)pyridine-3-carboxamide | 439.2 | method 23: $t_R$ = 3.97 min |
| 65 | 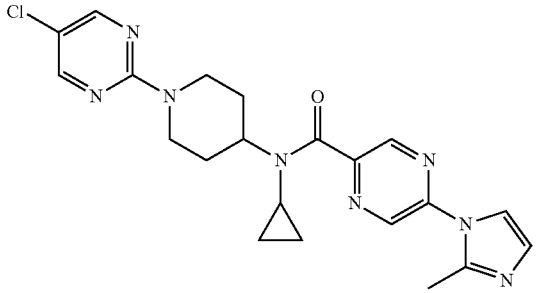<br>N-[1-(5-chloropyrimidin-2-yl)piperidin-4-yl]-N-cyclopropyl-5-(2-methyl-1H-imidazol-1-yl)pyrazine-2-carboxamide | 439.2 | method 23: $t_R$ = 4.00 min |
| 66 | 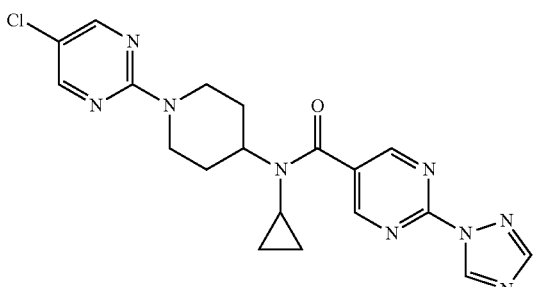<br>N-[1-(5-chloropyrimidin-2-yl)piperidin-4-yl]-N-cyclopropyl-5-(1H-1,2,4-triazol-1-yl)pyrazine-2-carboxamide | 426.2 | method 23: $t_R$ = 4.07 min |

TABLE 1-continued

| Example | Structure/Name | Mass spectrum (APCI): m/z | LC |
|---|---|---|---|
| 67 | 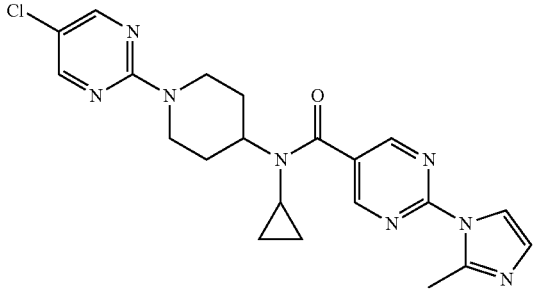<br>N-[1-(5-chloropyrimidin-2-yl)piperidin-4-yl]-N-cyclopropyl-2-(2-methyl-1H-imidazol-1-yl)pyrimidine-5-carboxamide | 439.2 | method 23:<br>$t_R$ = 4.09 min |
| 68 | 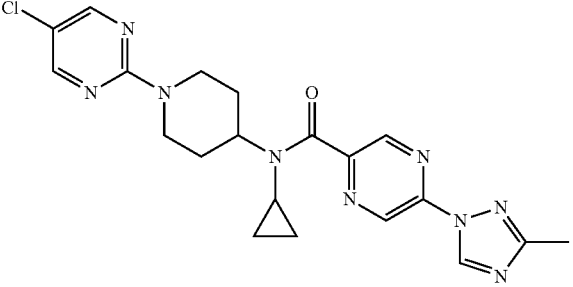<br>N-[1-(5-chloropyrimidin-2-yl)pyridin-4-yl]-N-cyclopropyl-5-(3-methyl-1H-1,2,4-triazol-1-yl)pyrazine-2-carboxamide | 440.2 | method 23:<br>$t_R$ = 4.07 min |
| 69 | 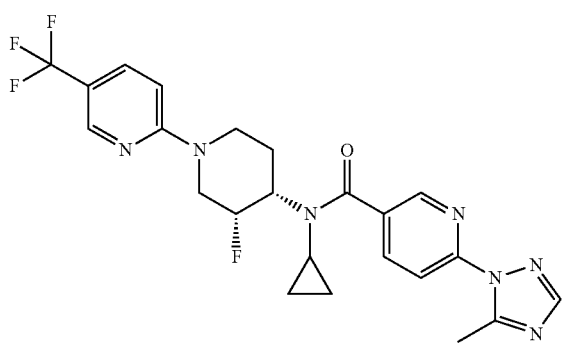<br>N-cyclopropyl-N-[(3R,4S)-3-fluoro-1-[5-(trifluoromethyl)pyridin-2-yl]piperidin-4-yl]-6-(5-methyl-1H-1,2,4-triazol-1-yl)pyridine-3-carboxamide | 490.2 | method 23:<br>$t_R$ = 4.20 min |

TABLE 1-continued

| Example | Structure/Name | Mass spectrum (APCI): m/z | LC |
|---|---|---|---|
| 70 | N-cyclopropyl-N-[(3R,4S)-3-fluoro-1-[5-(trifluoromethyl)pyridin-2-yl]piperidin-4-yl]-6-(5-methyl-1H-1,2,3,4-tetrazol-1-yl)pyridine-3-carboxamide | 491.2 | method 23: $t_R$ = 4.34 min |
| 71 | N-cyclopropyl-N-[(3R,4S)-3-fluoro-1-[5-(trifluoromethyl)pyridin-2-yl]piperidin-4-yl]-5-(1H-1,2,4-triazol-1-yl)pyrazine-2-carboxamide | 477.2 | method 23: $t_R$ = 4.18 min |
| 72 | N-cyclopropyl-N-[(3R,4S)-3-fluoro-1-[5-(trifluoromethyl)pyridin-2-yl]piperidin-4-yl]-2-(2-methyl-1H-imidazol-1-yl)pyrimidine-5-carboxamide | 490.2 | method 23: $t_R$ = 4.30 min |

TABLE 1-continued

| Example | Structure/Name | Mass spectrum (APCI): m/z | LC |
|---|---|---|---|
| 73 | 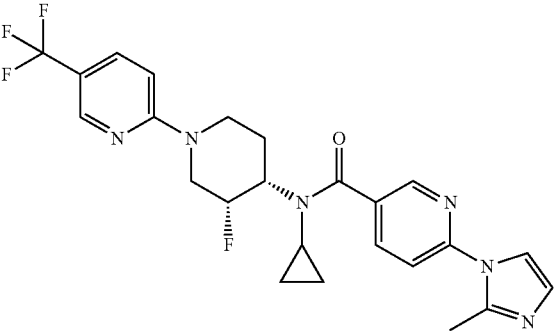<br>N-cyclopropyl-N-[(3R,4S)-3-fluoro-1-[5-(trifluoromethyl)pyridin-2-yl]piperidin-4-yl]-6-(2-methyl-1H-imidazol-1-yl)pyridine-3-carboxamide | 489.2 | method 23:<br>$t_R =$<br>4.04 min |
| 74 | 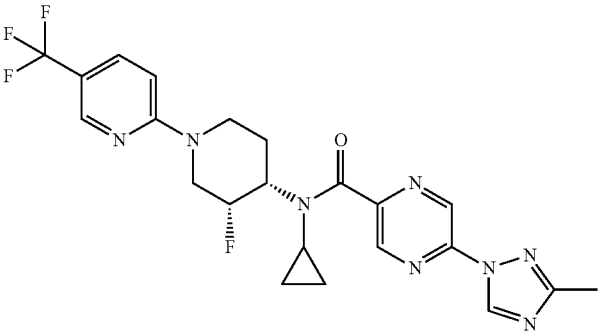<br>N-cyclopropyl-N-[(3R,4S)-3-fluoro-1-[5-(trifluoromethyl)pyridin-2-yl]piperidin-4-yl]-5-(3-methyl-1H-1,2,4-triazol-1-yl)pyrazine-2-carboxamide | 491.2 | method 23:<br>$t_R =$<br>4.25 min |
| 75 | 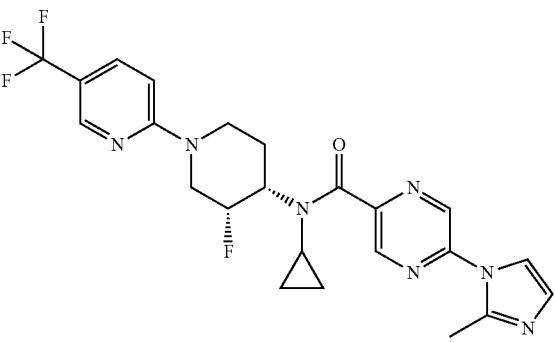<br>N-cyclopropyl-N-[(3R,4S)-3-fluoro-1-[5-(trifluoromethyl)pyridin-2-yl]piperidin-4-yl]-5-(2-methyl-1H-imidazol-1-yl)pyrazine-2-carboxamide | 490.2 | method 23:<br>$t_R =$<br>4.12 min |

TABLE 1-continued

| Example | Structure/Name | Mass spectrum (APCI): m/z | LC |
|---|---|---|---|
| 76 | 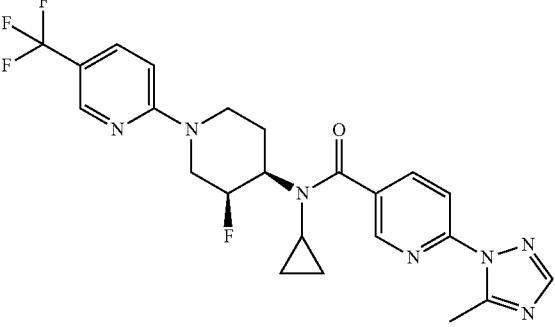<br>N-cyclopropyl-N-[(3S,4R)-3-fluoro-1-[5-(trifluoromethyl)pyridin-2-yl]piperidin-4-yl]-6-(5-methyl-1H-1,2,4-triazol-1-yl)pyridine-3-carboxamide | 490.2 | method 23:<br>$t_R$ =<br>4.11 min |
| 77 | 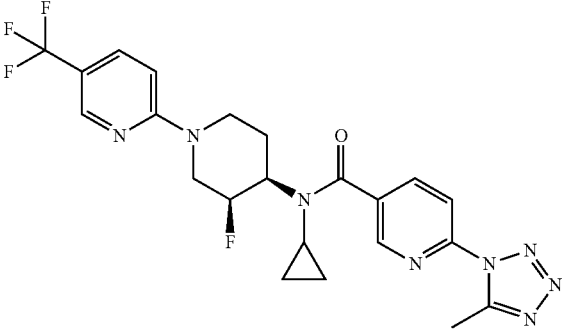<br>N-cyclopropyl-N-[(3S,4R)-3-fluoro-1-[5-(trifluoromethyl)pyridin-2-yl]piperidin-4-yl]-6-(5-methyl-1H-1,2,3,4-tetrazol-1-yl)pyridine-3-carboxamide | 491.2 | method 23:<br>$t_R$ =<br>4.27 min |
| 78 | 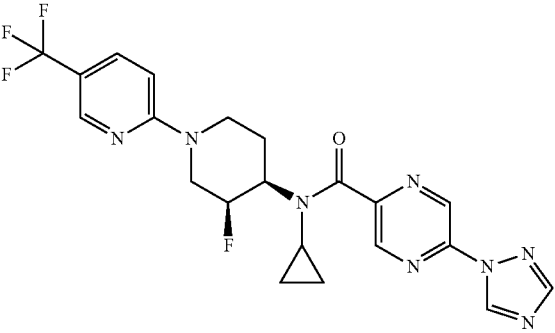<br>N-cyclopropyl-N-[(3S,4R)-3-fluoro-1-[5-(trifluoromethyl)pyridin-2-yl]piperidin-4-yl]-5-(1H-1,2,4-triazol-1-yl)pyrazine-2-carboxamide | 477.2 | method 23:<br>$t_R$ =<br>3.34 min |

TABLE 1-continued

| Example | Structure/Name | Mass spectrum (APCI): m/z | LC |
|---|---|---|---|
| 79 | N-cyclopropyl-N-[(3S,4R)-3-fluoro-1-[5-(trifluoromethyl)pyridin-2-yl]piperidin-4-yl]-2-(2-methyl-1H-imidazol-1-yl)pyrimidine-5-carboxamide | 490.2 | method 23: $t_R$ = 4.13 min |
| 80 | N-cyclopropyl-N-[(3S,4R)-3-fluoro-1-[5-(trifluoromethyl)pyridin-2-yl]piperidin-4-yl]-2-(1H-1,2,4-triazol-1-yl)pyrimidine-5-carboxamide | 477.2 | method 23: $t_R$ = 4.69 min |
| 81 | N-cyclopropyl-N-[(3S,4R)-3-fluoro-1-[5-(trifluoromethyl)pyridin-2-yl]piperidin-4-yl]-6-(2-methyl-1H-imidazol-1-yl)pyridine-3-carboxamide | 489.2 | method 23: $t_R$ = 3.90 min |

TABLE 1-continued

| Example | Structure/Name | Mass spectrum (APCI): m/z | LC |
|---|---|---|---|
| 82 | 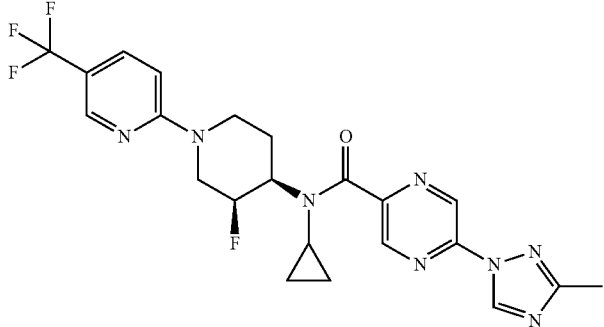<br>N-cyclopropyl-N-[(3S,4R)-3-fluoro-1-[5-(trifluoromethyl)pyridin-2-yl]piperidin-4-yl]-5-(3-methyl-1H-1,2,4-triazol-1-yl)pyrazine-2-carboxamide | 491.2 | method 23: $t_R$ = 4.12 min |
| 83 | 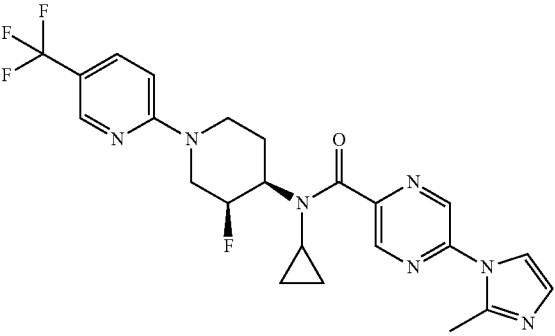<br>N-cyclopropyl-N-[(3S,4R)-3-fluoro-1-[5-(trifluoromethyl)pyridin-2-yl]piperidin-4-yl]-5-(2-methyl-1H-imidazol-1-yl)pyrazine-2-carboxamide | 490.2 | method 23: $t_R$ = 3.97 min |
| 84 | 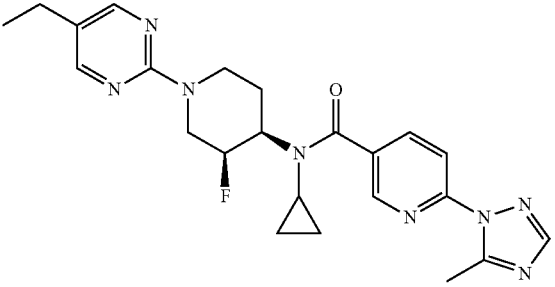<br>N-cyclopropyl-N-[(3S,4R)-1-(5-ethylpyrimidin-2-yl)-3-fluoropiperidin-4-yl]-6-(5-methyl-1H-1,2,4-triazol-1-yl)pyridine-3-carboxamide | 451.2 | method 23: $t_R$ = 3.81 min |

TABLE 1-continued

| Example | Structure/Name | Mass spectrum (APCI): m/z | LC |
|---|---|---|---|
| 85 | 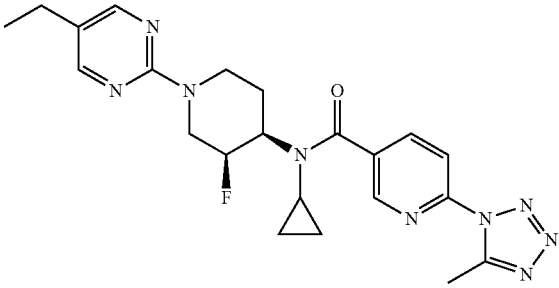<br>N-cyclopropyl-N-[(3S,4R)-1-(5-ethylpyrimidin-2-yl)-3-fluoropiperidin-4-yl]-6-(5-methyl-1H-1,2,3,4-tetrazol-1-yl)pyridine-3-carboxamide | 452.3 | method 23: $t_R$ = 3.99 min |
| 86 | 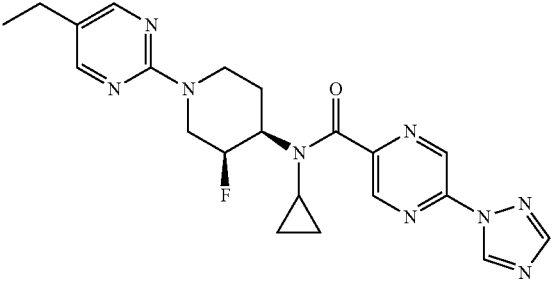<br>N-cyclopropyl-N-[(3S,4R)-1-(5-ethylpyrimidin-2-yl)-3-fluoropiperidin-4-yl]-5-(1H-1,2,4-triazol-1-yl)pyrazine-2-carboxamide | 438.2 | method 23: $t_R$ = 3.86 min |
| 87 | 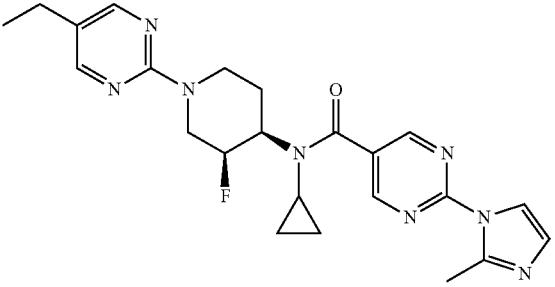<br>N-cyclopropyl-N-[(3S,4R)-1-(5-ethylpyrimidin-2-yl)-3-fluoropiperidin-4-yl]-2-(2-methyl-1H-imidazol-1-yl)pyrimidine-5-carboxamide | 451.3 | method 23: $t_R$ = 4.02 min |

TABLE 1-continued

| Example | Structure/Name | Mass spectrum (APCI): m/z | LC |
|---|---|---|---|
| 88 | 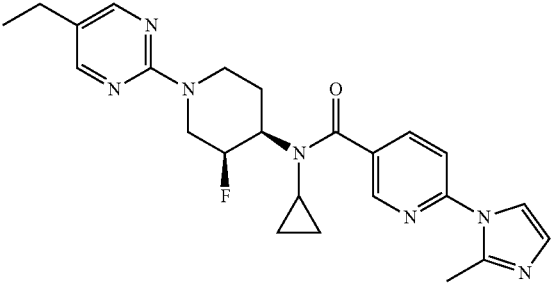<br>N-cyclopropyl-N-[(3S,4R)-1-(5-ethylpyrimidin-2-yl)-3-fluoropiperidin-4-yl]-6-(2-methyl-1H-imidazol-1-yl)pyridine-3-carboxamide | 450.3 | method 23: $t_R$ = 3.53 min |
| 89 | 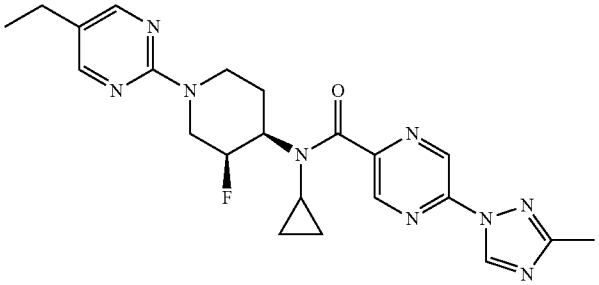<br>N-cyclopropyl-N-[(3R,4R)-1-(5-ethylpyrimidin-2-yl)-3-fluoropiperidin-4-yl]-5-(3-methyl-1H-1,2,4-triazol-1-yl)pyrazine-2-carboxamide | 452.2 | method 23: $t_R$ = 3.88 min |
| 90 | 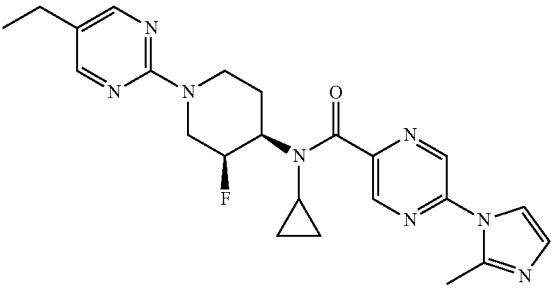<br>N-cyclopropyl-N-[(3S,4R)-1-(5-ethylpyrimidin-2-yl)-3-fluoropiperidin-4-yl]-5-(2-methyl-1H-imidazol-1-yl)pyrazine-2-carboxamide | 451.3 | method 23: $t_R$ = 3.77 min |

TABLE 1-continued

| Example | Structure/Name | Mass spectrum (APCI): m/z | LC |
|---|---|---|---|
| 91 | 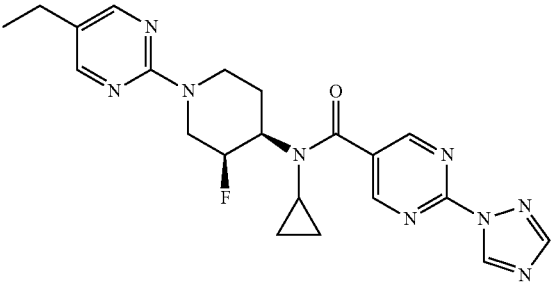<br>N-cyclopropyl-N-[(3S,4R)-1-(5-ethylpyrimidin-2-yl)-3-fluoropiperidin-4-yl]-2-(1H-1,2,4-triazol-1-yl)pyrimidine-5-carboxamide | 438.2 | method 23:<br>$t_R$ =<br>2.86 min |
| 92 | 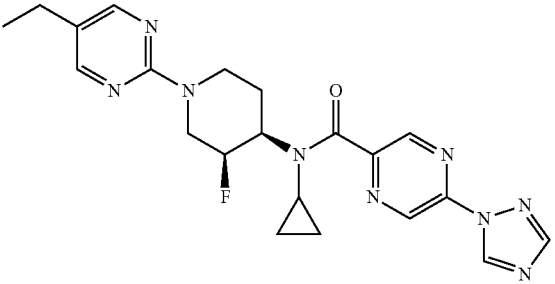<br>N-cyclopropyl-N-[(3R,4S)-1-(5-ethylpyrimidin-2-yl)-3-fluoropiperidin-4-yl]-5-(1H-1,2,4-triazol-1-yl)pyrazine-2-carboxamide | 438.2 | method 23:<br>$t_R$ =<br>3.02 min |
| 93 | 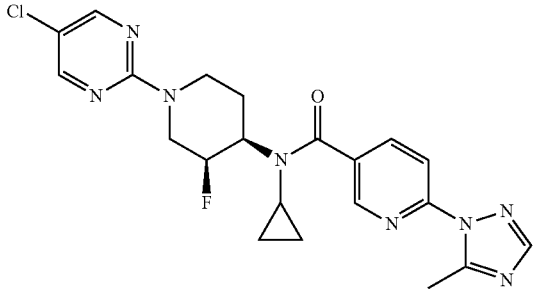<br>N-[(3S,4R)-1-(5-chloropyrimidin-2-yl)-3-fluoropiperidin-4-yl]-N-cyclopropyl-6-(5-methyl-1H-1,2,4-triazol-1-yl)pyridine-3-carboxamide | 457.2 | method 23:<br>$t_R$ =<br>3.90 min |

TABLE 1-continued

| Example | Structure/Name | Mass spectrum (APCI): m/z | LC |
|---|---|---|---|
| 94 | 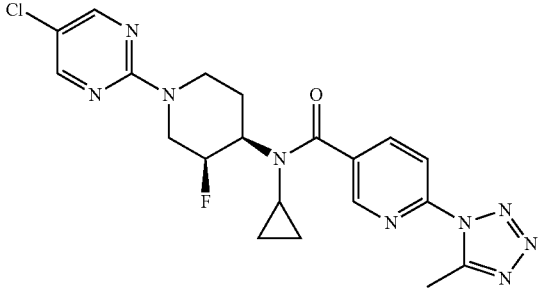<br>N-[(3S,4R)-1-(5-chloropyrimidin-2-yl)-3-fluoropiperidin-4-yl]-N-cyclopropyl-6-(5-methyl-1H-1,2,3,4-tetrazol-1-yl)pyridine-3-carboxamide | 458.2 | method 23:<br>$t_R$ =<br>4.05 min |
| 95 | 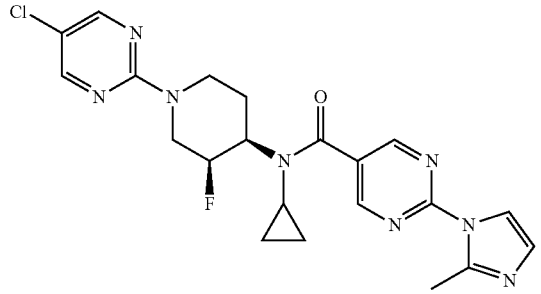<br>N-[(3S,4R)-1-(5-chloropyrimidin-2-yl)-3-fluoropiperidin-4-yl]-N-cyclopropyl-2-(2-methyl-1H-imidazol-1-yl)pyrimidine-5-carboxamide | 457.2 | method 23:<br>$t_R$ =<br>3.93 min |
| 96 | 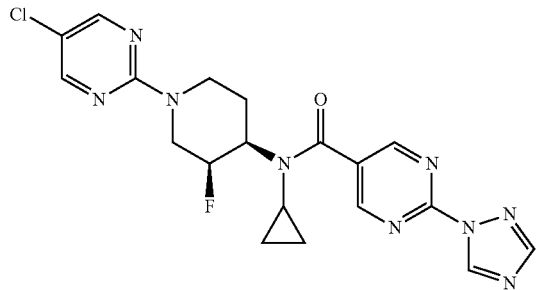<br>N-[(3S,4R)-1-(5-chloropyrimidin-2-yl)-3-fluoropiperidin-4-yl]-N-cyclopropyl-2-(1H-1,2,4-triazol-1-yl)pyrimidine-5-carboxamide | 444.2 | method 23:<br>$t_R$ =<br>3.46 min |

TABLE 1-continued

| Example | Structure/Name | Mass spectrum (APCI): m/z | LC |
|---|---|---|---|
| 97 | 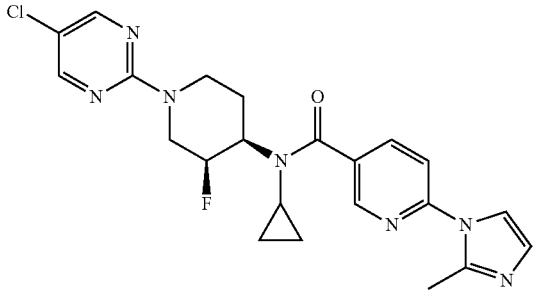<br>N-[(3S,4R)-1-(5-chloropyrimidin-2-yl)-3-fluoropiperidin-4-yl]-N-cyclopropyl-6-(2-methyl-1H-imidazol-1-yl)pyridine-3-carboxamide | 456.2 | method 23:<br>$t_R =$<br>3.72 min |
| 98 | 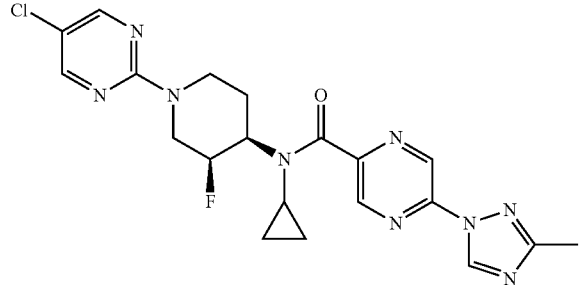<br>N-[(3S,4R)-1-(5-chloropyrimidin-2-yl)-3-fluoropiperidin-4-yl]-N-cyclopropyl-5-(3-methyl-1H-1,2,4-triazol-1-yl)pyrazine-2-carboxamide | 458.2 | method 23:<br>$t_R =$<br>3.93 min |
| 99 | 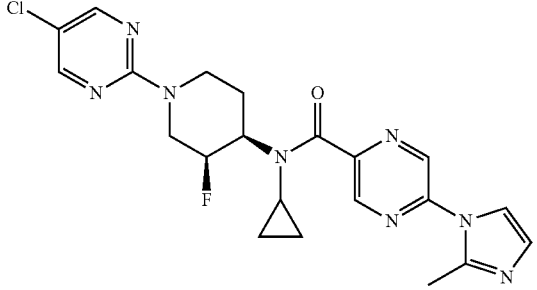<br>N-[(3S,4R)-1-(5-chloropyrimidin-2-yl)-3-fluoropiperidin-4-yl]-N-cyclopropyl-5-(2-methyl-1H-imidazol-1-yl)pyrazine-2-carboxamide | 457.2 | method 23:<br>$t_R =$<br>3.74 min |

TABLE 1-continued

| Example | Structure/Name | Mass spectrum (APCI): m/z | LC |
|---|---|---|---|
| 100 | 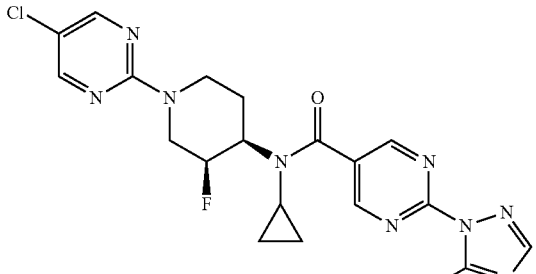<br>N-[(3S,4R)-1-(5-chloropyrimidin-2-yl)-3-fluoropiperidin-4-yl]-N-cyclopropyl-2-(5-methyl-1H-1,2,4-triazol-1-yl)pyrimidine-5-carboxamide | 458.2 | method 23: $t_R$ = 3.53 min |
| 101 | 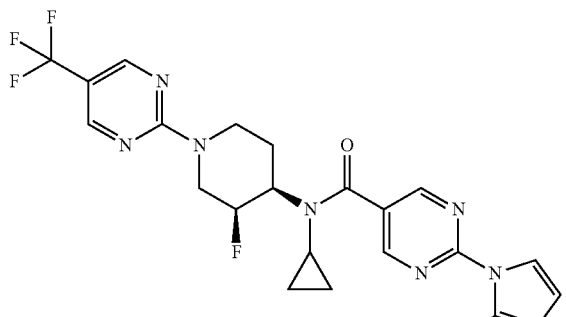<br>N-cyclopropyl-N-[(3S,4R)-3-fluoro-1-[5-(trifluoromethyl)pyrimidin-2-yl]piperidin-4-yl]-2-(2-methyl-1H-imidazol-1-yl)pyrimidine-5-carboxamide | 491.2 | method 23: $t_R$ = 4.13 min |
| 102 | 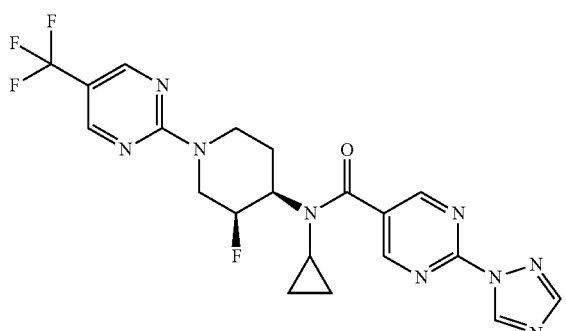<br>N-cyclopropyl-N-[(3S,4R)-3-fluoro-1-[5-(trifluoromethyl)pyrimidin-2-yl]piperidin-4-yl]-2-(1H-1,2,4-triazol-1-yl)pyrimidine-5-carboxamide | 478.2 | method 23: $t_R$ = 3.70 min |

TABLE 1-continued

| Example | Structure/Name | Mass spectrum (APCI): m/z | LC |
|---|---|---|---|
| 103 | 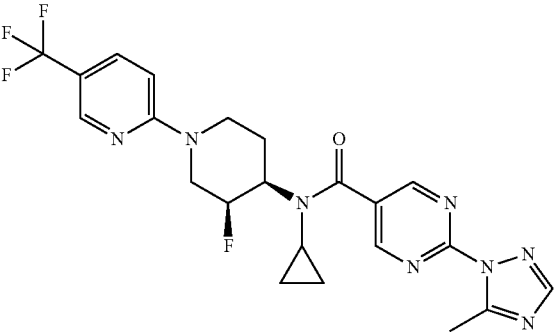<br>N-cyclopropyl-N-[(3S,4R)-3-fluoro-1-[5-(trifluoromethyl)pyridin-2-yl]piperidin-4-yl]-2-(5-methyl-1H-1,2,4-triazol-1-yl)pyrimidine-5-carboxamide | 491.2 | method 23:<br>$t_R$ = 3.79 min |
| 104 | 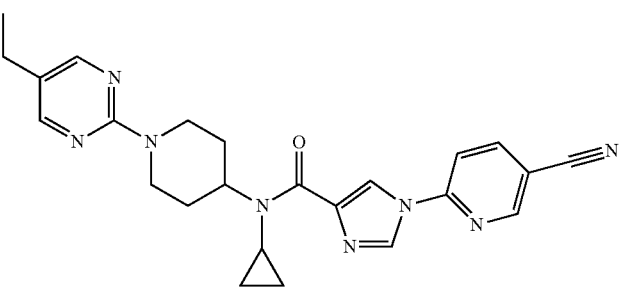<br>1-(5-cyanopyridin-2-yl)-N-cyclopropyl-N-[1-(5-ethylpyrimidin-2-yl)piperidin-4-yl]-1H-imidazole-4-carboxamide | 443.2 | method 23:<br>$t_R$ = 2.60 min |
| 105 | 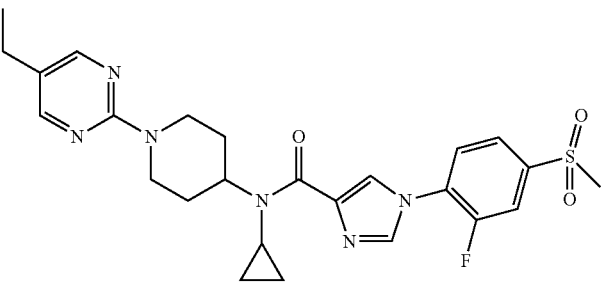<br>N-cyclopropyl-N-[1-(5-ethylpyrimidin-2-yl)piperidin-4-yl]-1-(2-fluoro-4-methanesulfonylphenyl)-1H-imidazole-4-carboxamide | 513.2 | method 23:<br>$t_R$ = 2.53 min |

TABLE 1-continued

| Example | Structure/Name | Mass spectrum (APCI): m/z | LC |
|---|---|---|---|
| 106 | 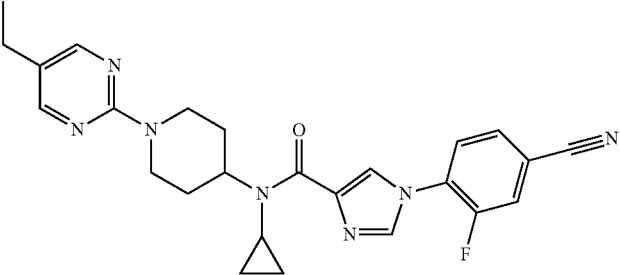<br>1-(4-cyano-2-fluorophenyl)-N-cyclopropyl-N-[1-(5-ethylpyrimidin-2-yl)piperidin-4-yl]-1H-imidazole-4-carboxamide | 460.2 | method 23: $t_R$ = 2.72 min |
| 107 | 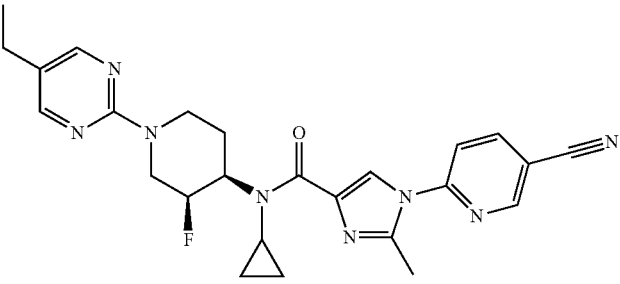<br>1-(5-cyanopyridin-2-yl)-N-cyclopropyl-N-[(3S,4R)-1-(5-ethylpyrimidin-2-yl)-3-fluoropiperidin-4-yl]-1H-imidazole-4-carboxamide | 461.2 | method 23: $t_R$ = 3.00 min |
| 108 | 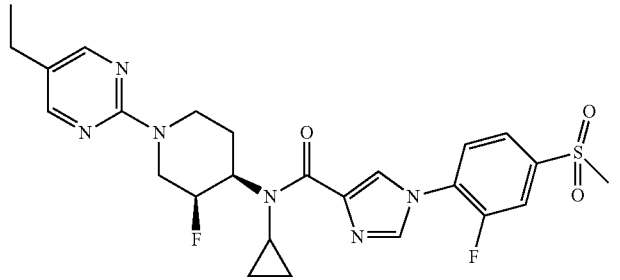<br>N-cyclopropyl-N-[(3S,4R)-1-(5-ethylpyrimidin-2-yl)-3-fluoropiperidin-4-yl]-1-(2-fluoro-4-methanesulfonylphenyl)-1H-imidazole-4-carboxamide | 531.2 | method 23: $t_R$ = 2.87 min |

TABLE 1-continued

| Example | Structure/Name | Mass spectrum (APCI): m/z | LC |
|---|---|---|---|
| 109 | 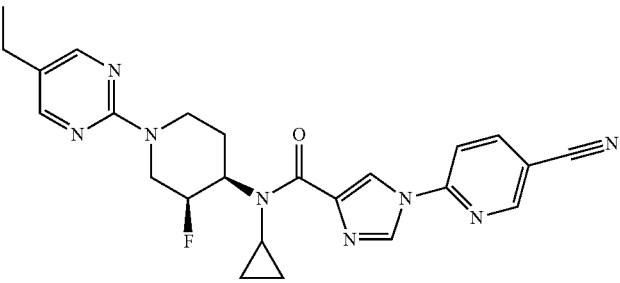

1-(4-cyano-2-fluorophenyl)-N-cyclopropyl-N-[(3S,4R)-1-(5-ethylpyrimidin-2-yl)-3-fluoropiperidin-4-yl]-1H-imidazole-4-carboxamide | 478.2 | method 23: $t_R$ = 3.12 min |
| 110 | 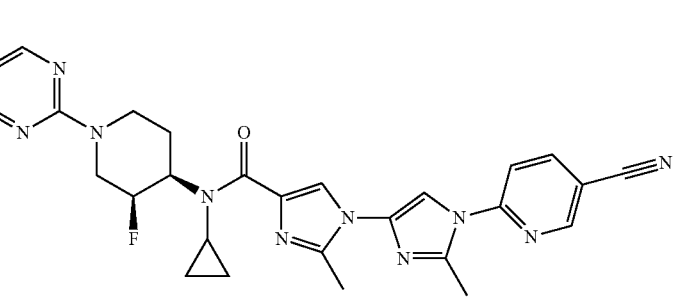

1-(5-cyanopyridin-2-yl)-N-cyclopropyl-N-[(3S,4R)-1-(5-ethylpyrimidin-2-yl)-3-fluoropiperidin-4-yl]-2-methyl-1H-imidazole-4-carboxamide | 475.2 | method 23: $t_R$ = 2.58 min |
| 111 | 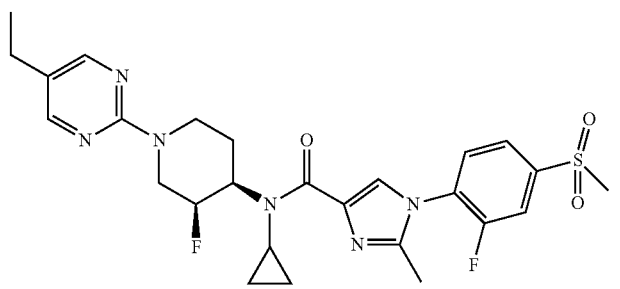

N-cyclopropyl-N-[(3S,4R)-1-(5-ethylpyrimidin-2-yl)-3-fluoropiperidin-4-yl]-1-(2-fluoro-4-methanesulfonylphenyl)-2-methyl-1H-imidazole-4-carboxamide | 545.2 | method 23: $t_R$ = 2.53 min |

TABLE 1-continued

| Example | Structure/Name | Mass spectrum (APCI): m/z | LC |
|---|---|---|---|
| 112 | 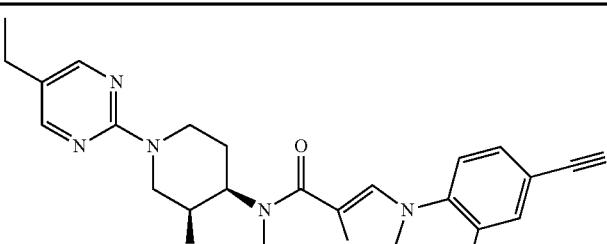<br>1-(4-cyano-2-fluorophenyl)-N-cyclopropyl-N-[(3S,4R)-1-(5-ethylpyrimidin-2-yl)-3-fluoropiperidin-4-yl]-2-methyl-1H-imidazole-4-carboxamide | 492.2 | method 23: $t_R$ = 2.65 min |

The invention claimed is:

1. A compound of formula I

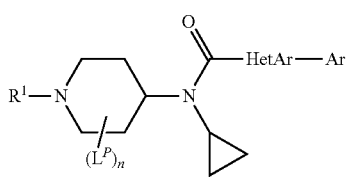

wherein

R$^1$ is selected from the group consisting of a 5- or 6-membered heteroaromatic ring which contains 1, 2 or 3 heteroatoms independently of each other selected from N, NR$^N$, O and S; and wherein optionally a second carbocyclic ring is condensed to said heteroaromatic ring, wherein said second carbocyclic ring is unsaturated or aromatic and 5- or 6-membered and may optionally contain 1, 2 or 3 heteroatoms independently of each other selected from N, NR$^N$, O and S, and wherein in said second carbocyclic ring 1 or 2 —CH$_2$-groups are optionally replaced by —N(R$^N$)—, —C(=O)—, —S(=O)— or —S(=O)$_2$—, and wherein each of said heteroaromatic ring and/or second carbocyclic ring independently of each other may be optionally substituted with one or more substituents selected from L$^{Ar}$; and wherein said heteroaromatic ring or said second carbocyclic ring is optionally substituted with a group R$^2$; and each R$^N$ is independently selected from the group consisting of H, C$_{1-4}$-alkyl, C$_{1-4}$-alkyl-C(=O)—, and C$_{1-4}$-alkyl-S(=O)$_2$—; and HetAr is selected from the group consisting of a 5- or 6-membered heteroaromatic ring which contains 1, 2 or 3 heteroatoms independently of each other selected from N, NR$^N$, O and S;

wherein each heteroaromatic ring may be optionally substituted with one or more substituents selected from L$^Q$; and Ar is selected from the group consisting of a phenyl ring, a tetrazolyl ring, and a 5- or 6-membered heteroaromatic ring which contains 1, 2 or 3 heteroatoms independently of each other selected from N, NR$^N$, O and S; and wherein optionally a second carbocyclic ring is condensed to said phenyl ring or heteroaromatic ring, wherein said second carbocyclic ring is unsaturated or aromatic and 5- or 6-membered and may contain 1, 2 or 3 heteroatoms independently of each other selected from N, NR$^N$, O and S, and wherein in said second carbocyclic ring 1 or 2 —CH$_2$-groups are optionally replaced by —N(R$^N$)—, —C(=O)—, —S(=O)— or —S(=O)$_2$—, and wherein each of said phenyl ring, heteroaromatic ring and/or second carbocyclic ring independently of each other may optionally be substituted with one or more substituents selected from L$^{Ar}$; and wherein said phenyl ring, a tetrazolyl ring, heteroaromatic ring or second carbocyclic ring are optionally substituted with a group T; and T is selected from the group consisting of F, Cl, Br, I, CN, OH, NO$_2$, C$_{1-6}$-alkyl-, C$_{2-6}$-alkenyl-, C$_{2-6}$-alkynyl-, C$_{3-6}$-cycloalkyl, C$_{1-6}$-alkyl-O—, C$_{3-6}$-cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)—(R$^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, NR$^N$, O and S; and wherein heterocyclyl is a 4- to 7-membered unsaturated or saturated carbocyclic ring in which 1, 2, or 3 —$CH_2$-groups independently of each other are replaced by $NR^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from $L^{Ar}$; and $R^{NT1}$ is selected from the group consisting of H, $C_{1-6}$-alkyl, $C_{3-6}$-cycloalkyl, $C_{1-6}$-alkyl-C(=O)—, $C_{1-6}$-alkyl-S(=O)$_2$, heterocyclyl, aryl and heteroaryl, wherein each alkyl and cylcoalkyl group may be optionally substituted with one or more substituents independently of each other selected from the group consisting of F, OH, CN, $C_{1-4}$-alkyl, $C_{1-4}$-alkyl-O—, $(R^N)_2N$, $C_{1-4}$-alkyl-S(=O)$_2$—, $C_{3-6}$-cycloalkyl, heterocyclyl, phenyl and heteroaryl; and wherein heterocyclyl is a $C_{4-7}$-cycloalkyl ring in which 1 or 2 —$CH_2$-groups independently of each other are replaced by $NR^N$, O, C(=O), S, S(=O) or S(=O)$_2$; and wherein heterocyclyl may be optionally substituted with one or more substituents independently of each other selected from F, $C_{1-4}$-alkyl, $(R^N)_2N$, OH and $C_{1-4}$-alkyl-O—; and wherein aryl is phenyl or naphthyl; and wherein heteroaryl is a 5- or 6-membered aromatic carbocyclic ring which contains 1, 2 or 3 heteroatoms independently of each other selected from N, $NR^N$, O and S; and wherein aryl, phenyl and heteroaryl may be optionally substituted with one or more substituents $L^{Ar}$; and $R^{NT2}$ is selected from the group consisting of H and $C_{1-6}$-alkyl; or $R^{NT1}$ and $R^{NT2}$ are linked to form one group selected from the group consisting of a $C_{3-5}$-alkylene group, wherein 1 or 2 —$CH_2$-groups independently of each other are replaced by $NR^N$, O, C(=O), S, S(=O) or S(=O)$_2$; and which may be optionally substituted with one or more substituents independently of each other selected from F, $C_{1-4}$-alkyl, $(R^N)_2N$, OH and $C_{1-4}$-alkyl-O—;

$L^{Ar}$ is selected from the group consisting of F, Cl, Br, I, CN, OH, $NO_2$, $C_{1-4}$-alkyl-, $C_{1-4}$-alkyl-O—, $(R^N)_2N$—C(=O), $(R^N)_2N$—, and $C_{1-4}$-alkyl-S(=O)$_2$—, wherein each alkyl group may be optionally substituted with one or more substituents independently of each other selected from F, Cl, CN, OH and $C_{1-3}$-alkyl-O—; and $L^P$ is selected from the group consisting of F and $C_{1-3}$-alkyl, wherein the alkyl group may be substituted with one or more F-atoms; and $L^Q$ is selected from the group consisting of F, Cl, CN, OH, $C_{1-4}$-alkyl, $C_{3-7}$-cycloalkyl-, $F_2HC$, $F_3C$, $C_{1-4}$-alkyl-O—, $F_2HC$—O—, $F_3C$—O— and $C_{3-7}$-cycloalkyl-O—; and $R^2$ is selected from the group consisting of F, Cl, Br, I, CN, OH, $NO_2$, $C_{1-6}$-alkyl-, $C_{2-6}$-alkenyl-, $C_{2-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—(=O)—, $R^{NT1}R^{NT2}N$—S(=O)$_2$—, $R^{NT1}R^{NT2}N$—C(=O)—$(R^N)N$—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$alkyl-S(=O)$_2$—, $R^{NT1}R^{NT2}N$—S(=O)$_2$—, aryl, heteroaryl, and heterocyclyl, and wherein aryl denotes phenyl or naphthyl, and wherein heteroaryl is a 5- or 6-membered aromatic carbocyclic ring which contains 1, 2, 3 or 4 heteroatoms independently of each other selected from N, $NR^N$, O and S; and wherein heterocyclyl is a 4- to 7-membered unsaturated or saturated carbocyclic ring in which 1, 2, or 3 —$CH_2$-groups independently of each other are replaced by $NR^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from $L^{Ar}$; and n is an integer selected from 0, 1, 2, 3, or 4;

or a salt thereof.

2. A compound according to claim 1, wherein $R^1$ is selected from a group consisting of

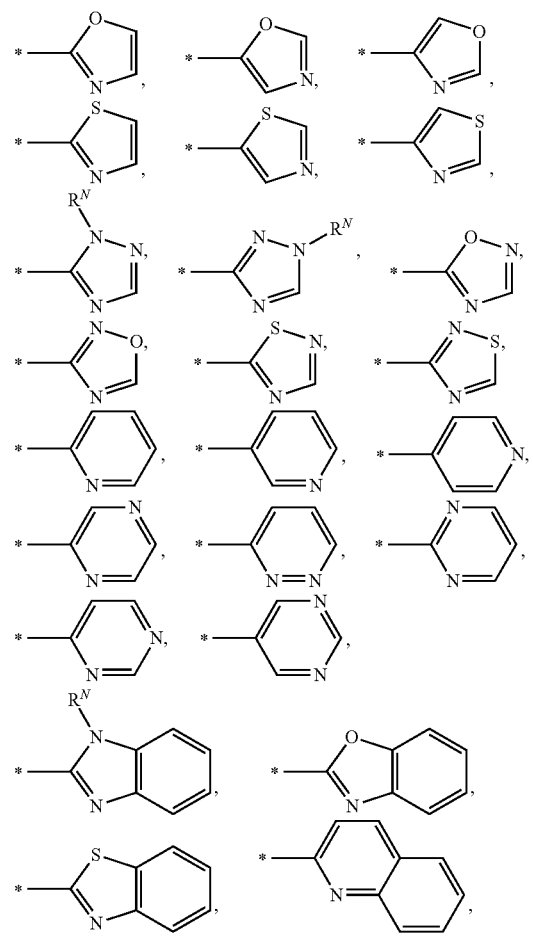

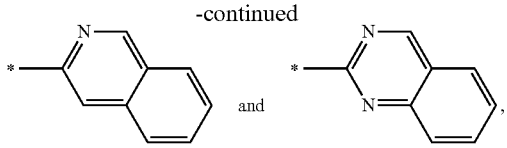

wherein each ring is optionally substituted with one substituent $L^{Ar}$ and each group is optionally substituted with one substituent $R^2$;

wherein $R^2$, $R^N$ and $L^{Ar}$ are defined as in claim 1.

3. A compound according to claim 1, wherein $R^1$ is selected from a group consisting of

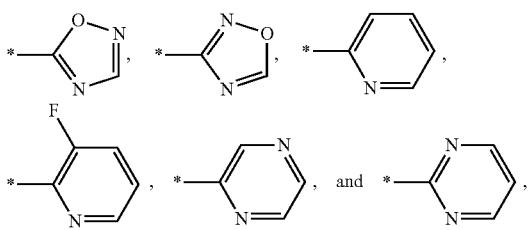

wherein each ring is optionally additionally substituted with one $R^2$, and $R^2$ is selected from the group consisting of F, NC—, $C_{1-4}$-alkyl-, $F_3C$—, $C_{1-3}$-alkyl-O— and phenyl, wherein the phenyl ring is optionally monosubstituted with F, Cl, $CH_3$, or —$OCH_3$.

4. A compound according to claim 1, wherein n is 0 or 1 and $L^P$ is F.

5. A compound according to claim 1, wherein Ar is selected from a group consisting of a phenyl, a tetrazolyl, and a heteroaromatic ring selected from pyridinyl, pyrazinyl, pyridazinyl, pyrimidinyl, isoxazolyl, oxazolyl, oxadiazolyl, imidazolyl, pyrazolyl, triazolyl, thienyl and thiazolyl, wherein said phenyl and heteroaromatic ring are optionally substituted with one or more substituents independently of each other selected from $L^{Ar}$, and wherein said phenyl, tetrazolyl and heteroaromatic ring are optionally substituted with a group T and wherein in heteroaromatic ring the H-atom in one NH group is optionally replaced by $R^N$, wherein T, $R^N$ and $L^{Ar}$ are defined as in claim 1.

6. A compound according to claim 5, wherein T is selected from a group consisting of CN, $C_{1-3}$-alkyl-, NC—$C_{1-3}$-alkyl-, $C_{1-3}$-alkyl-O—, $C_{1-3}$-alkyl-S(=O), $C_{1-3}$-alkyl-S(=O)$_2$, $R^{NT1}R^{NT2}$N—S(=O)$_2$—, $R^{NT1}R^{NT2}$N—C(=O)—, $R^{NT1}R^{NT2}$N—, $C_{1-3}$-alkyl-S(=O)$_2$—$CH_2$—, and $R^{NT1}R^{NT2}$N—C(=O)—$CH_2$—; wherein $R^{NT1}$ and $R^{NT2}$ are defined as in claim 1.

7. A compound according to claim 1, wherein Ar is selected from a group consisting of

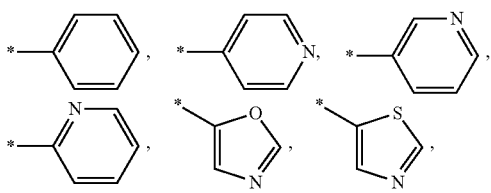

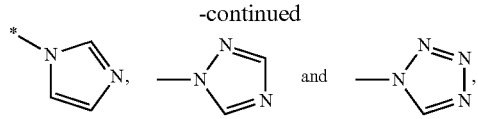

wherein each of the beforementioned groups is optionally substituted with one substituent selected from the group consisting of CN, $CH_2CN$, $CH_3$, $CH_2CH_3$, $OCH_2CH_3$, and $SO_2CH_3$ and may additionally be substituted with one F atom.

8. A compound according to claim 1, wherein HetAr-Ar is selected from a group consisting of

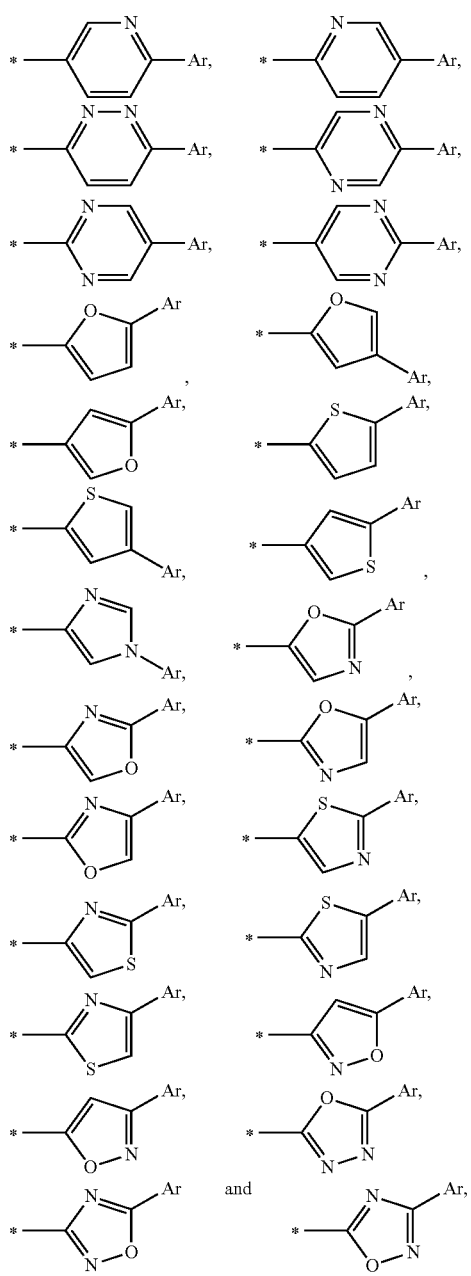

wherein each ring may be optionally substituted with one or two substituents independently of each other selected from $L^Q$.

9. A compound of formula I according to claim 1, wherein R$^1$ is selected from a group consisting of

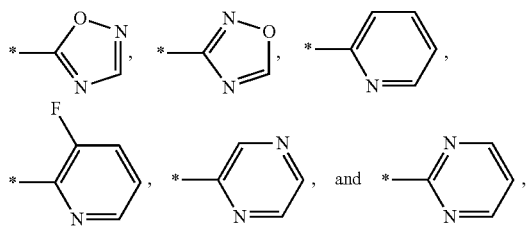

wherein R$^1$ is optionally substituted with Cl, C$_{1-4}$-alkyl-, cyclopropyl, F$_3$C—, or phenyl, HetAr-Ar is selected from a group consisting of

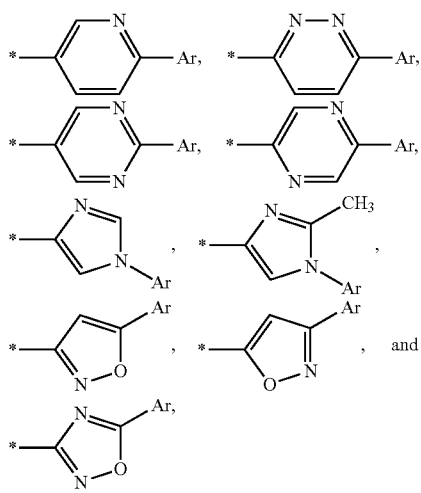

wherein Ar is selected from a group consisting of

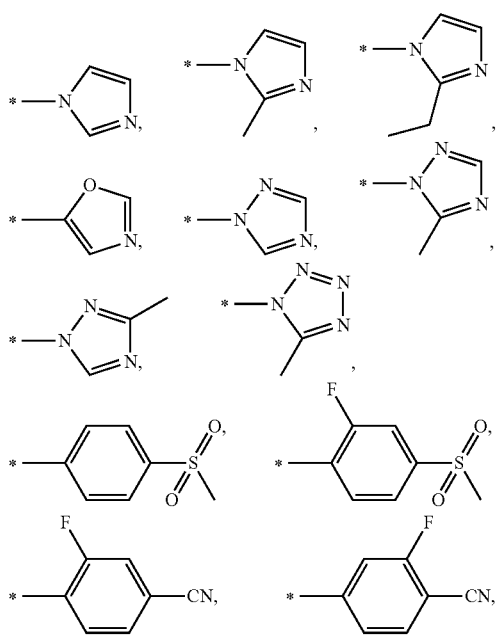

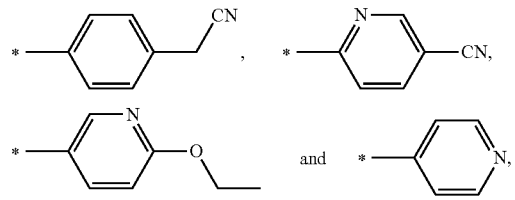

L$^P$ is F and n is 0 or 1.

10. A compound according to claim 1 selected from the group consisting of:

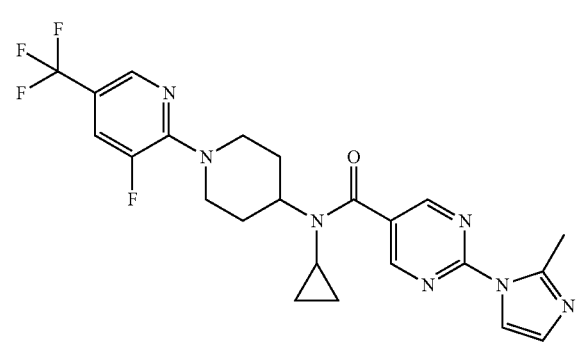

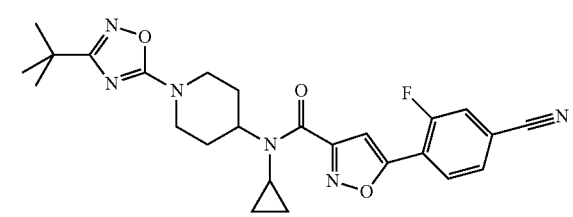

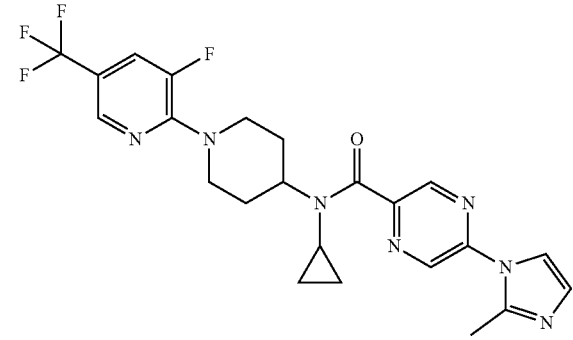

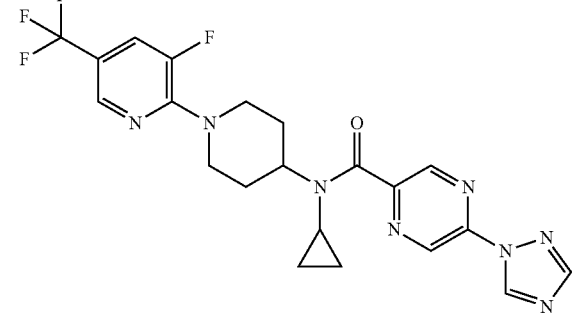

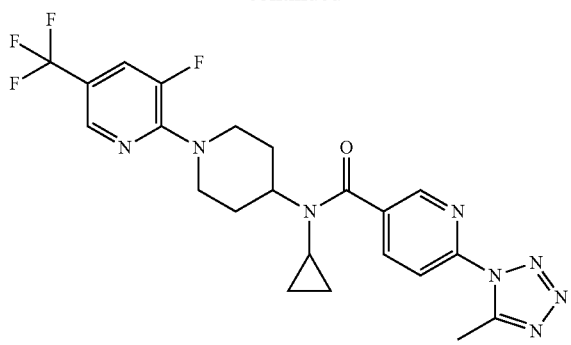
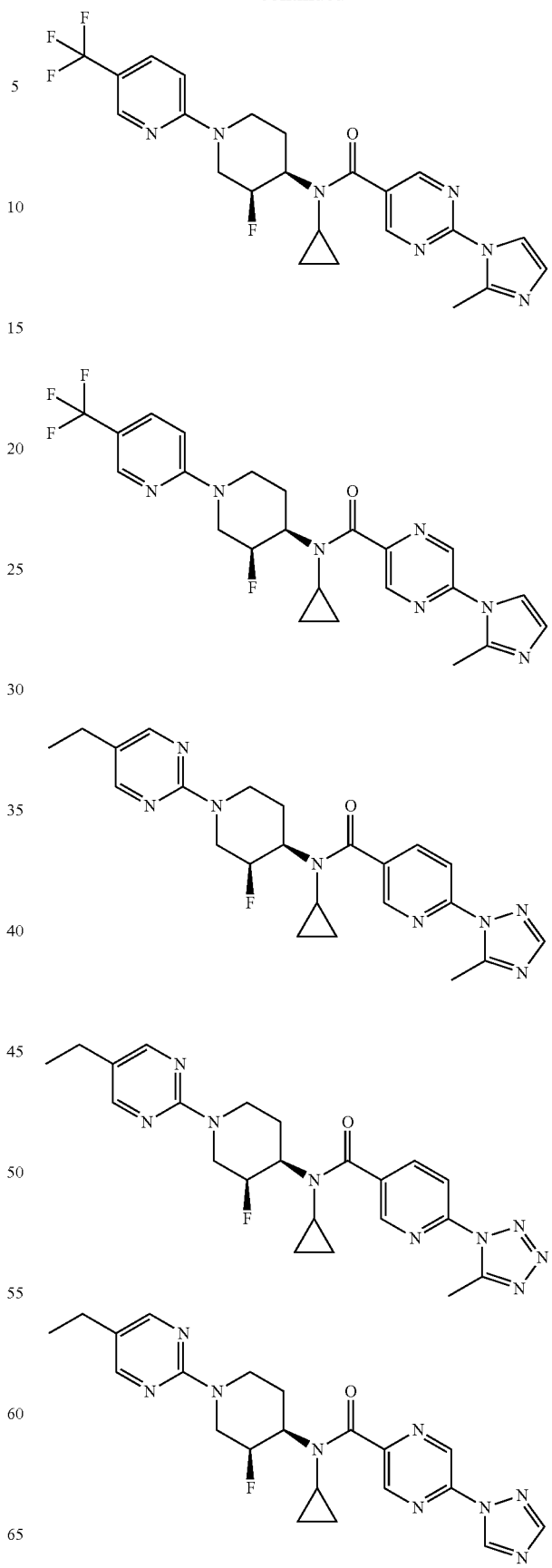

-continued

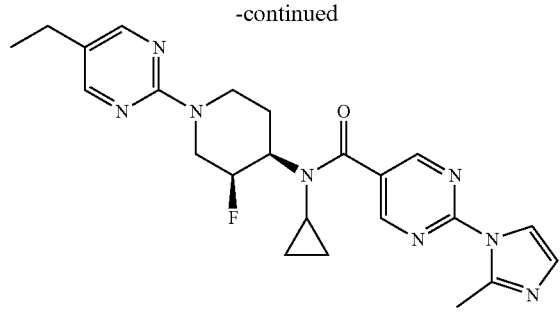
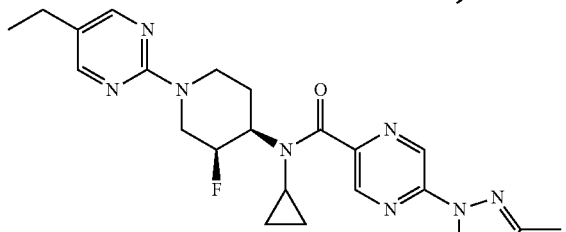
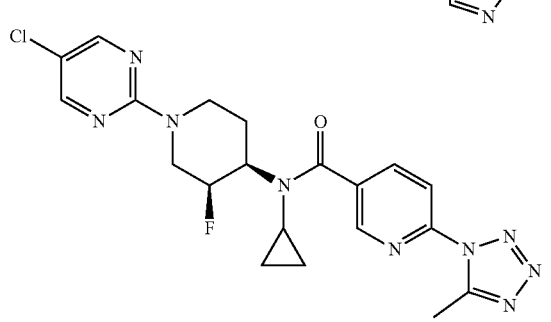
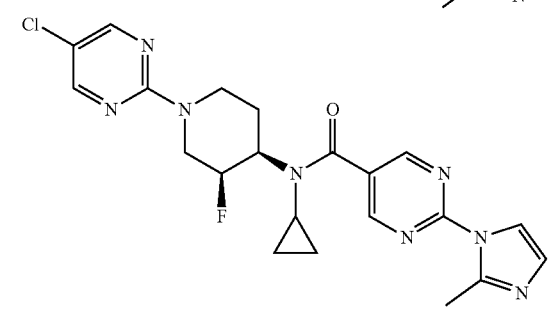

-continued

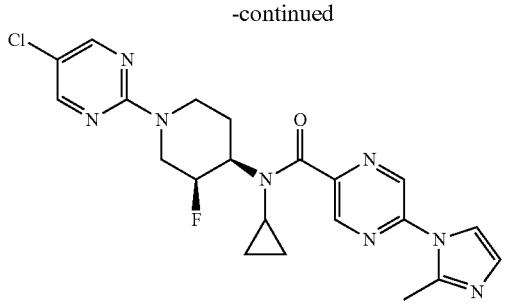

and

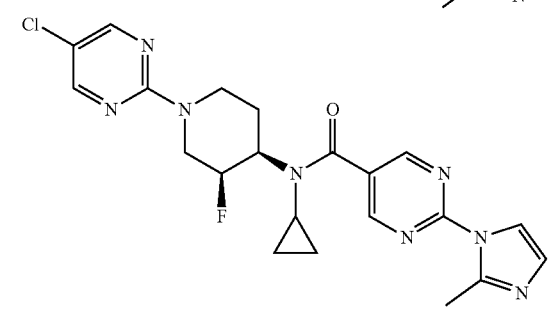

or a pharmaceutically acceptable salt thereof.

11. A pharmaceutically acceptable salt of a compound according to claim 1.

12. A pharmaceutical composition comprising one or more compounds according to claim 1 or one or more pharmaceutically acceptable salts thereof, optionally together with one or more inert carriers and/or diluents.

13. A method for treating diseases or conditions which are mediated by the G-protein-coupled receptor GPR119 comprising administering to a patient in need thereof a therapeutically effective amount of a compound according to claim 10, wherein the diseases or conditions are diabetes, dyslipidemia or obesity.

14. A pharmaceutical composition comprising one or more compounds according to claim 1 or one or more pharmaceutically acceptable salts thereof and one or more additional therapeutic agents, optionally together with one or more inert carriers and/or diluents.

* * * * *